US007989139B2

(12) United States Patent
Satake et al.

(10) Patent No.: US 7,989,139 B2
(45) Date of Patent: *Aug. 2, 2011

(54) AZO-METAL CHELATE DYE AND OPTICAL RECORDING MEDIUM

(75) Inventors: Kenichi Satake, Minato-ku (JP); Yuko Naitou, Machida (JP); Hisashi Shoda, Minato-ku (JP); Yuki Suzuki, Yokohama (JP)

(73) Assignee: Mitsubishi Kagaku Media Co., Ltd., Tokyo (JP)

( * ) Notice: Subject to any disclaimer, the term of this patent is extended or adjusted under 35 U.S.C. 154(b) by 1 day.

This patent is subject to a terminal disclaimer.

(21) Appl. No.: 12/481,603

(22) Filed: Jun. 10, 2009

(65) Prior Publication Data

US 2009/0246687 A1 Oct. 1, 2009

Related U.S. Application Data

(63) Continuation of application No. 11/205,078, filed on Aug. 17, 2005, now Pat. No. 7,642,036, which is a continuation of application No. PCT/JP2004/013170, filed on Sep. 9, 2004.

(30) Foreign Application Priority Data

Sep. 11, 2003 (JP) ................................. 2003-319766

(51) Int. Cl.
*G11B 7/24* (2006.01)
*C09B 45/14* (2006.01)

(52) U.S. Cl. ................... 430/270.16; 430/945; 534/723; 428/64.4; 428/64.8; 369/284

(58) Field of Classification Search ........................ None
See application file for complete search history.

(56) References Cited

U.S. PATENT DOCUMENTS

| 6,225,023 | B1 | 5/2001 | Okamoto et al. |
| 6,226,255 | B1 | 5/2001 | Suzuki et al. |
| 6,232,036 | B1 | 5/2001 | Suzuki et al. |

(Continued)

FOREIGN PATENT DOCUMENTS

CN 1748004 A 3/2006

(Continued)

OTHER PUBLICATIONS

JPO abstract of JP 10-208303.

*Primary Examiner* — Martin J Angebranndt
(74) *Attorney, Agent, or Firm* — Oblon, Spivak, McClelland, Maier & Neustadt, L.L.P.

(57) ABSTRACT

The azo-metal chelate dye to which the present invention is applied is a compound formed as follows: for example, 1,3,4-thiadiazole ring is selected as the diazo component; the diazo component is combined with a coupler component having condensed rings including a fluorine-substituted alkylsulfonylamino group and an amino group, to form an azo dye compound; and the azo dye compound forms chelate bonds with at least one metal selected from the group consisting of Co, Ni, Cu and Pd. Here, two absorption bands (OD1 and OD2) are seen in the absorption spectrum, which is measured in a range of 400 to 800 nm wavelengths. The azo-metal chelate dye is characterized in that the optical density ratio (OD2/OD1) of the two absorption bands is greater than 1.25. By using this azo-metal chelate dye, an optical recording medium capable of high-speed recording is provided.

14 Claims, 5 Drawing Sheets

U.S. PATENT DOCUMENTS

| | | |
|---|---|---|
| 6,284,877 B1 | 9/2001 | Okamoto et al. |
| 7,507,524 B2 * | 3/2009 | Satake et al. ............. 430/270.16 |
| 7,642,036 B2 * | 1/2010 | Satake et al. ............. 430/270.16 |
| 2002/0051941 A1 | 5/2002 | Shoda et al. |
| 2006/0235210 A1 | 10/2006 | Berneth et al. |
| 2006/0257613 A1 | 11/2006 | Berneth et al. |
| 2007/0054219 A1 | 3/2007 | Satake et al. |

FOREIGN PATENT DOCUMENTS

| | | |
|---|---|---|
| EP | 0 483 382 A1 | 5/1992 |
| EP | 0 717 403 A1 | 6/1996 |
| EP | 0 844 243 | 5/1998 |
| EP | 0 996 123 A2 | 4/2000 |
| JP | 03-268994 | 11/1991 |
| JP | 10-86519 | 4/1998 |
| JP | 10-204070 | 8/1998 |
| JP | 11-012483 | 1/1999 |
| JP | 11-130970 | 5/1999 |
| JP | 11-166125 | 6/1999 |
| JP | 11-310728 | 11/1999 |
| JP | 2000-309722 | 11/2000 |
| JP | 2004-042504 | 2/2004 |

* cited by examiner

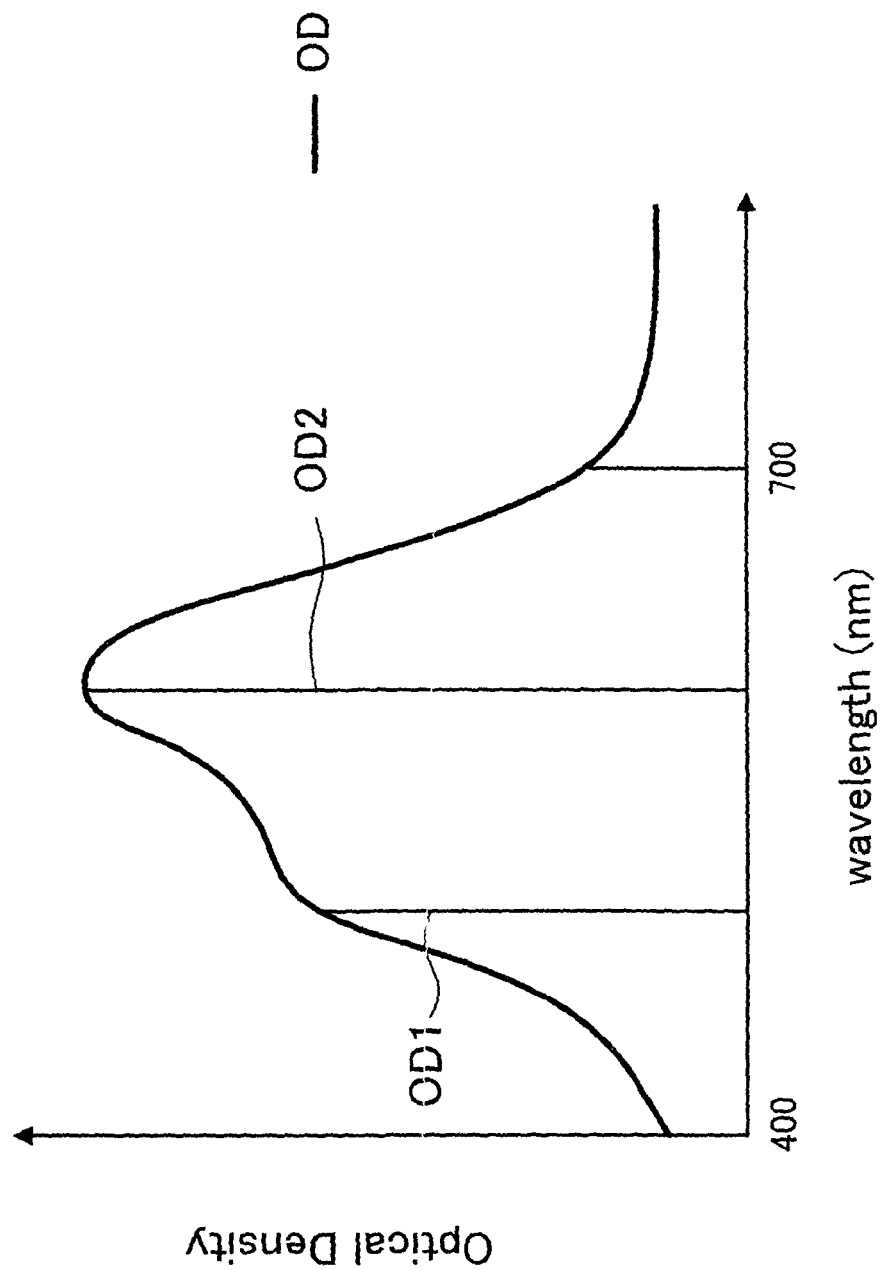

AZO-METAL CHELATE DYE AND OPTICAL RECORDING MEDIUM

This is a continuation application of U.S. application Ser. No. 11/205,078, filed Aug. 17, 2005, now U.S. Pat. No. 7,642,036, which is a CON of PCT/JP04/13170 filed on Sep. 9, 2004.

TECHNICAL FIELD

The present invention relates to an azo-metal chelate dye and the like suitable for high-speed recording. More specifically, the present invention relates to an azo-metal chelate dye which exhibits a specific film absorption spectrum and to an optical recording medium using this azo-metal chelate dye (in the present invention, an optical recording medium is referred to as "a disc" or "an optical disc" in some cases).

BACKGROUND ART

In recent years, as computers become faster and hard disc capacity increases, volume of data which can be dealt with has increased. In response to this, large-capacity recording media are now in increasing demand and DVD-Rs have therefore been developed as large-capacity recordable CDs. Various types of dyes, including cyanine dyes and metal chelate dyes, have been proposed for use in the recording layer of DVD-Rs. A number of optical media have been proposed which use metal chelate dyes that are excellent in light-resistance and weather-resistance among these dyes (See Patent Document 1).

In addition, there is a report about an azo-metal chelate dye consisting of a metal and an azo dye compound, where the azo dye compound is formed of a diazo component including nitrogen atoms and a coupler component including a fluorine-substituted alkylsulfonylamino group (See Patent Document 2). Moreover, there is a report to the effect that the recording characteristics of an optical recording medium, such as light-resistance and durability, can be improved by using an azo-metal chelate dye as a recording layer of the optical recording medium. Here, the azo-metal chelate dye consists of a metal and an azo dye compound which includes a coupler component where an amino group on a benzene ring forms a fused heterocycle (See Patent document 3).

Patent Document 1: Japanese Patent Laid-Open No. Hei03-268994 (JP3-268994)
Patent Document 2: Japanese Patent Laid-Open No. Hei11-166125 (JP11-166125)
Patent Document 3: Japanese Patent Laid-Open No. 2000-309722 (JP2000-309722)

DISCLOSURE OF THE INVENTION

Problems to be Solved by the Invention

Incidentally, along with further increase in data volume, greater importance is given to increase in the speed with which information is recorded on optical recording media. For example, normal recording speed is approximately 3.5 m/s in DVD-Rs (hereinafter, referred to as 1×-speed recording in some cases). However, there is a market demand for optical recording media capable of recording information at a high-speed linear velocity of approximately 28 m/s (hereinafter, referred to as 8× in some cases) or more, which corresponds to eight times the speed 1×.

The development of dyes that are particularly suitable for high-speed recording is an issue to be addressed in order to respond to this market demand.

In view of the foregoing issue, it is an object of the present invention to provide an azo-metal chelate dye capable of high-speed recording and an optical recording medium using this azo-metal chelate dye.

Means for Solving the Problems

In consideration of the fact that it is difficult to achieve high reflectivity of an optical recording medium in high-speed recording and the fact that it is possible to achieve high reflectivity of an optical recording medium if the high refraction index of a recording layer is increased, the present inventors set an objective of obtaining an azo-metal chelate dye with a higher refraction index. Specifically, the present inventors focused on the following two optical densities that can be obtained by measuring the absorption spectrum of a coating film including dyes. That is, the optical density OD2 at the absorption peak or absorption shoulder on the long wavelength side; and the optical density OD1 at the absorption peak or absorption shoulder on the short wavelength side, both of which are in the absorption band ranging from 500 to 700 nm. The present inventors then determined that it is possible to provide dyes with a high refraction index by setting the OD2/OD1 value higher than a predetermined value, and therefore completed the present invention.

Specifically, the gist of the present invention is an azo-metal chelate dye consisting of a metal and an azo dye compound. The azo-metal chelate dye is characterized in that the OD2/OD1 value measured by the following method is greater than 1.25.

(Method of Measuring the OD2/OD1 Value)
(1) After adding 20 mg of azo-metal chelate dye into 2 g of an octafluoropentanol (OFP) solvent, supersonic dispersion is performed at temperatures between 50° C. and 55° C. for 60 minutes to obtain a solution A. The solution A is then cooled to room temperature (25±5° C.) to obtain a solution B.
(2) The solution B is applied onto a polycarbonate substrate by spin coating at a rotating speed of 800 rpm. The substrate onto which the solution B has been spin coated is then annealed at 80° C. for 5 minutes. The substrate thus obtained, onto which the solution B has been spin coated, being referred to as a coated substrate A.
(3) The absorption spectrum of the coated substrate A is measured in a range of 400 to 800 nm.
(4) Concerning the absorption peaks seen in a range of 500 to 700 nm in the obtained absorption spectrum, the absorption peak at which the optical density is the greatest and the absorption peak at which the optical density is the second greatest are selected. Here, the optical density at the peak on the long wavelength side is defined as OD2 and the optical density at the peak on the short wavelength side is defined as OD1. Then, the OD2/OD1 value is calculated.

Another gist of the present invention is an optical recording medium having a recording layer on a substrate, on which recording and/or reading of information is performed by use of applied light. The optical recording medium is characterized in that the recording layer contains an azo-metal chelate dye consisting of a metal and an azo dye compound, and that the azo-metal chelate dye has the OD2/OD1 value of greater than 1.25, which is measured by the following method.
(Method of Measuring the OD2/OD1 Value)
(1) After adding 20 mg of azo-metal chelate dye into 2 g of an octafluoropentanol (OFP) solvent, supersonic dispersion is performed at temperatures between 50° C. and 55° C. for 60 minutes to obtain a solution A. The solution A is then cooled to room temperature (25±5° C.) to obtain a solution B.

(2) The solution B is applied onto a polycarbonate substrate by spin coating at a rotating speed of 800 rpm. The substrate onto which the solution B has been spin coated is then annealed at 80° C. for 5 minutes. The substrate thus obtained, onto which the solution B has been spin coated, being referred to as a coated substrate A.

(3) The absorption spectrum of the coated substrate A is measured in a range of 400 to 800 nm.

(4) Concerning the absorption peaks seen in a range of 500 to 700 nm in the obtained absorption spectrum, the absorption peak at which the optical density is the greatest and the absorption peak at which the optical density is the second greatest are selected. Here, the optical density at the peak on the long wavelength side is defined as OD2 and the optical density at the peak on the short wavelength side is defined as OD1. Then, the OD2/OD1 value is calculated.

According to the present invention, an azo-metal chelate dye allowing for high-speed recording and an optical recording medium capable of high-speed recording using this azo-metal chelate dye are provided.

BRIEF DESCRIPTION OF THE DRAWINGS

FIG. 5 shows an example of the absorption spectrum of a dye film of an azo-metal chelate in a case where absorption shoulders are seen.

BEST MODE FOR CARRYING OUT THE INVENTION

Figure 1:
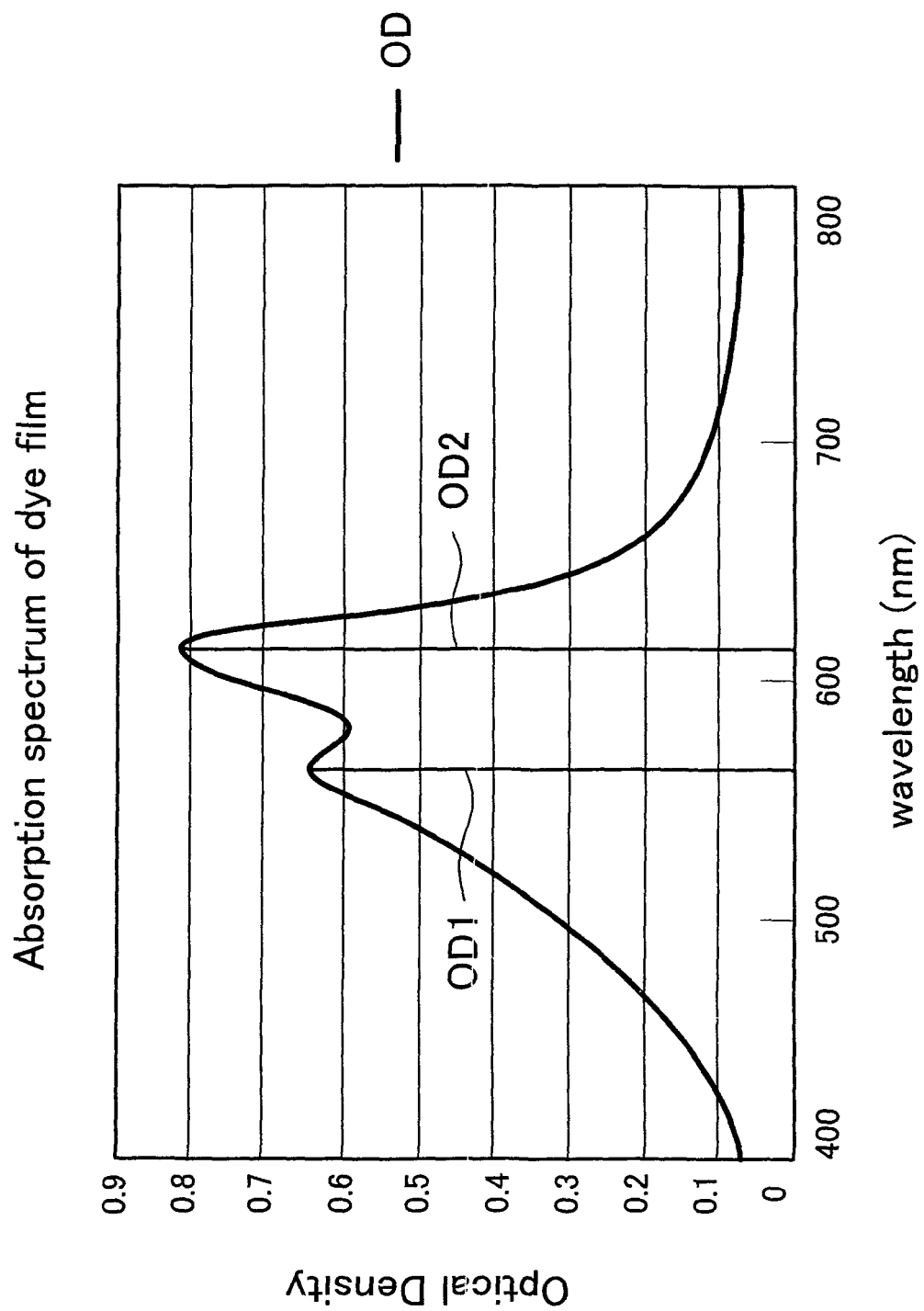
FIG. 1 shows the absorption spectrum of a coated substrate A where a dye prepared in an example 1 is used.

The best mode for carrying out the invention (hereinafter referred to as an embodiment) will be described in detail below. Note that, the present invention is not limited to the following embodiment, and can be implemented with various modifications within the spirit thereof.

In the present embodiment, used is an azo-metal chelate dye consisting of a metal and an azo dye compound, which has the OD2/OD1 value of larger than 1.25 which is measured by a predetermined measurement method.

A description will be given of a reason for setting the OD2/OD1 value to a predetermined value in the present embodiment.

As a high-speed recording method, a method can be employed in which a dye having a higher optical density (absorption) at the recording wavelength is used for efficient absorption of the recording laser light. This is the method for shifting the wavelength at which the maximum absorption of the dye occurs to longer wavelengths longer than that of the dye used in the conventional low-speed recording. However, when such a dye having the absorption maximum at longer wavelengths is used, the reflectivity of a disc tends to be decreased compared to the conventional one. For this reason, when using the above-described method, it is often difficult to satisfy the requirement concerning the reflectivity of optical discs. For example in DVDs, the standard, "disc should have a reflectivity of 45% or more" for readout from the recording portion, is often difficult to be satisfied. Accordingly, when using the above-described method, the reflectivity often needs to be secured at the expense of the recording sensitivity to some extent.

Different aspects from those in the above-described method were taken into consideration in the present embodiment, leading to identification of a dye for high-speed recording which can provide sufficient reflectivity even in high-speed recording and is excellent in recording sensitivity. Hereinafter, a detailed description thereof will be given.

First, the present inventors set an objective of obtaining an azo-metal chelate dye with a higher refraction index on the basis of the knowledge that a dye film (recording layer) having a higher refraction index leads to higher reflectivity of a disc in a specific film thickness range (90 nm or less) (See Japanese Patent Laid-Open No. H10-208303 (JP10-208303), FIGS. 1 to 5, for example).

Meanwhile, in the absorption spectrum of the azo-metal chelate dye film, two absorption bands are seen in a range of 500 to 700 nm: that is, an absorption band considered to be generated due to localization of electrons in ligands; and an absorption band considered to be generated due to interaction between a metal and the ligands (See FIG. 1, note that the FIG. 1 will be described later).

In the present embodiment, out of the two absorption bands seen in the 500 to 700 nm range, the optical density at the absorption peak on the short wavelength side and the optical density of the absorption peak at the long wavelength side are defined as OD1 and OD2, respectively. It has been determined that an azo-metal chelate dye having particularly a high refraction index can be obtained by setting the OD2/OD1 value to greater than 1.25. As a result, an optical recording medium having sufficient reflectivity even in high-speed recording can be obtained. The OD2/OD1 value is measured by the following method.

(Method of Measuring the OD2/OD1 Value)

(1) After adding 20 mg of azo-metal chelate dye into 2 g of an octafluoropentanol (OFP) solvent, supersonic dispersion is performed at temperatures between 50° C. and 55° C. for 60 minutes to obtain a solution A. The solution A is then cooled to room temperature (25±5° C.) to obtain a solution B.

(2) The solution B is applied onto a polycarbonate substrate by spin coating at a rotating speed of 800 rpm. The substrate onto which the solution B is spin coated is then annealed at 80° C. for 5 minutes. The substrate thus obtained, onto which the solution B is spin coated, is referred to as a coated substrate A.

(3) The absorption spectrum of the coated substrate A is measured in a range of 400 to 800 nm.

(4) Concerning the absorption peaks seen in a range of 500 to 700 nm in the obtained absorption spectrum, the absorption peak at which the optical density is the greatest and the absorption peak at which the optical density is the second greatest are selected. Here, the optical density at the peak on the long wavelength side is defined as OD2 and the optical density at the peak on the short wavelength side is defined as OD1. The OD2/OD1 value is then calculated.

Hereinafter, the above-described processes (1) to (4) will be described.

First, 20 mg of azo-metal chelate dye, which is to be measured, is added into 2 g of an octafluoropentanol (OFP) solvent. Thereafter, supersonic dispersion is performed at temperatures between 50° C. and 55° C. for 60 minutes to obtain a solution A. The supersonic dispersion is performed in order to disperse or dissolve an azo-metal chelate dye into a solvent. Publicly known methods may be used for supersonic dispersion.

Next, the solution A is cooled to room temperature (25±5° C.) to obtain a solution B. A cooling method for the solution A is to leave the solution A at room temperature. Rapid cooling of the solution A by use of ice water and the like is not preferable because there is a possibility that crystallization is excessively accelerated. Here, after the solution A is cooled to room temperature, it is preferable that the solution A be filtrated through a filter (0.2 μm, for example). For the filter, Teflon filters (registered trademark, manufactured by Millipore Corporation) and the like can be cited. Filtration through a filter removes undisclosed components and components that have not been sufficiently dispersed in the solution A. The solution thus obtained is referred to as a solution B. However, if dyes that have not been dissolved in the solution A are observed, the supernatant thereof may be collected and used as the solution B.

Note that, as apparent from the above description, the azo-metal chelate dye may be present in the "solution A" in a state where the whole or part of the azo-metal chelate dye is dissolved in the solution A. Alternatively, the azo-metal chelate dye may be present in the "solution A" in a state where the whole or part of the azo-metal chelate dye is dispersed in the solution A.

Further, the solution B is applied onto a polycarbonate substrate by spin coating at a rotating speed of 800 rpm. For the spin-coating device, publicly known devices can be employed that are used to form recording layers of CD-Rs and DVD-Rs. Specifically, the solution B is dropped on the polycarbonate substrate which is rotating at the speed of 800 rpm, thereby giving a coating film made of the solution B on the polycarbonate substrate.

Thereafter, the substrate onto which the solution B is spin coated is annealed at 80° C. for 5 minutes. This is performed in order to remove the solvent in the solution B. The solvent is preferably removed completely from the solution B by annealing the substrate at 80° C. for 5 minutes. However, the solvent does not necessarily have to be completely removed as long as the measurement of the absorption spectrum, which will be described later, can be performed well.

The substrate thus obtained, onto which the solution B is spin coated, is referred to as a coated substrate A. The absorption spectrum of the coated substrate A is measured in a range of 400 to 800 nm. Publicly known methods may be employed to measure the absorption spectrum. Specifically, the sample light (400 to 800 nm), which is used to measure the absorption spectrum, is applied from the substrate side of the coated substrate A. Air is used as a reference sample, and the intensity of light in the references sample and the intensity of light passed through the coated substrate A are measured. Then, the absorption spectrum of the coated substrate A is measured.

The following method can be cited as the more specific method for the absorption spectrum.

A disc onto which an azo-metal chelate dye film is applied is cut out to have a sector shape. Using ultraviolet-visible spectrophotometer, measurement is made by applying light from the surface (on the substrate side) that is opposite to the dye film side. For the spectroscope and measurement conditions employed in the measurement, commercially available spectroscopes and general measurement conditions can be employed. For example, the U-3300 (manufactured by Hitachi, Ltd.) was used in the examples of the present embodiment. The following measurement conditions were adopted: wavelength scan speed of 300 nm/min; optical density measuring (Absorbance) mode at a sampling cycle of 0.5 nm.

Azo-metal chelate dyes having higher OD2/OD1 values measured by this method exhibit higher refraction indices.

Figure 2:
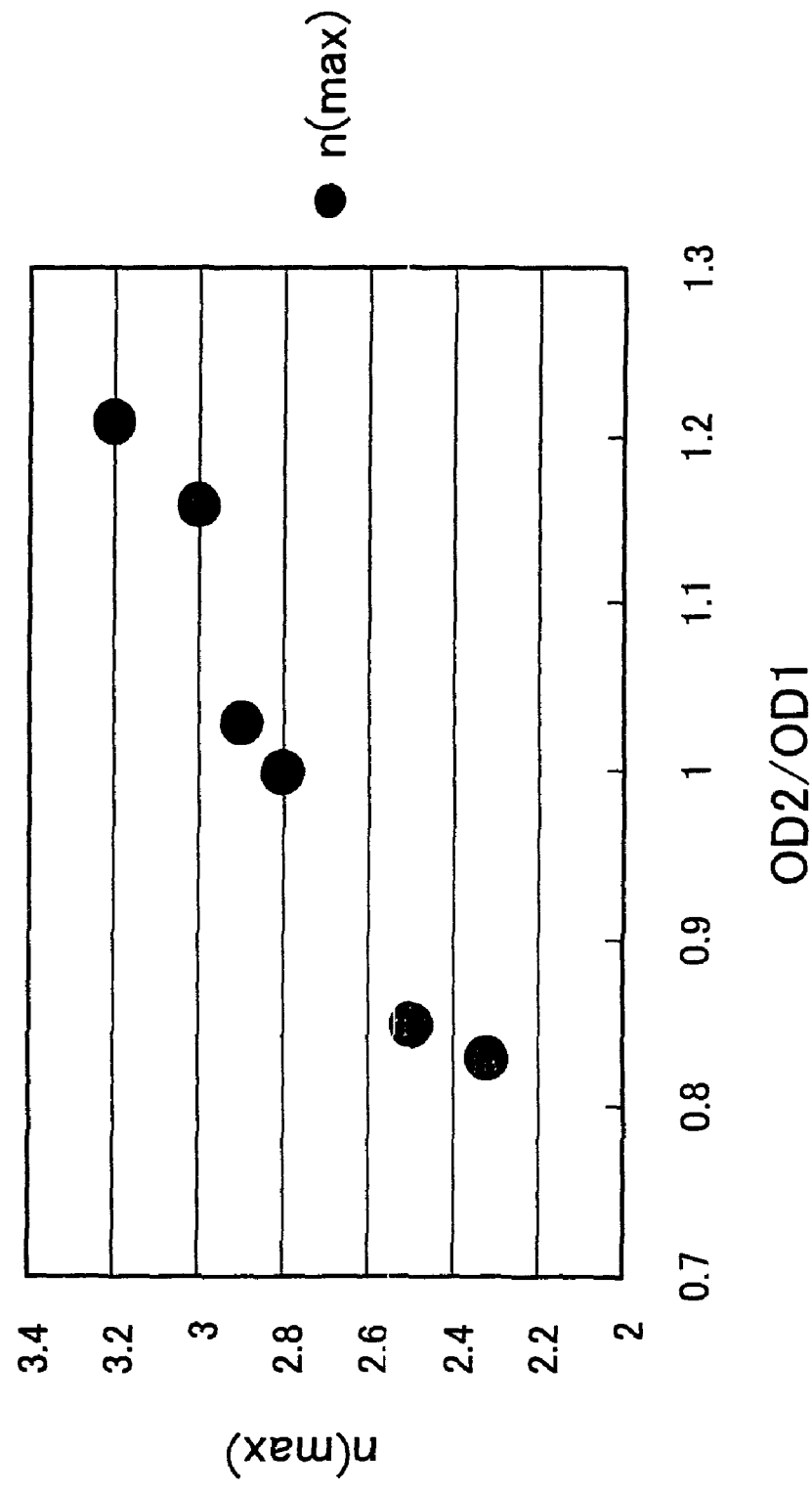
FIG. 2 shows the relation between the OD2/OD1 values and the refraction indices in the dye films where dyes (S-1) to (S-6) are used.

FIG. 2 is a graph showing the relation between the OD2/OD1 values and the refraction indices of dye films having various azo-metal chelate dyes to which the present embodiment is applied. The measurement result shown in FIG. 2 also establishes that the higher OD2/OD1 value leads to a higher refraction index. The measurement result shown in FIG. 2 indicates that the maximum refraction index of the film of the present embodiment, having the value of 1.25 or more, approximately equals to 3.3.

Because sufficient reflectivity for high-speed recording application can be obtained, the OD2/OD1 value is greater than 1.25, preferably 1.26 or more, more preferably 1.27 or more, further preferably 1.28 or more, and particularly preferably 1.29 or more. In addition, the higher OD2/OD1 values are preferable in consideration of the purpose of the present invention. However, the value is preferably 5 or less, more preferably 3 or less. If the value is greater than 5, the width of the absorption band is narrow, which may cause absorption to be dependent largely on wavelength.

It is to be noted that, in some cases, two or more distinct absorption peaks are not identified in the region raging from 500 to 700 nm when the absorption spectrum of a dye film of an azo-metal chelate dye is measured by the above-described measurement method. An example of such a case is where the absorption spectrum in the region raging from 500 to 700 nm is observed as an absorption spectrum having a plurality of absorption shoulders. In this case, among the obtained peaks, the absorption peak or absorption shoulder at which the optical density is the greatest and the absorption peak or absorption shoulder at which the optical density is the second greatest may be used to calculate the OD2/OD1 value.

FIG. 5 shows an example of the absorption spectrum of a dye film of an azo-metal chelate dye in a case where an absorption shoulder is seen. Concerning the absorption spectrum shown in FIG. 5, a method of determining the OD2/OD1 value will be described by way of example. When the absorption spectrum as shown in FIG. 5 is obtained, the absorption shoulder observed on the short wavelength side may be defined as OD1 in the absorption spectrum ranging from 400 to 700 nm.

As a preferable example of dyes having a high OD2/OD1 value, azo-metal chelate dyes having a specific structure can be cited. It has been determined that a disc using these dyes in the recording layer exhibits stable higher reflectivity than that of a disc using the conventional dyes in the recording layer, even when the recording layer has the absorption maximum wavelength at longer wavelengths.

Hereinafter, a description will be given of an example of an azo-metal chelate dye having the above-described specific structure.

First, 1,3,4-thiadiazole ring is selected as the diazo component among heterocyclic rings including nitrogen atoms. The diazo component is combined with the coupler component having condensed rings which include a fluorine-substituted alkylsulfonylamino group and an amino group, thereby preparing an azo dye compound. The recording layer containing an azo-metal chelate dye which is formed of this azo dye compound and a metal is preferable because it may exhibit excellent light-resistance and weather-resistance. In addition, the azo-metal chelate dye in which the 1,3,4-thiadiazole ring, that is, the diazo component, is substituted with a hydrogen atom or a ester group is preferable because it tends to exhibit the OD2/OD1 value that satisfies the requirements of the present embodiment. This is considered to be due to the fact that azo-ligands may coordinate to a metal ion with small steric hindrance, which may be accomplished by selecting, as a substituent of the diazo component, a hydrogen atom which is smallest in terms of spatial structure or an ester group which is highly polarized. A specific example of this structure is as follows:

(formula 1)

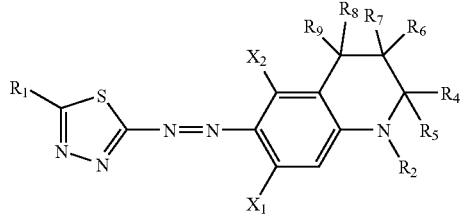

(1)

(where $R_1$ represents a hydrogen atom or an ester group represented as $CO_2R_3$, $R_3$ represents a straight or branched chain alkyl group which may be substituted or a cycloalkyl group which may be substituted, $R_2$ represents a straight or branched chain alkyl group which may be substituted, at least one of $X_1$ and $X_2$ represents a $NHSO_2Y$ group, Y represents a straight or branched chain alkyl group which is substituted with at least two fluorine atoms, $R_4$ and $R_5$ independently represents a hydrogen atom or a straight or branched chain alkyl group which may be substituted, and $R_6$, $R_7$, $R_8$ and $R_9$ independently represents a hydrogen atom or a alkyl group having 1 to 2 carbon atoms)

Chelate bonds are formed between the azo dye compound represented by the above-described formula (1) and a metal, thereby forming an azo-metal chelate dye to which the present embodiment is applied. In addition, the azo dye compound represented by the above-described formula (1) is formed in such a way that the diazo component, which is 1,3,4-thiadiazole ring, is combined with the coupler component having condensed rings including a fluorine-substituted alkylsulfonylamino group and an amino group.

A substituent $R_1$ in the diazo component represents a hydrogen atom or an ester group represented as $CO_2R_3$. $R_3$ represents a straight or branched chain alkyl group which may be substituted or a cycloalkyl group which may be substituted. A substituent in $R_3$ is not particularly limited as long as it is a typical element such as oxygen, nitrogen and sulfur, in addition to a halogen atom. As $R_3$, for example, an unsubstituted straight or branched chain alkyl group, an unsubstituted cycloalkyl group, a fluorine-substituted straight or branched chain alkyl group, or a straight or branched chain alkyl group which is substituted with an alkoxy group is preferable. Particularly preferably, $R_3$ represents a hydrogen atom; a straight or branched chain alkyl group having 1 to 4 carbon atoms such as an ethyl group, a propyl group, an isopropyl group, a butyl group, an isobutyl group, a t-butyl group and a sec-butyl group; and a cycloalkyl group having 3 to 8 carbon atoms such as a cyclopropyl group, a cyclobutyl group, a cyclopentyl group, a cyclohexyl group and a cycloheptyl group. From the reason that the steric hindrance effect is small, a straight chain alkyl group having 1 to 2 carbon atoms such as a methyl group and an ethyl group; and a cycloalkyl group having 3 to 6 carbon atoms such as a cyclopentyl group and a cyclohexyl group are particularly preferable.

From the viewpoint of satisfying the certain OD2/OD1 value in the present embodiment, the substituent $R_1$ in the diazo component is most preferably a hydrogen atom which shows smallest steric hindrance effect. As preferable examples of the specific compound for this diazo component, the compounds having the structures shown in the following (formulae 2) can be cited.

(formulae 2)

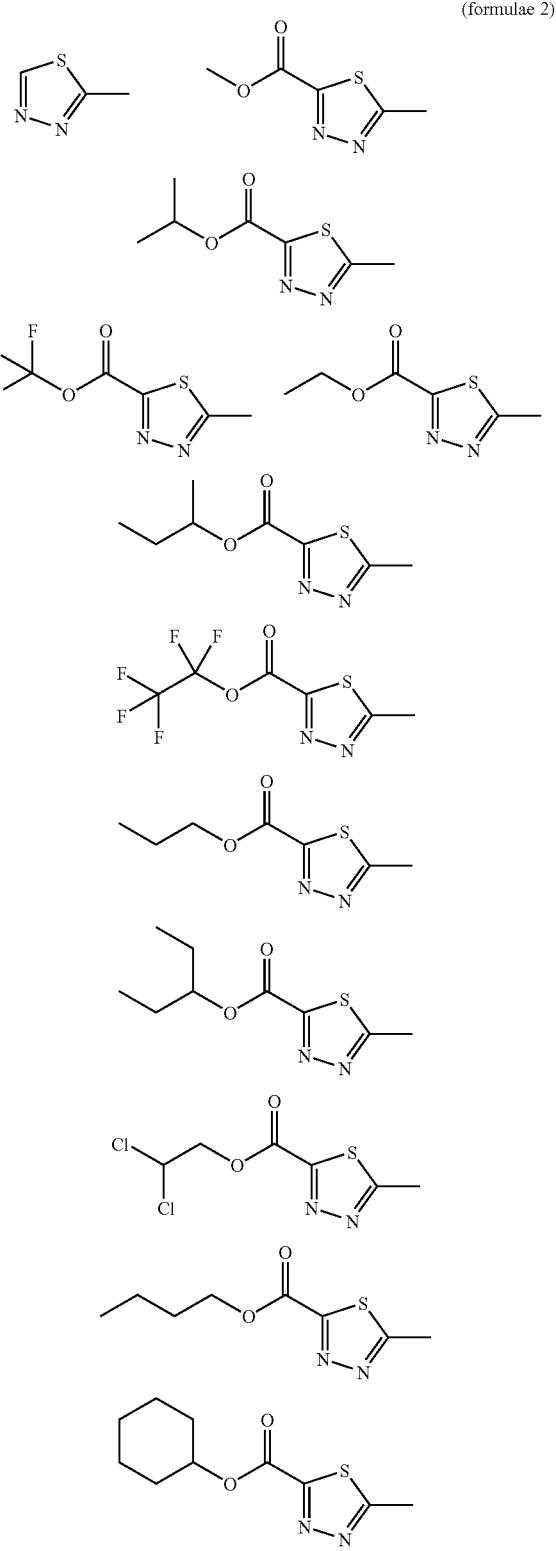

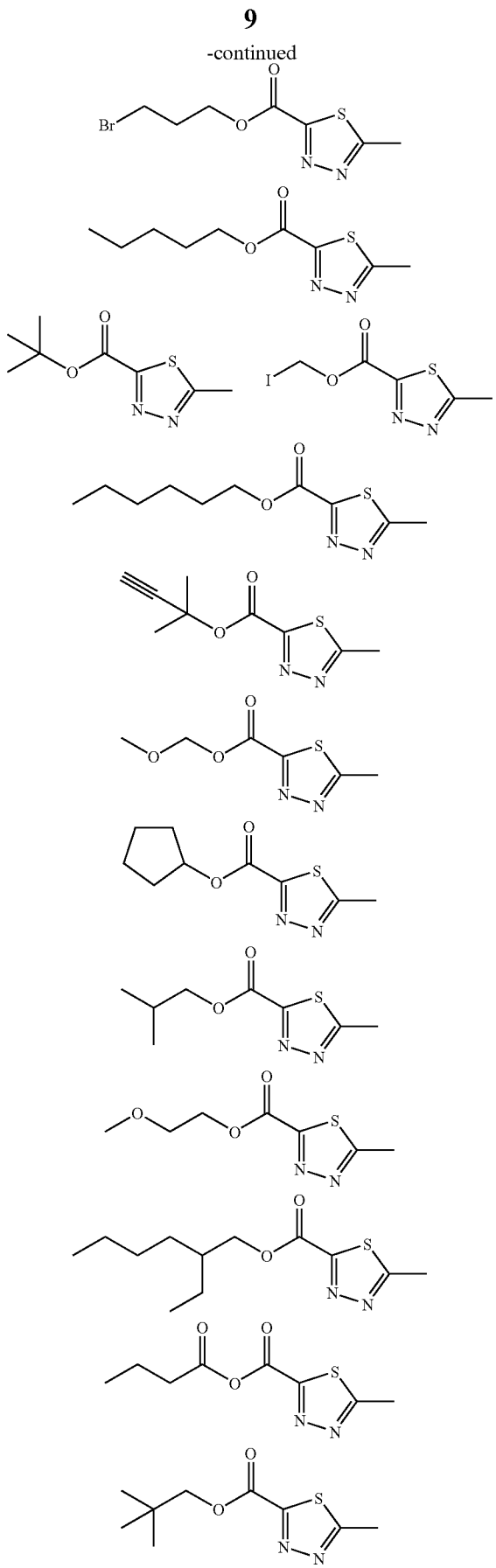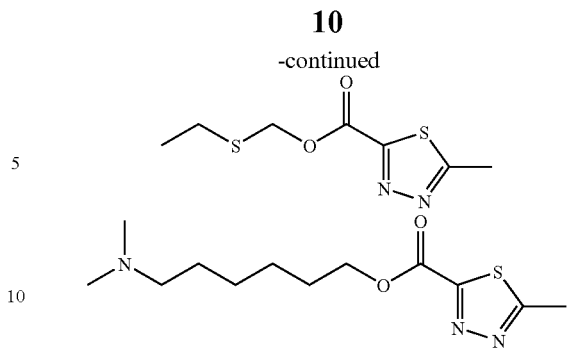

At least one of $X_1$ and $X_2$ in the coupler component represents $NHSO_2Y$. In this case, preferably, any one of $X_1$ and represents $NHSO_2Y$, and more preferably, $X_1$ represents $NHSO_2Y$. $X_2$ is not particularly limited in a case where $X_1$ represents $NHSO_2Y$, and $X_1$ is not particularly limited in a case where $X_2$ represents $NHSO_2Y$. However, a hydrogen atom is preferable in consideration of simplicity of synthesis.

Y represents a straight or branched chain alkyl group which is substituted with at least two fluorine atoms. For the alkyl group, a straight or branched chain alkyl group having 1 to 6 carbon atoms is more preferable. More preferably, Y represents a straight chain alkyl group having 1 to 3 carbon atoms. The number of fluorine atoms to be introduced is generally 2 or more; whereas normally 7 or less, preferably 5 or less, and more preferably 3 or less. Specific example of Y includes a difluoromethyl group, a trifluoromethyl group, a pentafluoroethyl group, a pentafluoropropyl group, a 2,2,2-trifluoroethyl group and a 3,3,3-trifluoropropyl group. For Y, a trifluoromethyl group and a 2,2,2-trifluoroethyl group are particularly preferable.

$R_4$ and $R_5$ independently represent a hydrogen atom or a straight or branched chain alkyl group which may be substituted. For $R_4$ and $R_5$, for example,
a hydrogen;
a straight chain alkyl group having 1 to 6 carbon atoms such as a methyl group, an ethyl group, an n-propyl group, an n-butyl group, n-pentyl group and an n-hexyl group;
a branched alkyl group having 3 to 8 carbon atoms such as a isopropyl group, a sec-butyl group, an isobutyl group, a t-butyl group, 2-ethylhexyl group, a cyclopropyl group and a cyclohexylmethyl group;
a halogen atom such as a fluorine atom, a chlorine atom, a bromine atom and an iodine atom;
an alkoxy group having 1 to 8 carbon atoms such as a methoxy group, an ethoxy group, an n-propoxy group, an isopropoxy group, an n-butoxy group, an isobutoxy group, a sec-butoxy group, a t-butoxy group, an n-pentyloxy group, a cyclopropyloxy group, a cyclohexylmethyloxy group and a 2-ethylhexyloxy group;
an alkoxycarbonyl group having 2 to 9 carbon atoms such as a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a t-butoxycarbonyl group, an n-pentyloxycarbonyl group, a cyclopropyloxycarbonyl group, a cyclohexylmethoxycarbonyl group and a 2-ethylhexyloxycarbonyl group;
an alkylcarbonyloxy group having 2 to 9 carbon atoms such as a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a t-butylcarbonyloxy group, an n-pentylcarbonyloxy group, a cyclopropylcarbonyloxy group, a cyclohexylmethylcarbonyloxy group and a 2-ethylhexylcarbonyloxy group;
an alkylcarbonyl group having 2 to 9 carbon atoms such as an acetyl group, a propionyl group, a butyryl group, an isobutyryl group, a valeryl group, an isovaleryl group, a 2-methylbutyl group, a pivaloyl group, a hexanoyl group, a cyclopropylcarbonyl group, a cyclohexylmethylcarbonyl group and a 2-ethylhexylcarbonyl group;
a dialkylamino group having 2 to 16 carbon atoms such as a dimethylamino group, a diethylamino group, a dipropylamino group, a diisopropylamino group, a dibutylamino group, a diisobutylamino group, a di-t-butylamino group, a dihexylamino group, an ethylmethylamino group and a butylpentylamino group; and the like can be cited.

A straight or branched chain alkyl group and an alkoxy group may be further substituted with substituents cited as $R_4$ and $R_5$. A hydrogen atom, a straight chain alkyl group having 1 to 6 carbon atoms and an alkoxy group having 1 to 8 carbon atoms are preferable for $R_4$ and $R_5$. A hydrogen atom, an alkyl group having 1 to 2 carbon atoms and an alkoxy group having 1 to 2 carbon atoms are more preferable for $R_4$ and $R_5$. Preferably, the above-described alkyl and alkoxy groups are not substituted. A hydrogen atom, a methyl group, an ethyl group and a methoxy group are particularly preferable for $R_4$ and $R_5$.

$R_2$ represents a straight or branched chain alkyl group which may be substituted. For $R_2$, for example, a straight chain alkyl group having 1 to 6 carbon atoms such as a methyl group, an ethyl group, a propyl group, a butyl group, a pentyl group and a hexyl group; a branched chain alkyl group having 3 to 8 carbon atoms such as an isopropyl group, a sec-butyl group, an isobutyl group, a t-butyl group, a 2-ethylhexyl group, a cyclopropyl group, a cyclohexylmethyl group; and the like can be cited.

These alkyl groups may be substituted. For substituents, a halogen atom such as a fluorine atom, a chlorine atom, a bromine atom and an iodine atom;
an alkoxy group having 1 to 8 carbon atoms such as a methoxy group, an ethoxy group, an n-propoxy group, an isopropoxy group, an n-butoxy group, an isobutoxy group, a sec-butoxy group, a t-butoxy group, an n-pentyloxy group, a cyclopropyloxy group, a cyclohexylmethyloxy group and a 2-ethylhexyloxy group;
an alkoxycarbonyl group having 2 to 9 carbon atoms such as a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a t-butoxycarbonyl group, an n-pentyloxycarbonyl group, a cyclopropyloxycarbonyl group, a cyclohexylmethoxycarbonyl group and a 2-ethylhexyloxycarbonyl group;
an alkylcarbonyloxy group having 2 to 9 carbon atoms such as a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a t-butylcarbonyloxy group, an n-pentylcarbonyloxy group, a cyclopropylcarbonyloxy group, a cyclohexylmethylcarbonyloxy group and a 2-ethylhexylcarbonyloxy group;
an alkylcarbonyl group having 2 to 9 carbon atoms such as an acetyl group, a propionyl group, a butyryl group, an isobutyryl group, a valeryl group, an isovaleryl group, a 2-methylbutyl group, a pivaloyl group, a hexanoyl group, a cyclopropylcarbonyl group, a cyclohexylmethylcarbonyl group and a 2-ethylhexylcarbonyl group;
a dialkylamino group having 2 to 16 carbon atoms such as a dimethylamino group, a diethylamino group, a dipropylamino group, a diisopropylamino group, a dibutylamino group, a diisobutylamino group, a di-t-butylamino group, a dihexylamino group, an ethylmethylamino group and a butylpentylamino group; and the like can be cited.

Among these, an unsubstituted straight chain alkyl group having 1 to 6 carbon atoms, or an unsubstituted branched chain alkyl group having 3 to 8 carbon atoms are preferable for $R_2$. When unsubstituted straight chain alkyl groups are used, the number of carbon atoms is generally set to range from 1 to 6 inclusive. The number of carbon atoms is preferably set to 5 or less, more preferably set to 4 or less. Meanwhile, when unsubstituted branched chain alkyl groups are used, the number of carbon atoms is set to range from 3 to 8 inclusive. The number of carbon atoms is preferably set to 7 or less, more preferably set to 6 or less, further preferably set to 5 or less, and particularly preferably set to 4 or less. A methyl group, an ethyl group, a propyl group, an isopropyl group and an isopropyl group are particularly preferable for $R_2$.

Each of $R_6$, $R_7$, $R_8$ and $R_9$ independently represents a hydrogen atom or an alkyl group having 1 to 2 carbon atoms. Use of hydrogen atoms and alkyl groups having 1 to 2 carbon atoms is preferable because it makes it easy to set the OD2/OD1 value to a predetermined value. In alkyl groups having 1 to 2 carbon atoms, a hydrogen atom bonded to a carbon atom may be substituted with other substituents (such as a halogen atom). However, the alkyl groups are preferably unsubstituted alkyl groups. For alkyl groups having 1 to 2 carbon atoms, a methyl group and an ethyl group can be cited. In light of simplicity of synthesis and spatial structure, a hydrogen atom is the most preferable for $R_6$, $R_7$, $R_8$ and $R_9$.

The molecular weight of the azo dye compounds represented by the general formula (1) is generally 2000 or less. Among others, the azo dye compounds with the molecular weight of 1000 or less are preferable because they lead to dyes that exhibit increased solubility in solvents and are excellent in light-resistance, weather-resistance and high reflectivity. Among the azo dye compounds represented by the general formula (1), compounds shown in the following (formulae 3 to 30) can be cited as the specific examples.

[formulae 3]

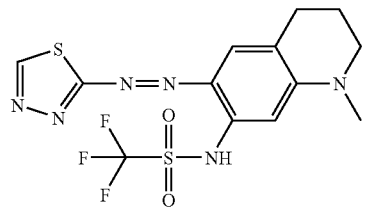

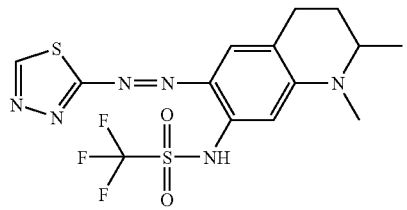

-continued

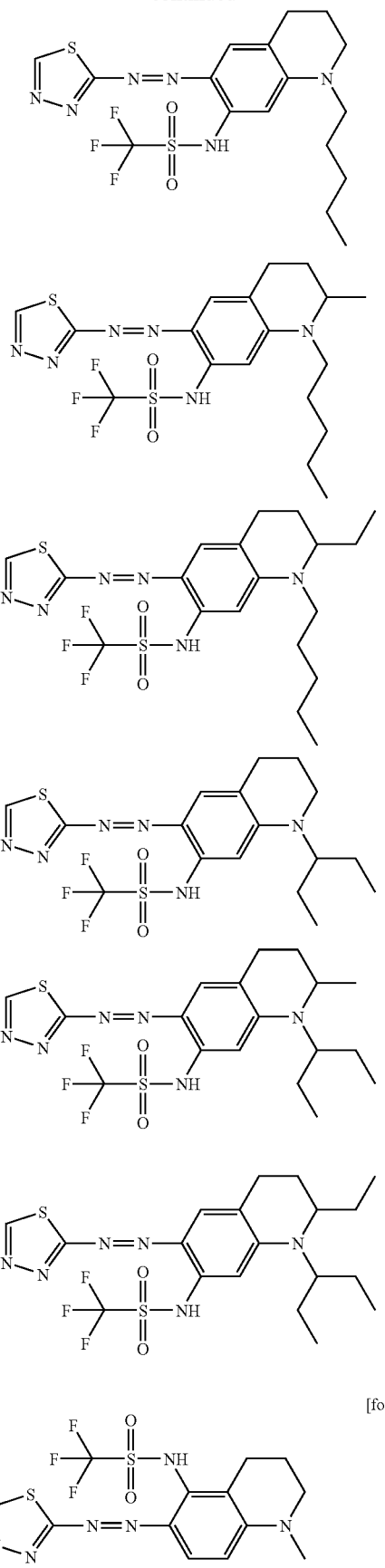
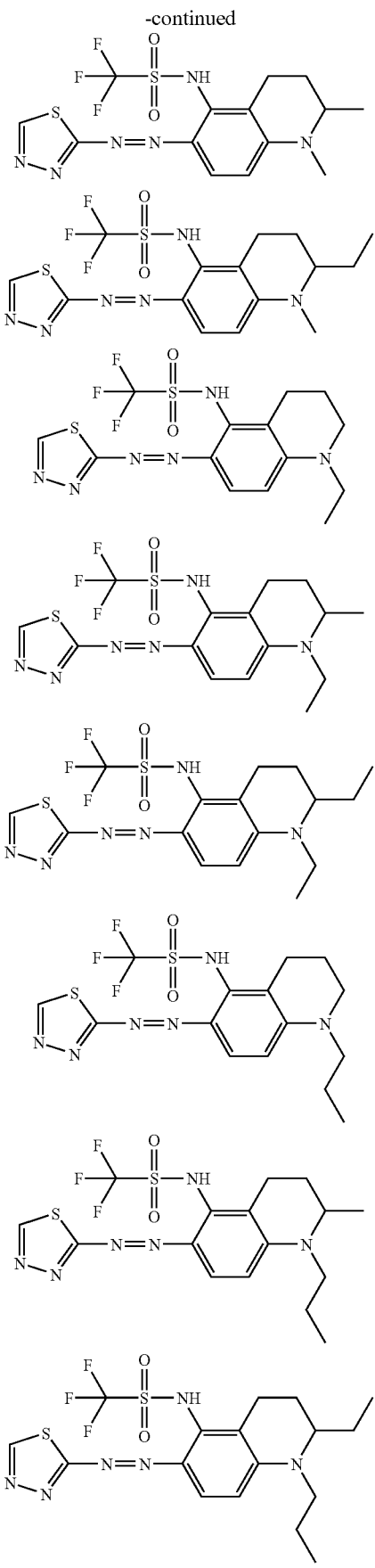
[formulae 4]

-continued
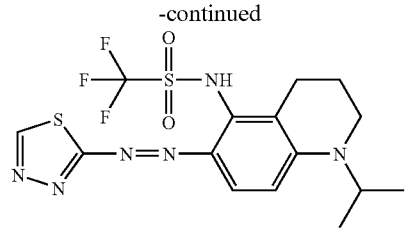
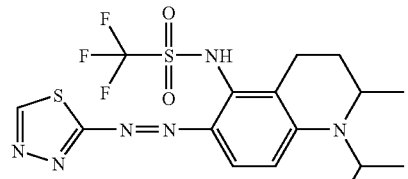
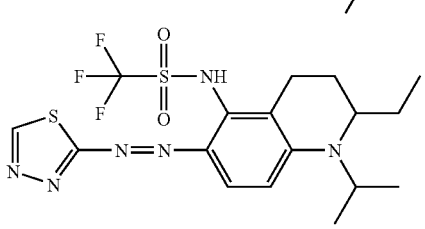
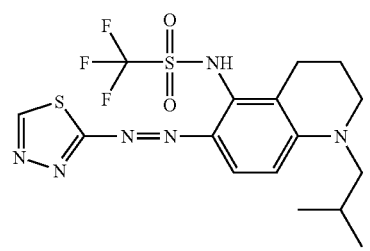
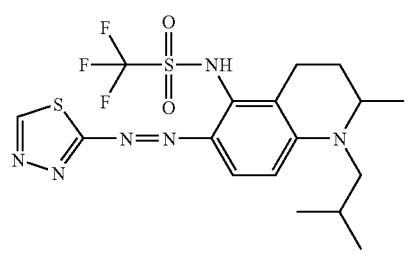
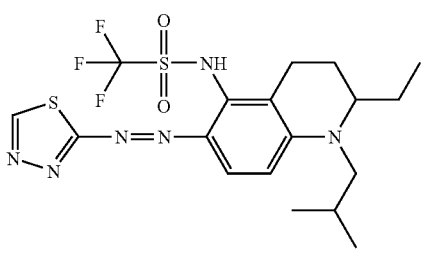
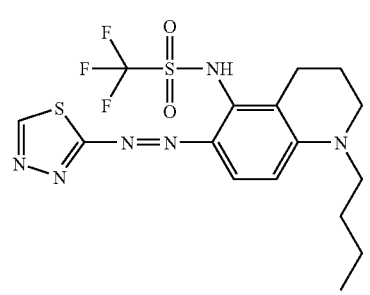
-continued
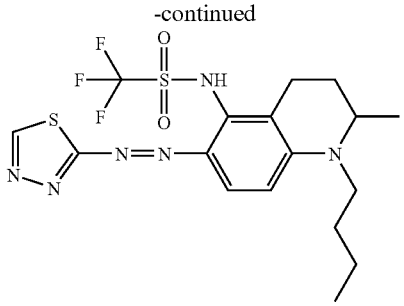
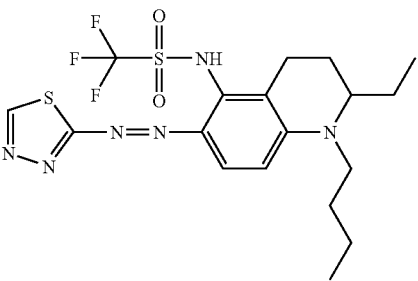
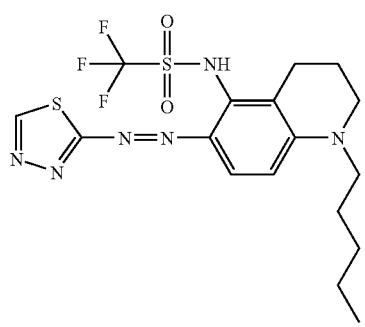
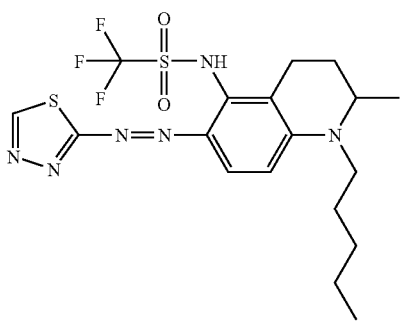
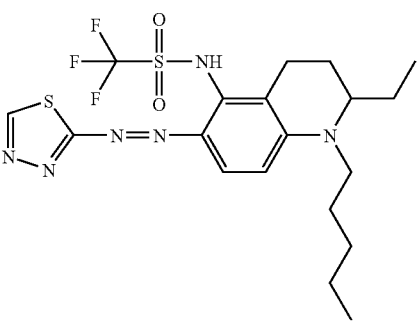

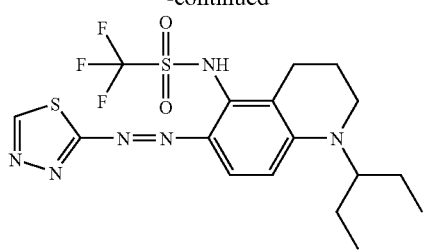
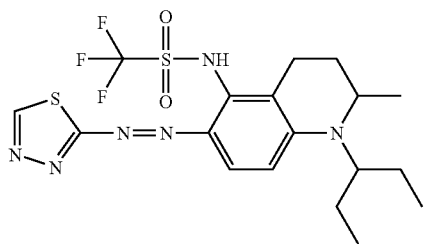
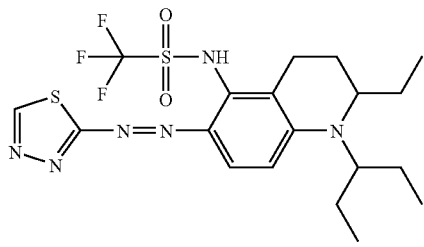
[formulae 5]
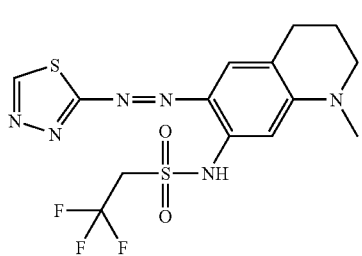
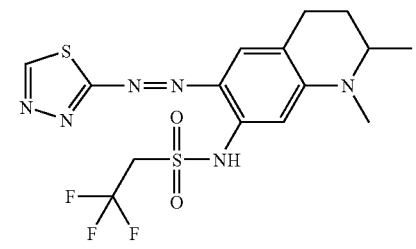
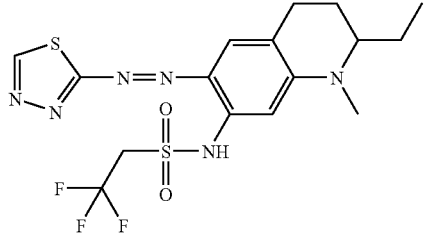
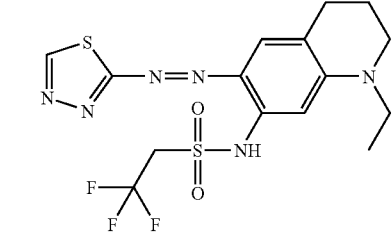
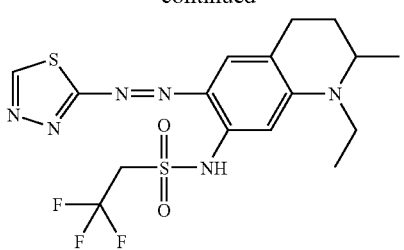
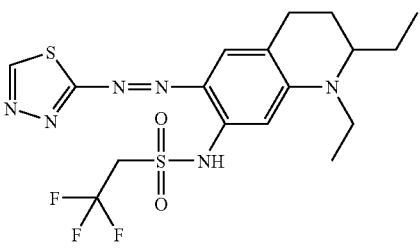
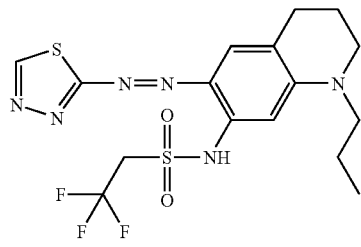
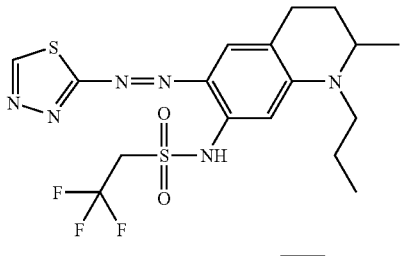
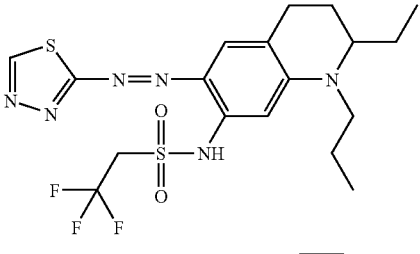
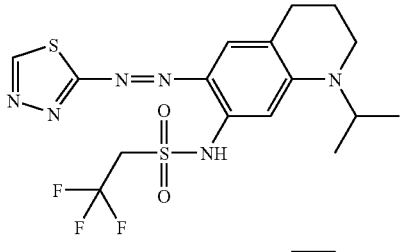
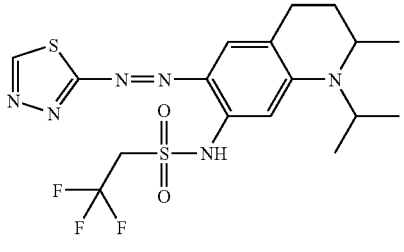

21
-continued
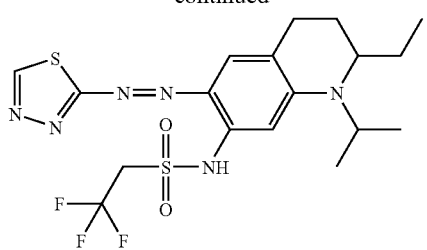
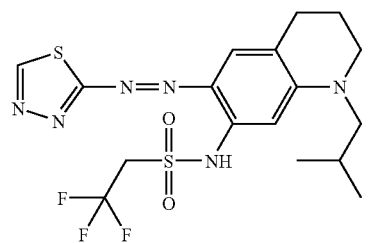
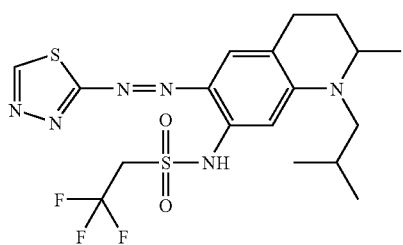
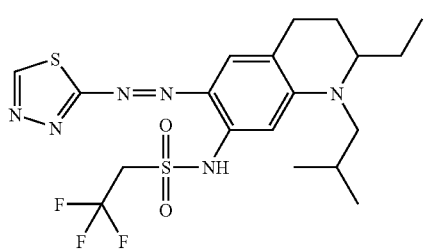
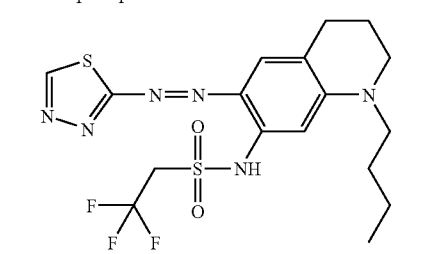
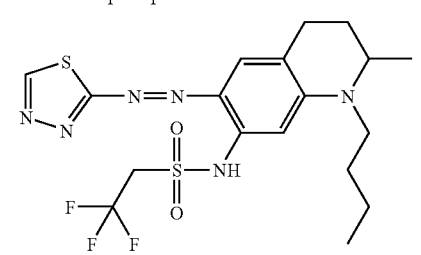
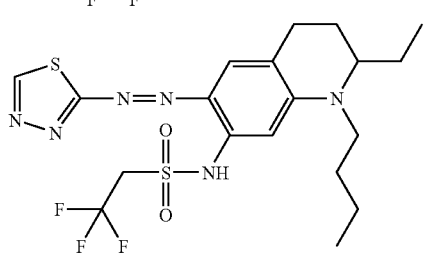
22
-continued
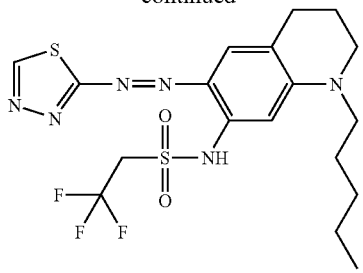
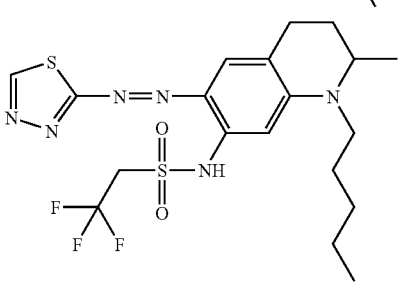
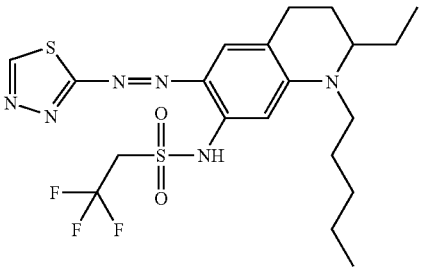
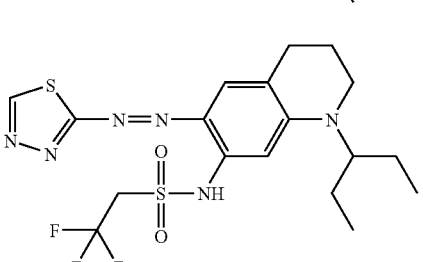
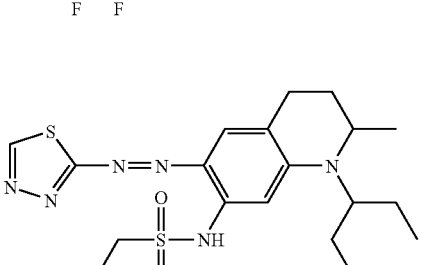
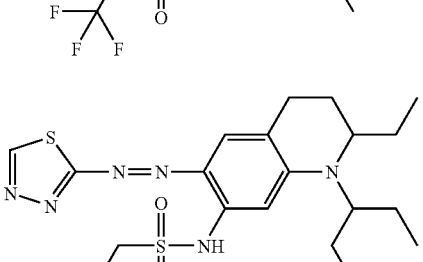

[formulae 6]
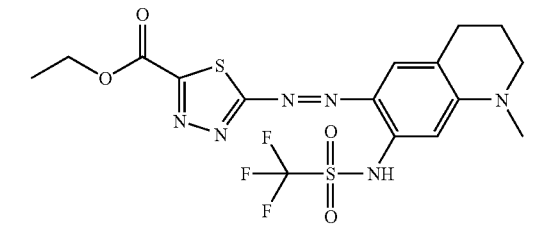
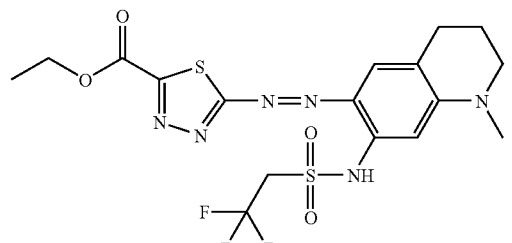
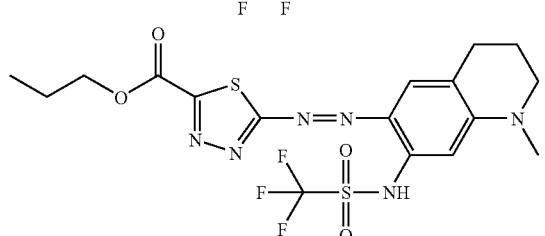
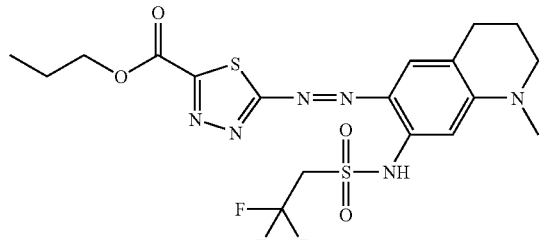
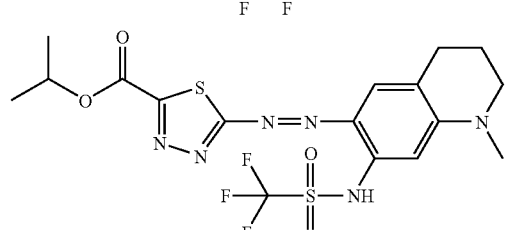
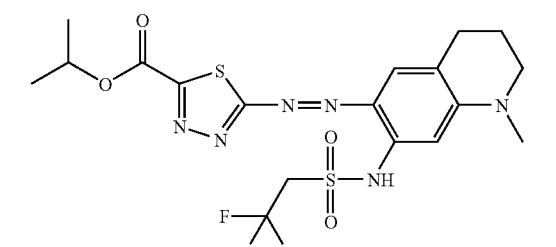
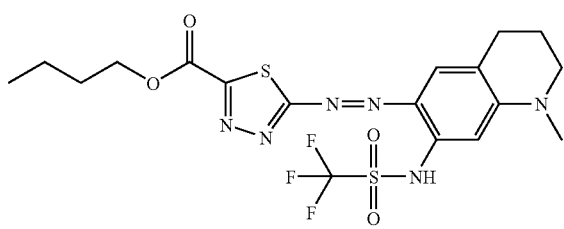
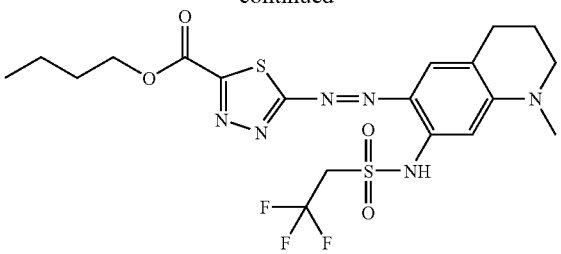
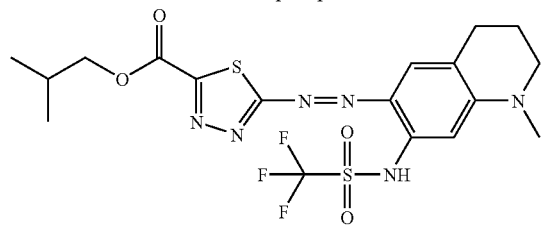
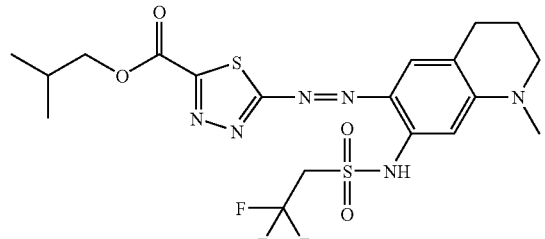
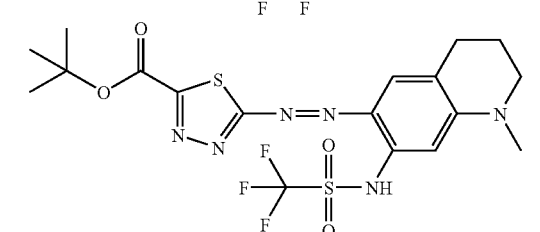
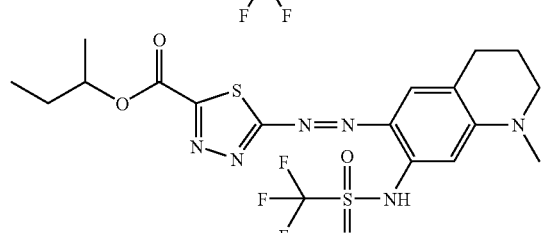
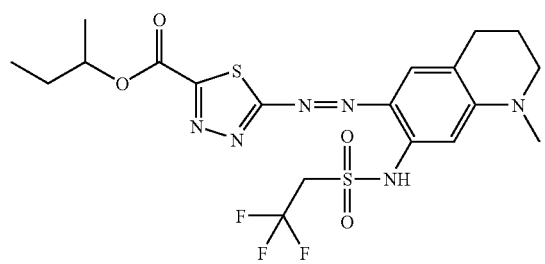

-continued
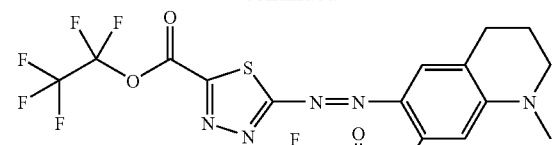
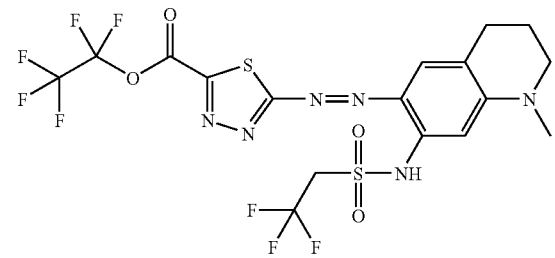
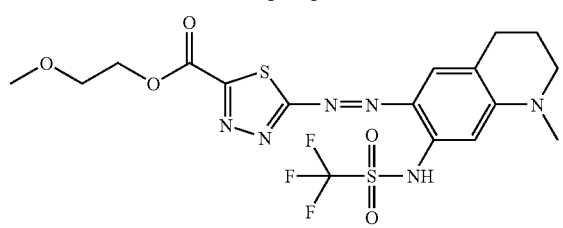
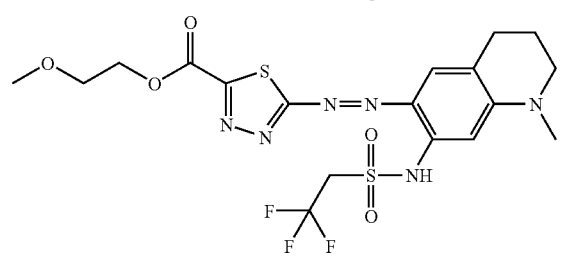
[formulae 7]
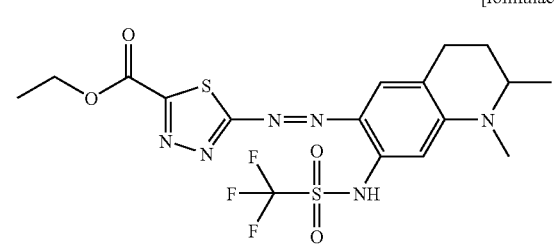
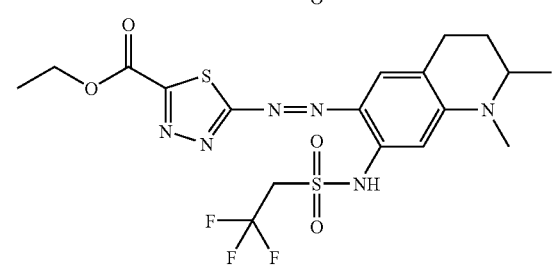
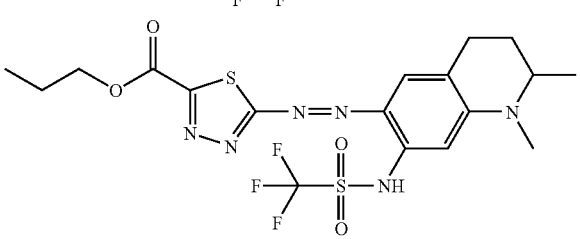
-continued
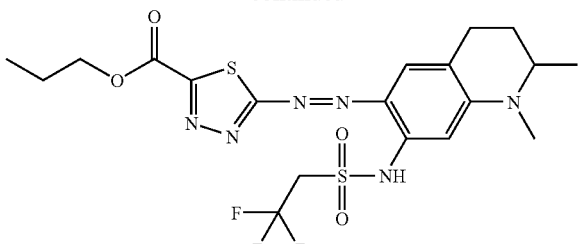
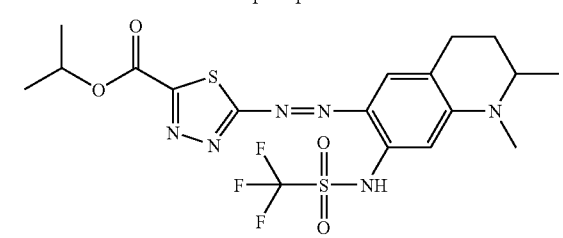
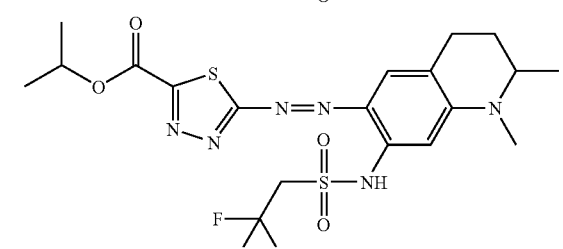
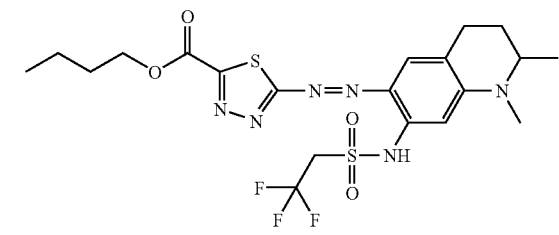
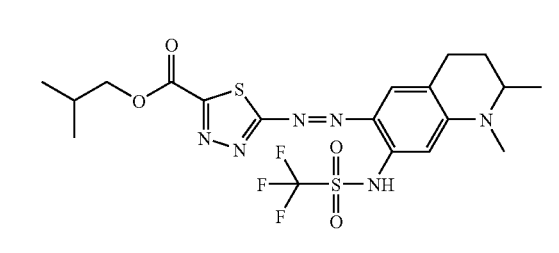
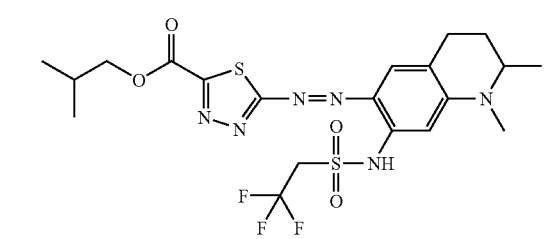

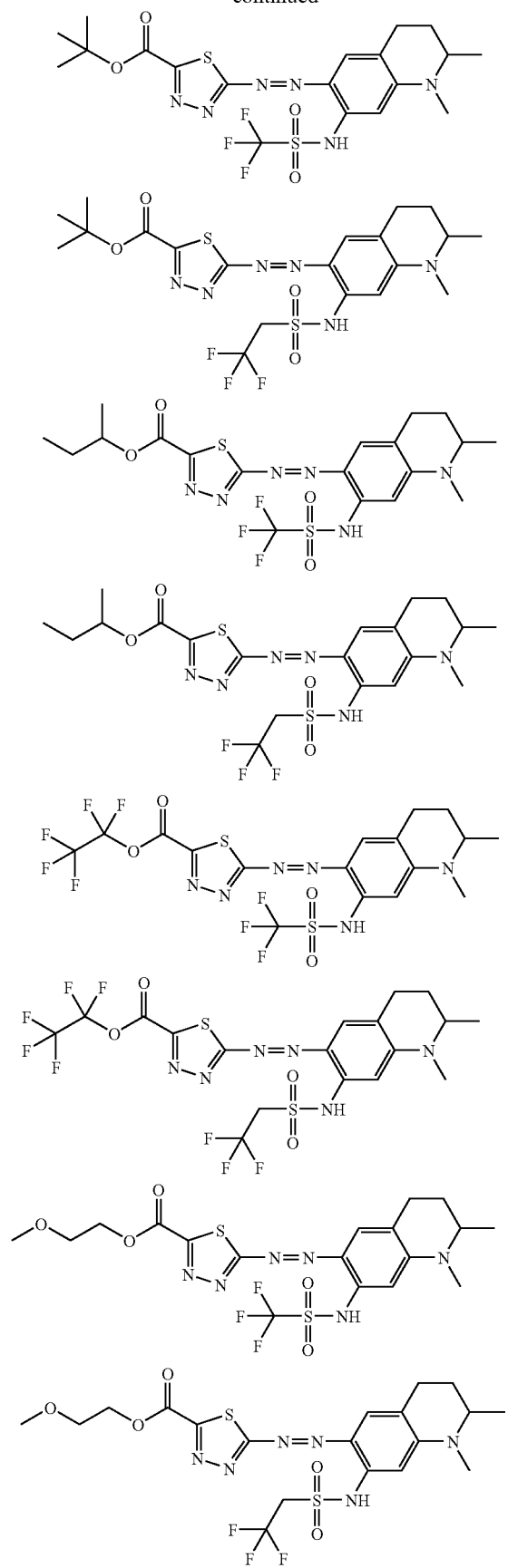
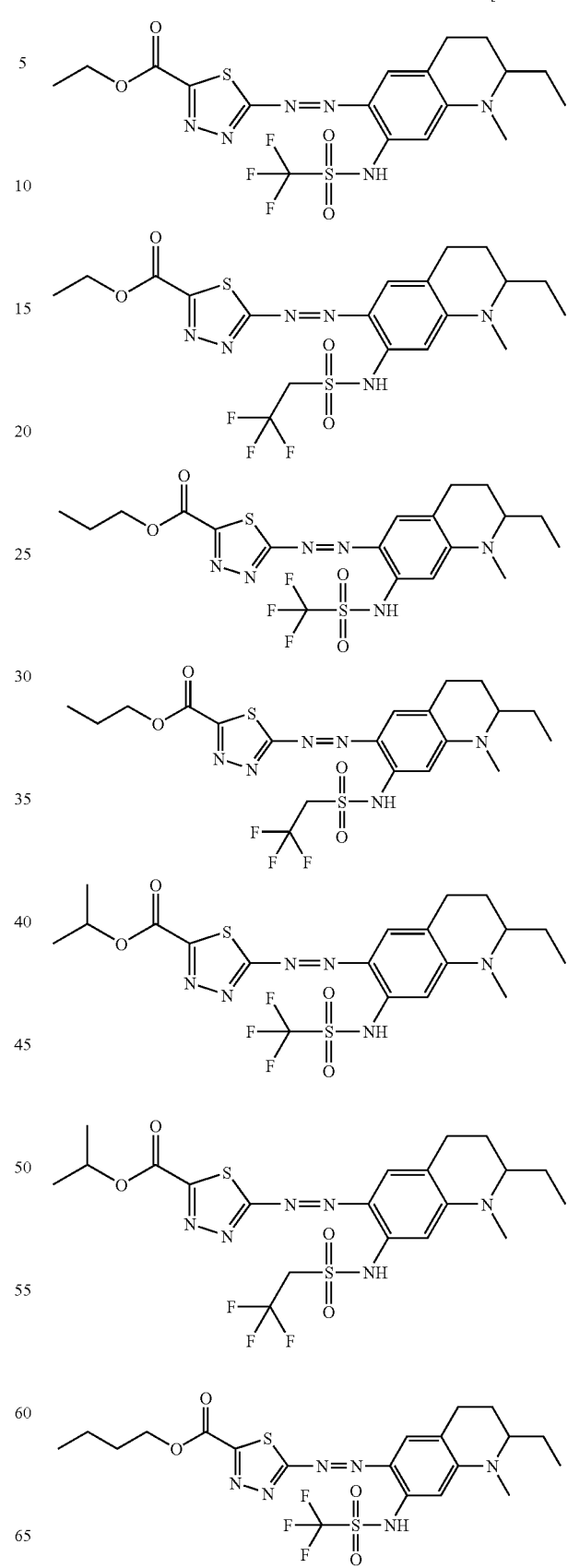

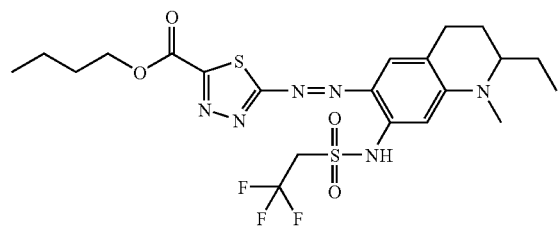
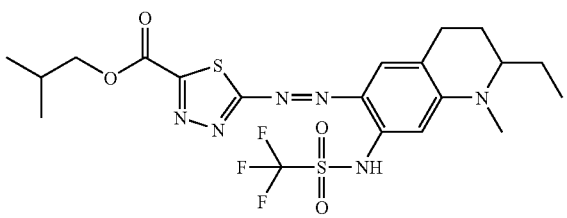
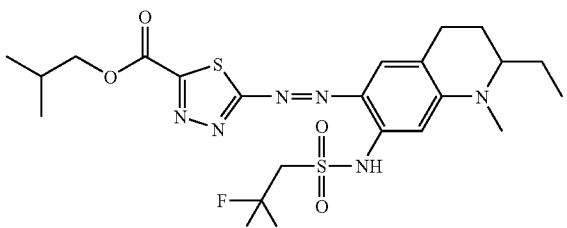
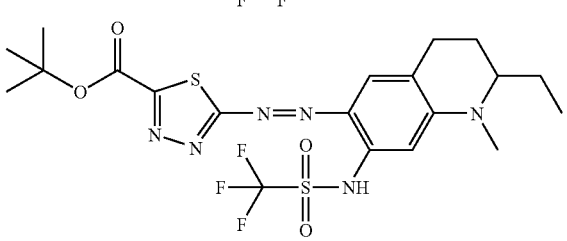
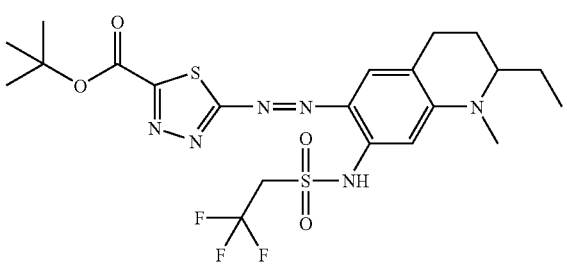
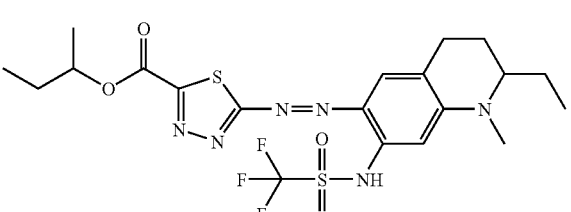
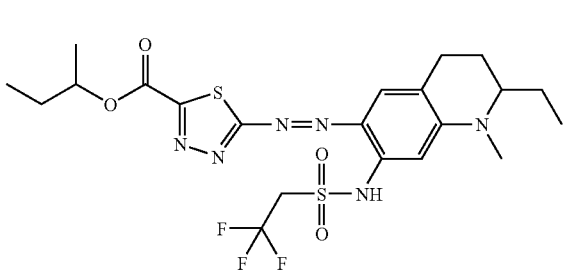
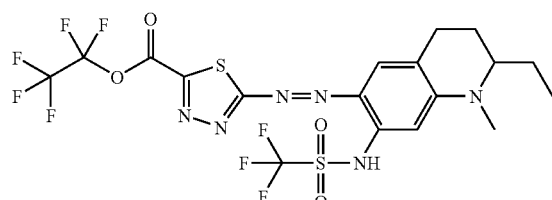
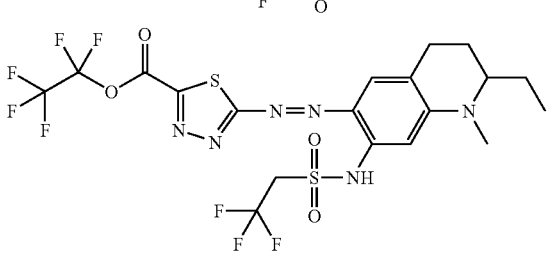
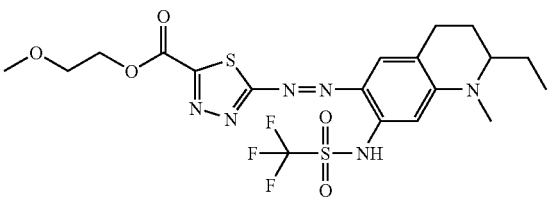
[formulae 9]
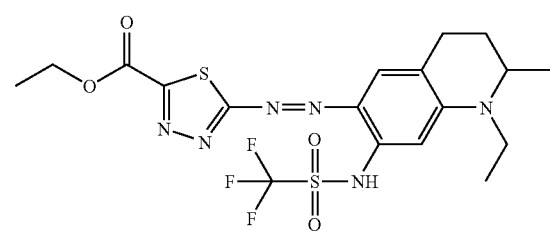
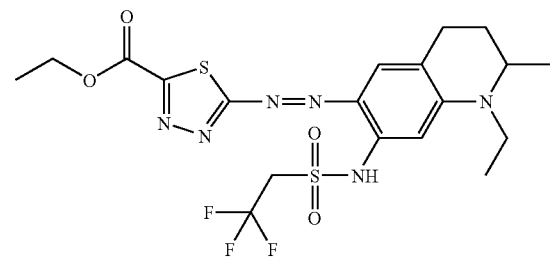

31
-continued
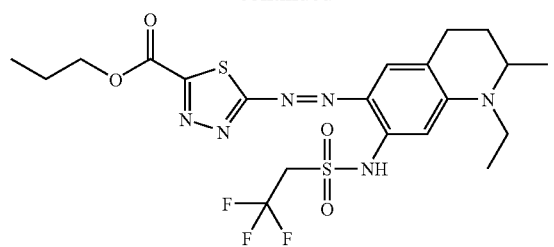
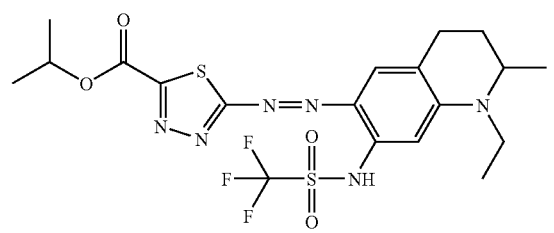
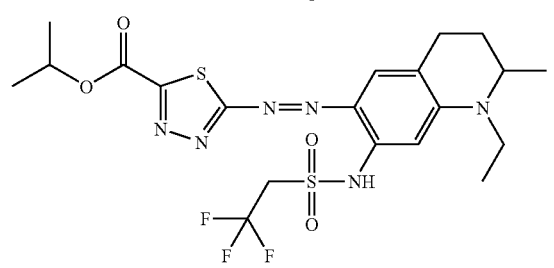
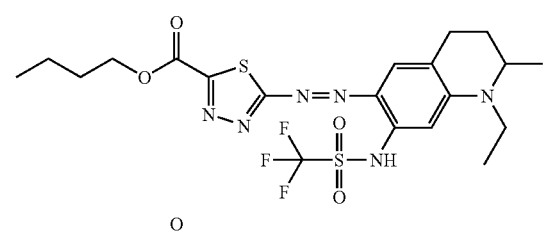
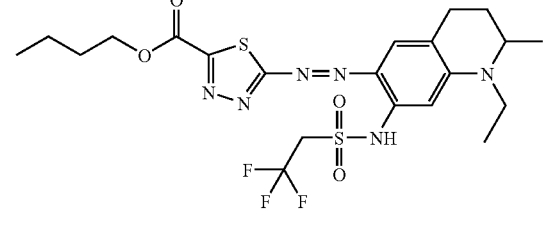
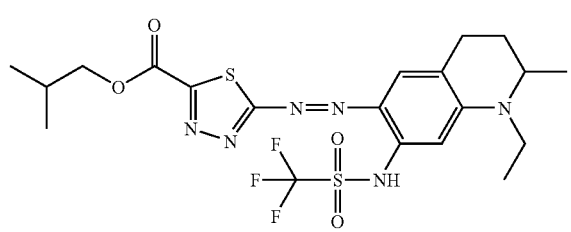
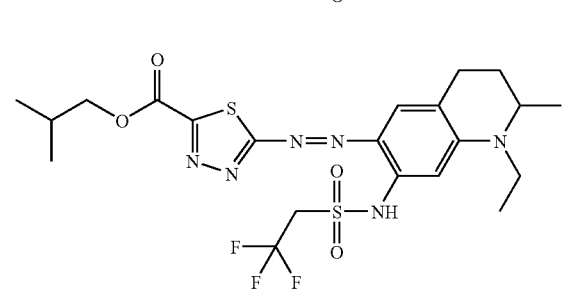
32
-continued
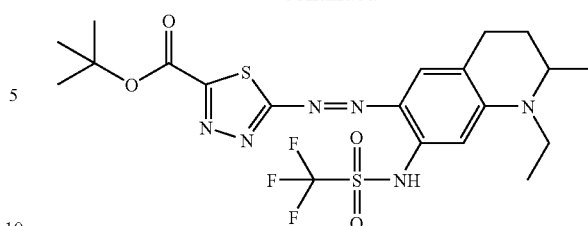
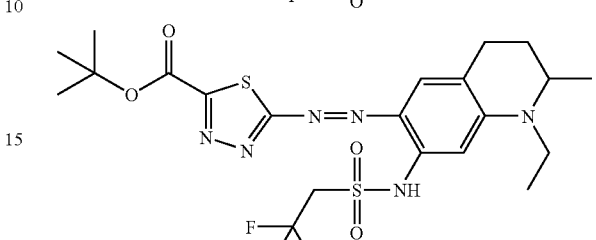
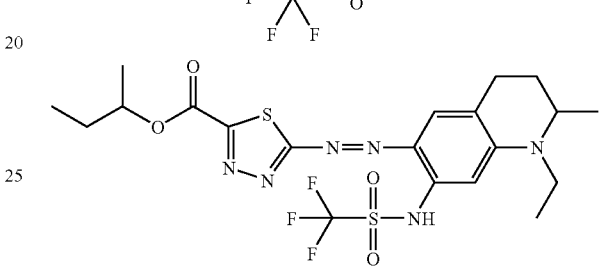
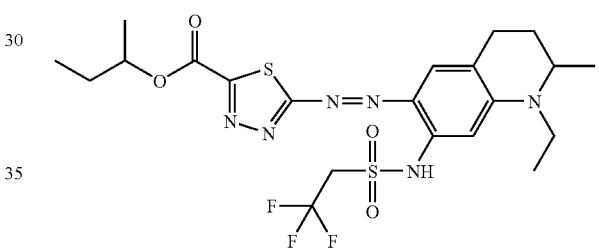
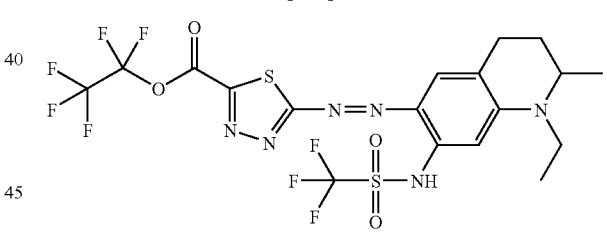
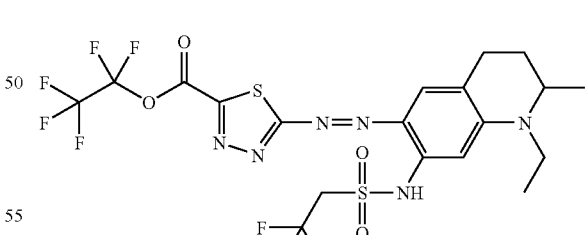
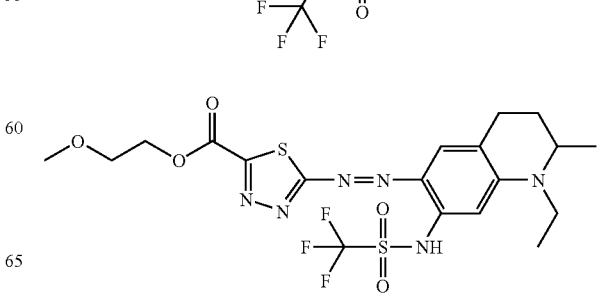

33
-continued
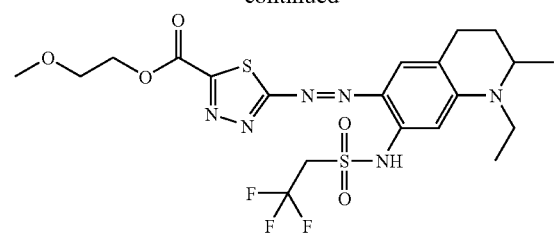
[formulae 10]
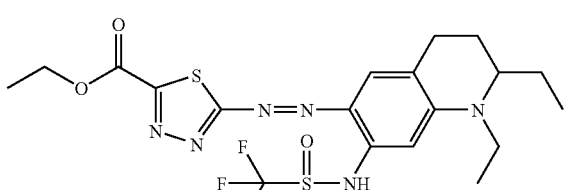
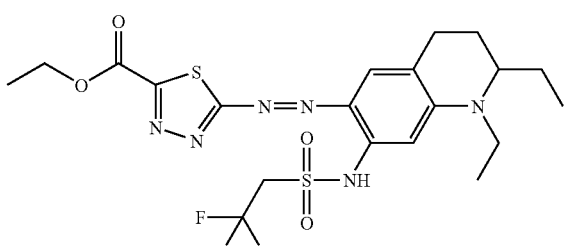
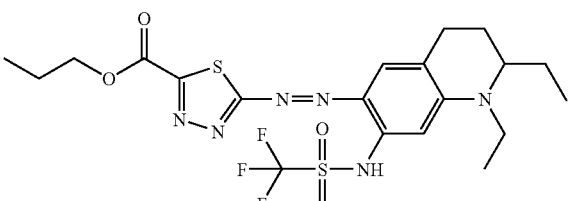
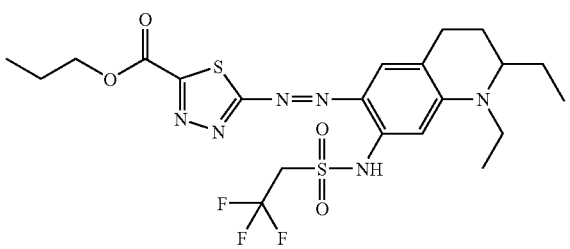
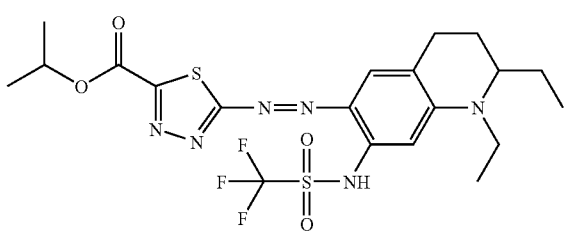
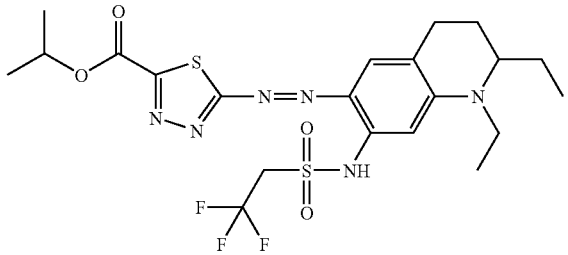
34
-continued
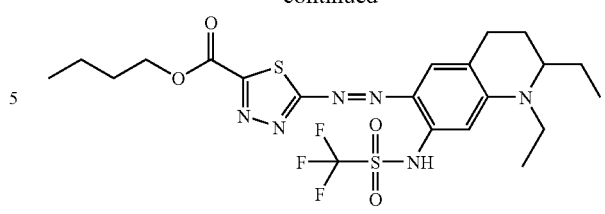
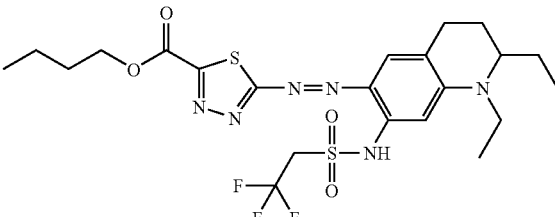
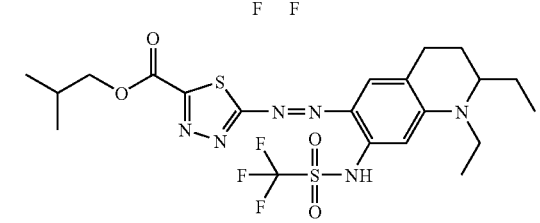
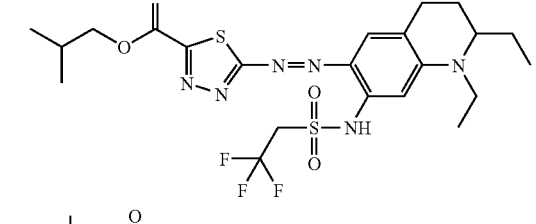
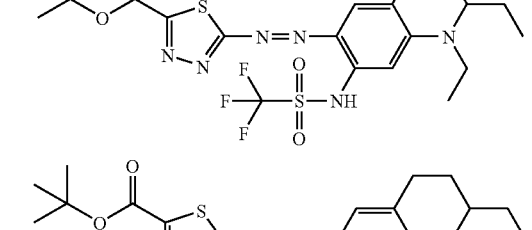
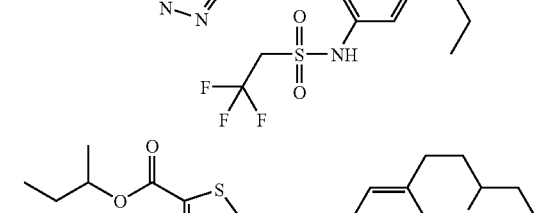
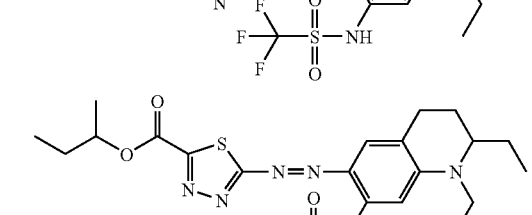

35
-continued
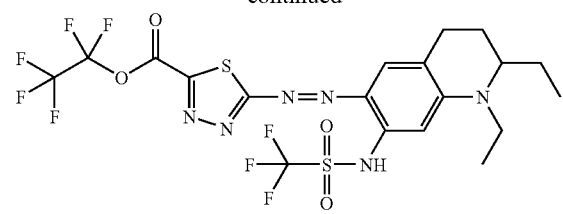
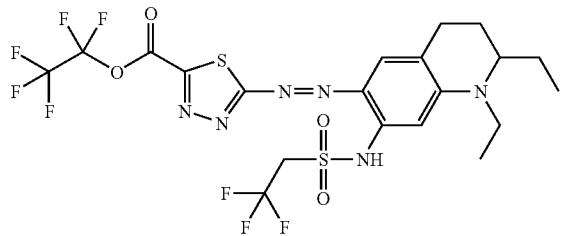
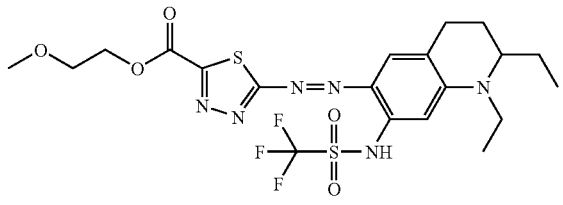
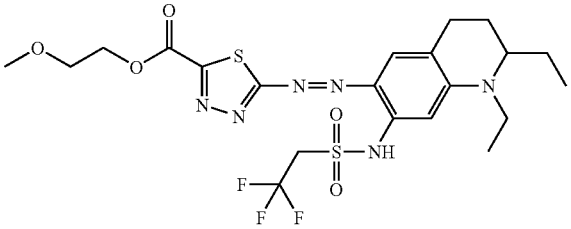
[formulae 11]
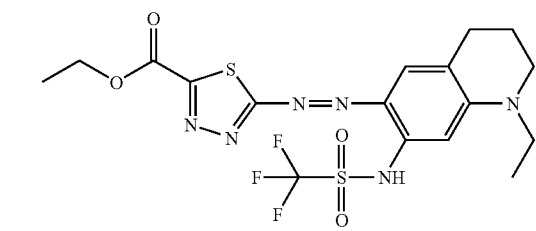
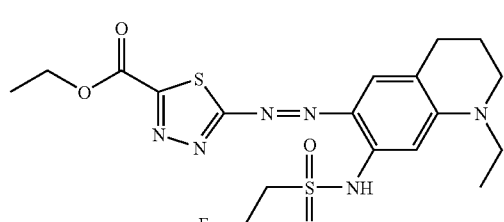
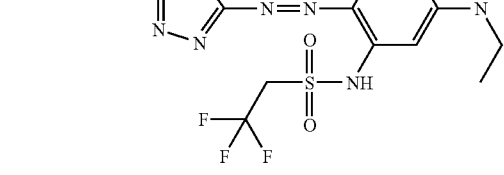
36
-continued
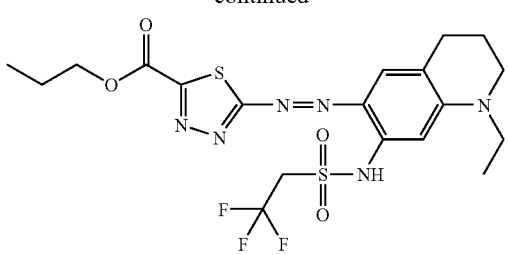
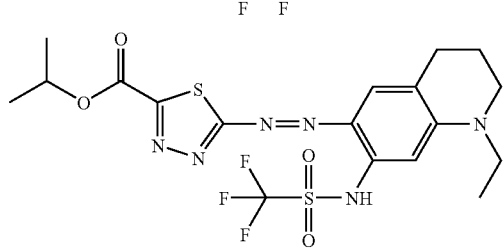
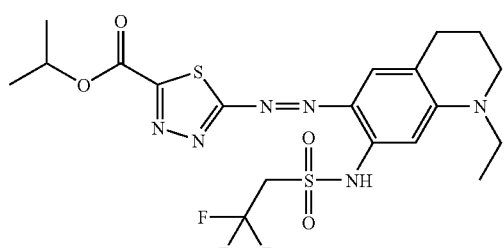
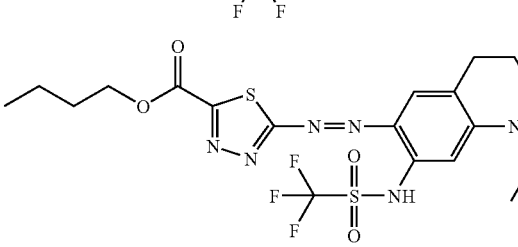

37
-continued
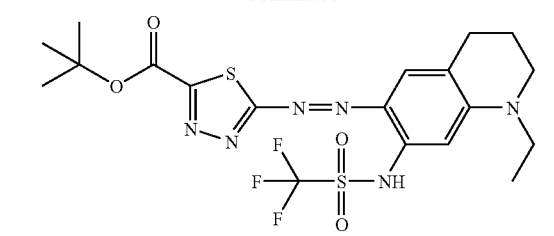
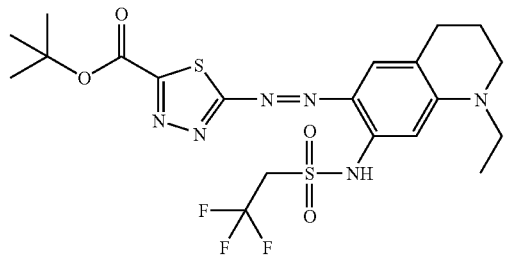
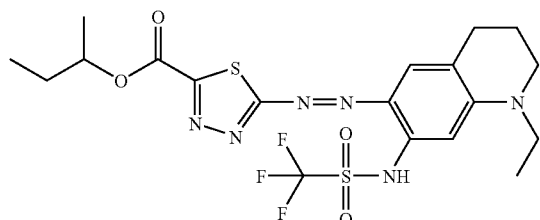
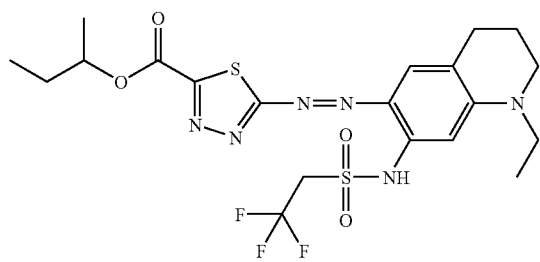
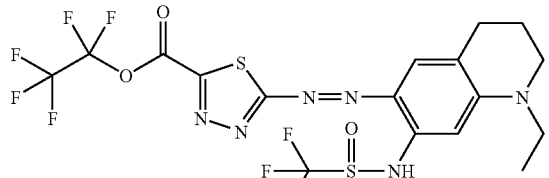
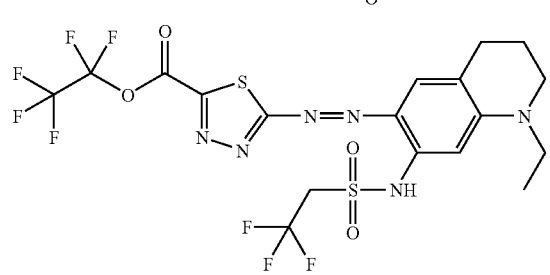
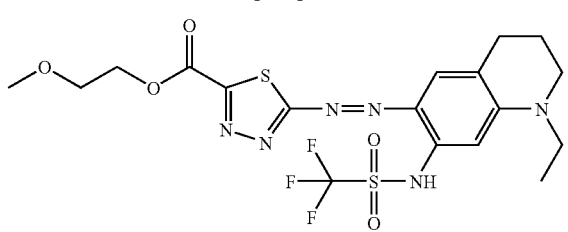
38
-continued
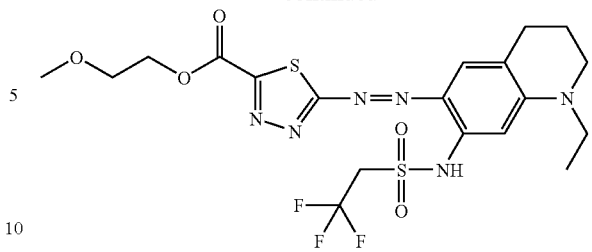
[formulae 12]
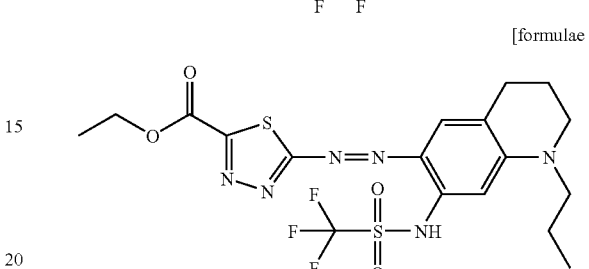
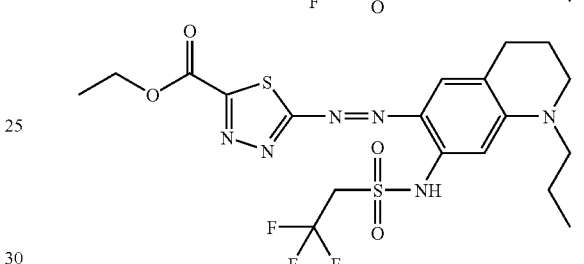
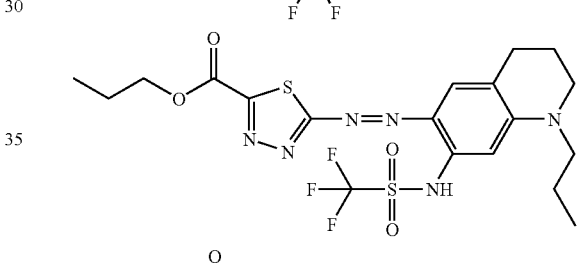
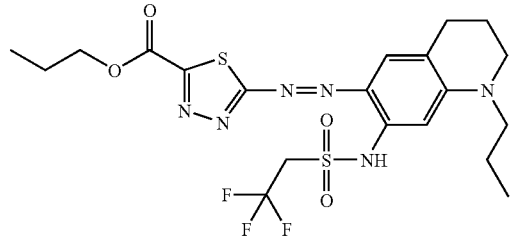
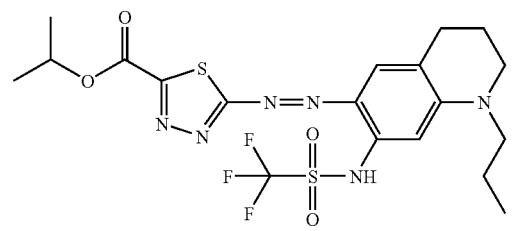
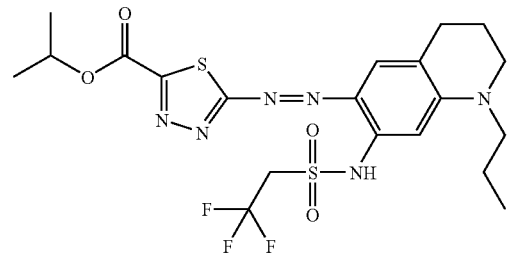

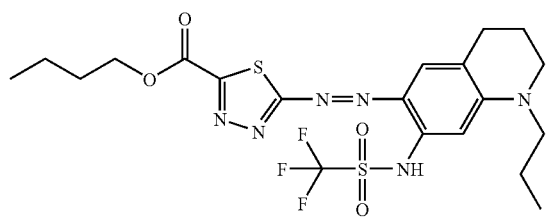
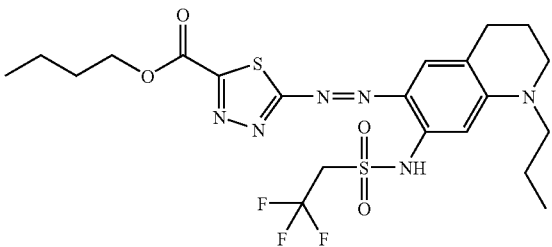
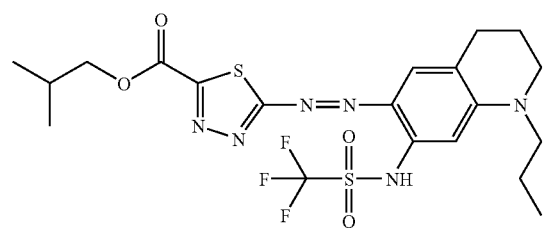
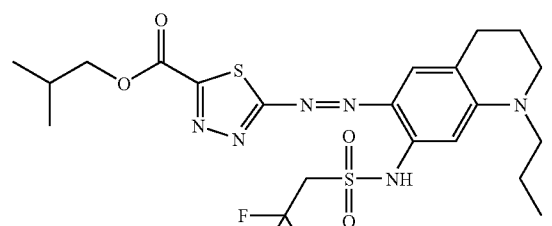
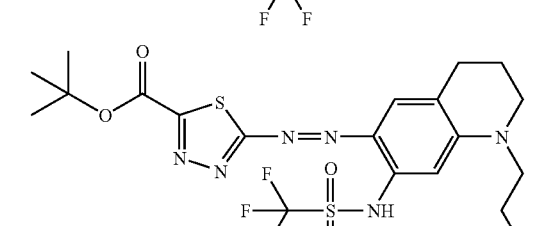
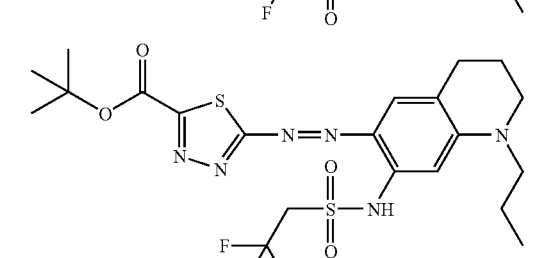
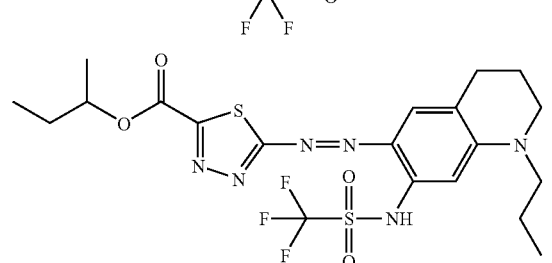
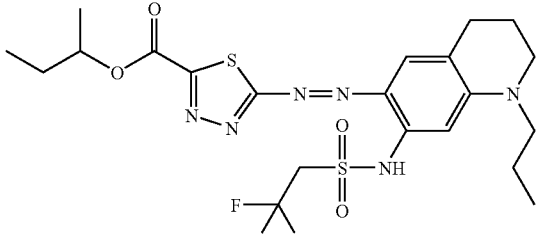
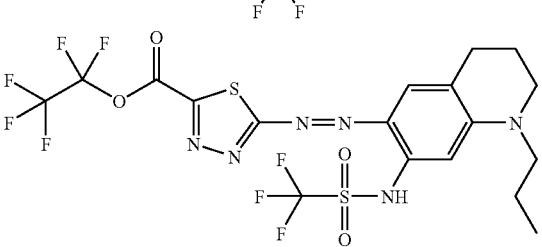
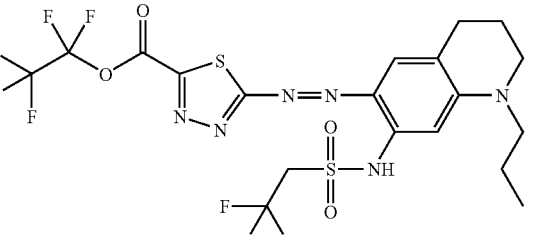
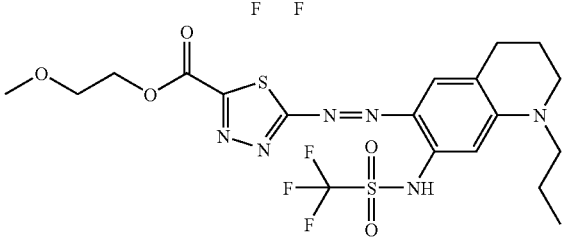
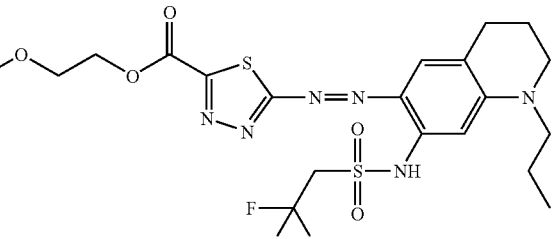
[formulae 13]
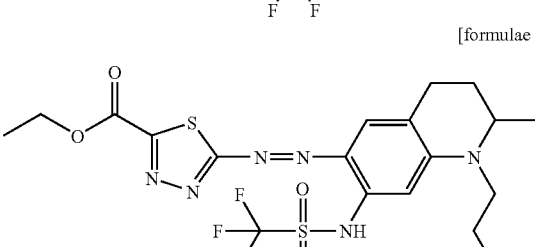
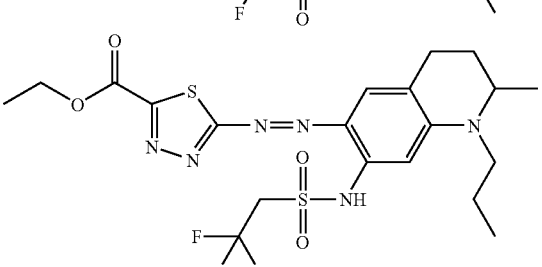

41
-continued
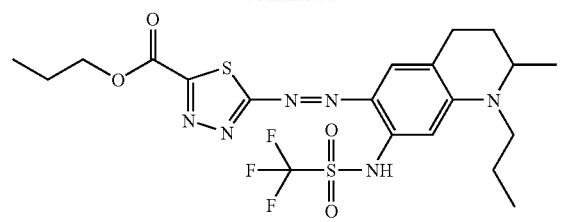
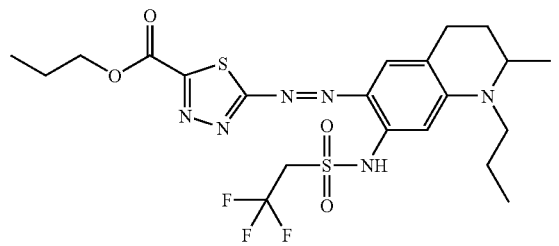
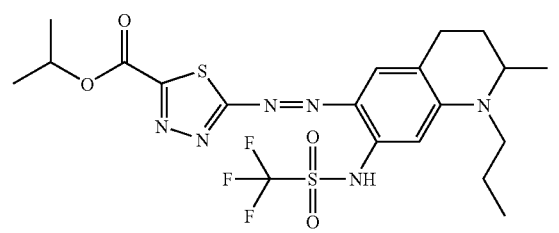
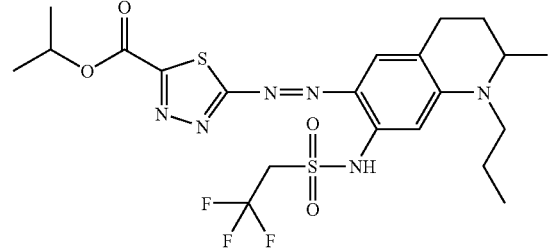
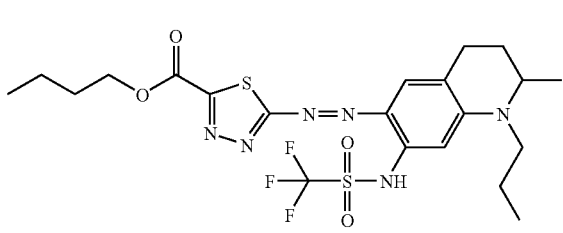
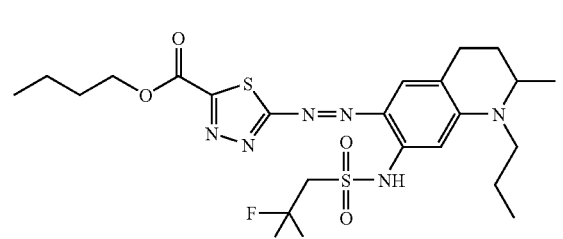
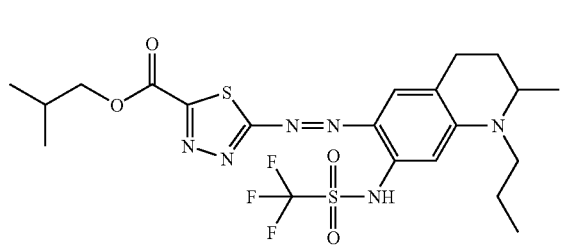
42
-continued
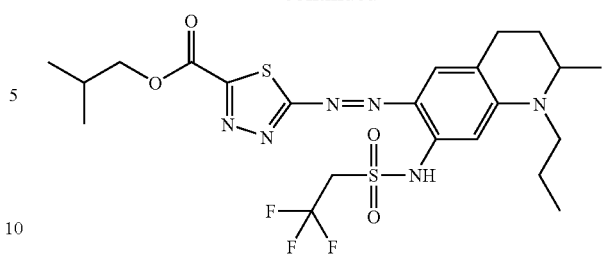
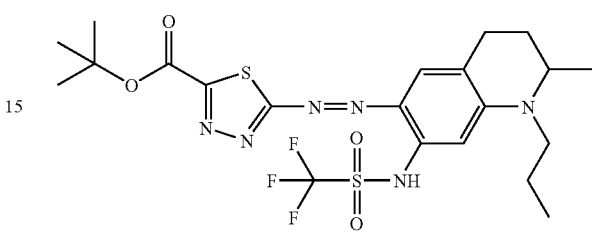
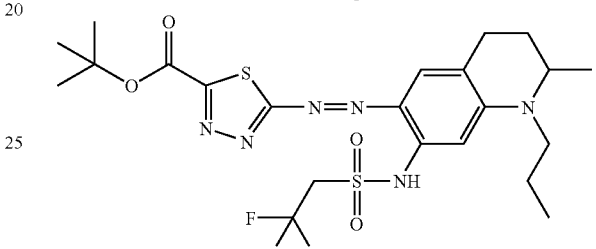
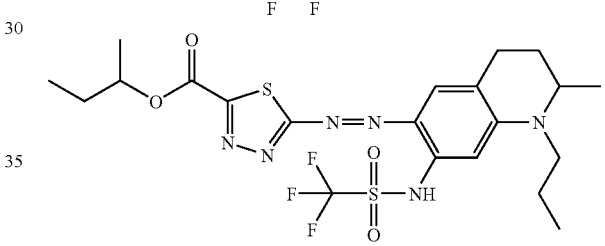
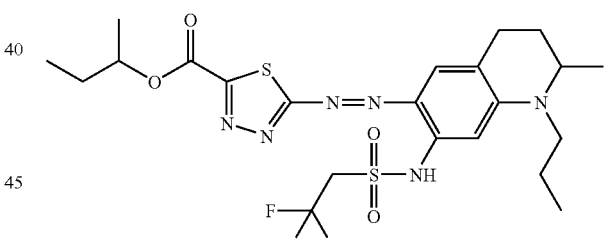
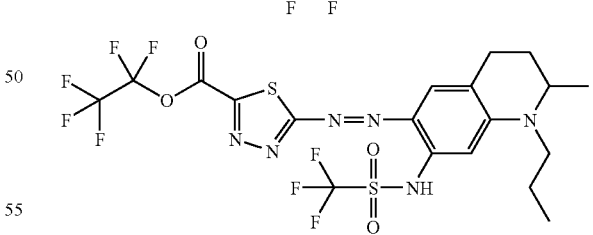
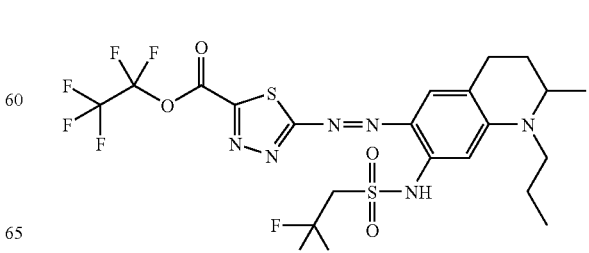

-continued
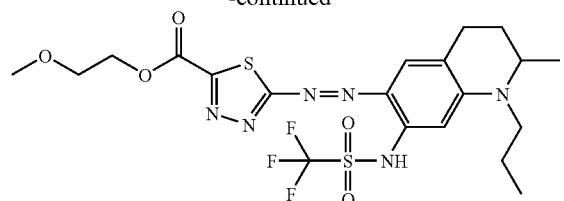
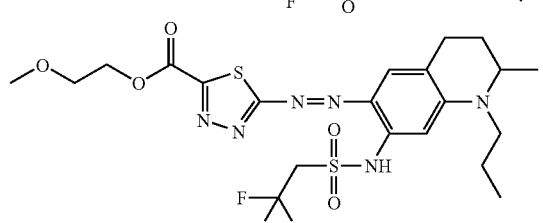
[formulae 14]
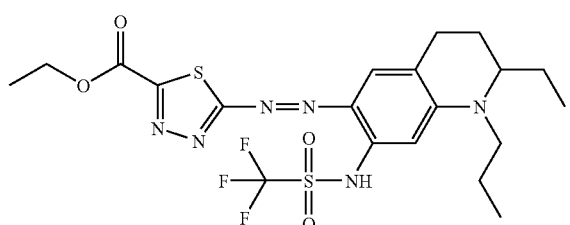
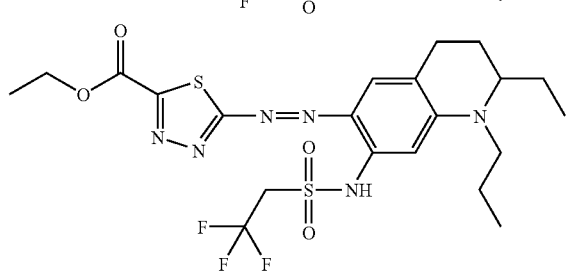
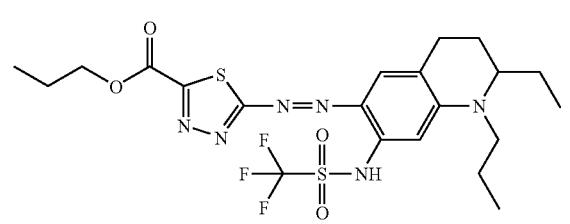
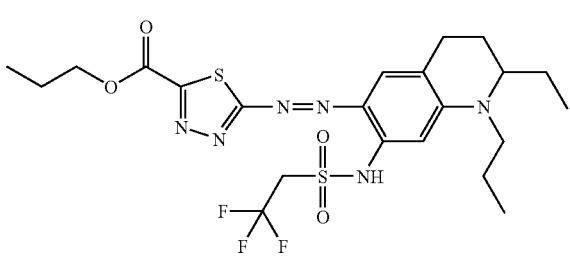
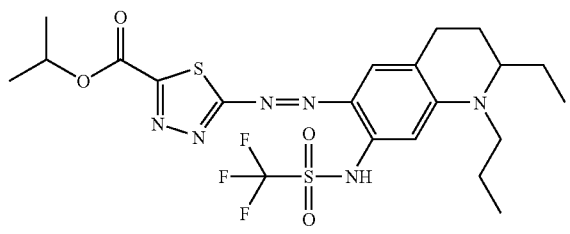
-continued
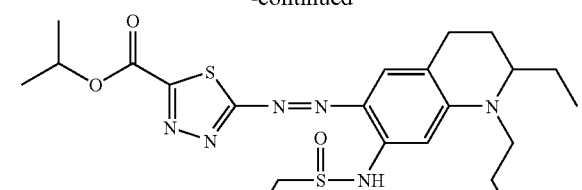
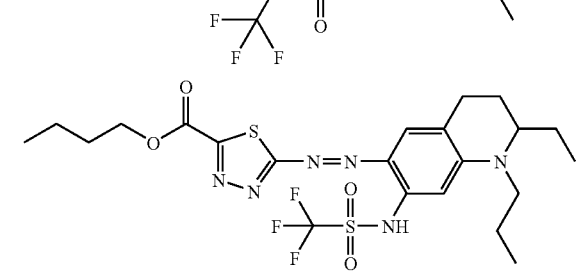
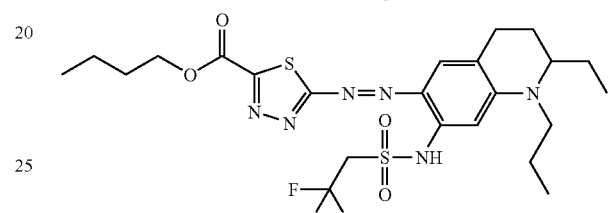
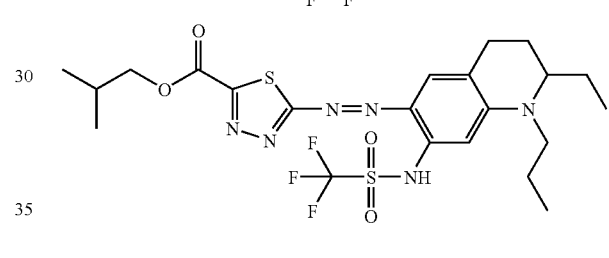
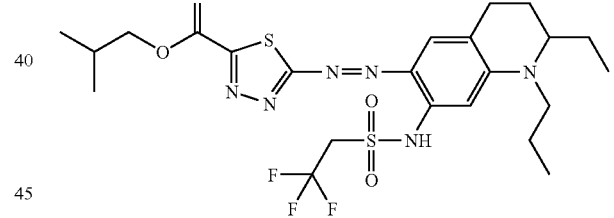
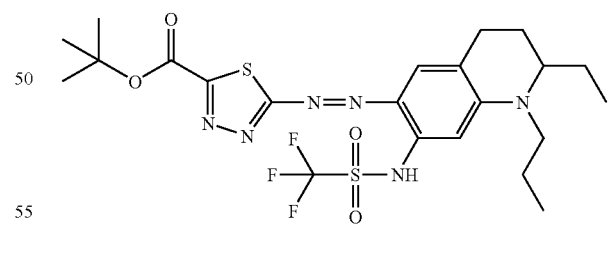
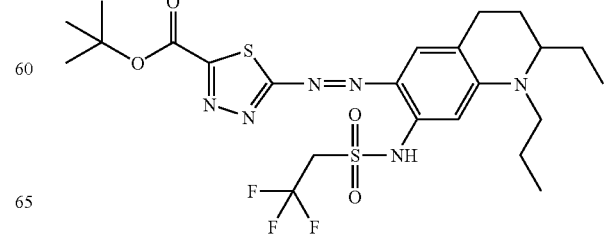

45
-continued
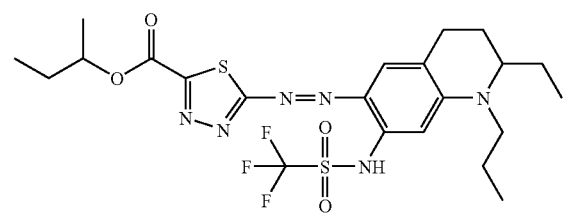
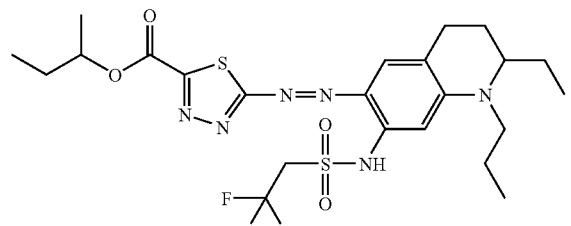
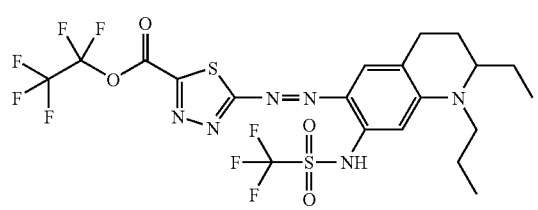
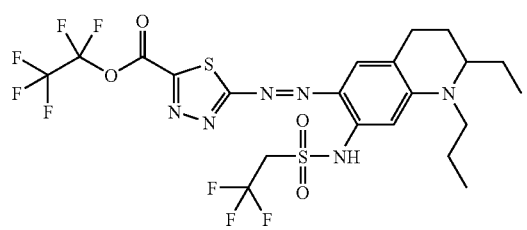
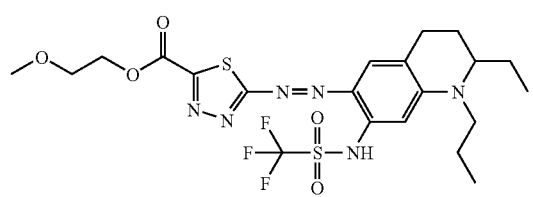
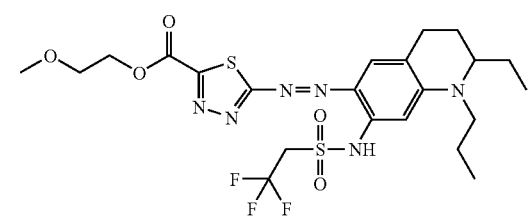
[formulae 15]
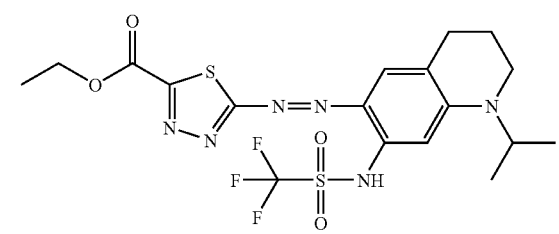
46
-continued
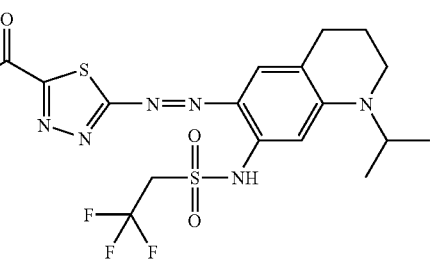
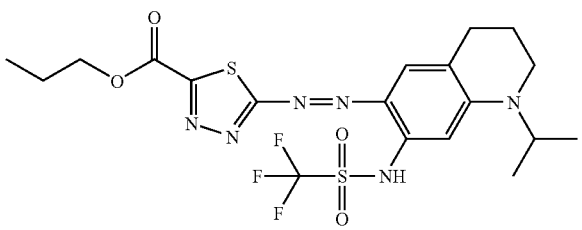
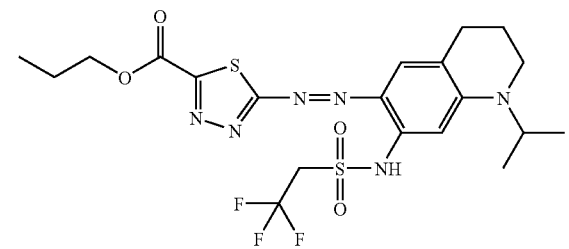
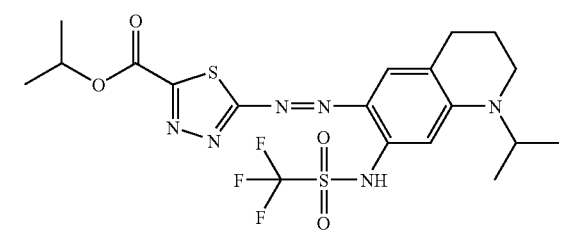
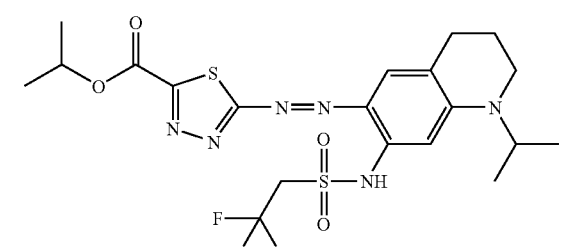
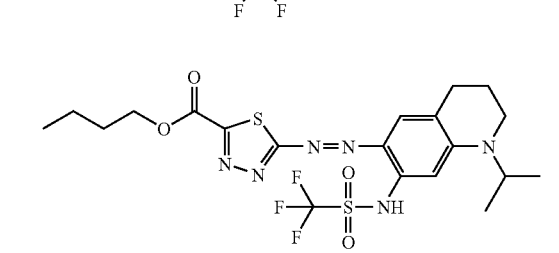
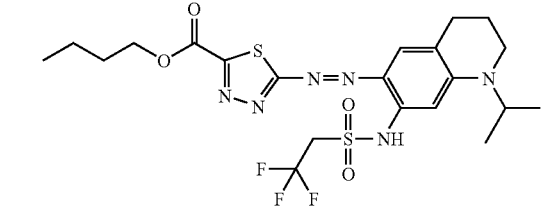

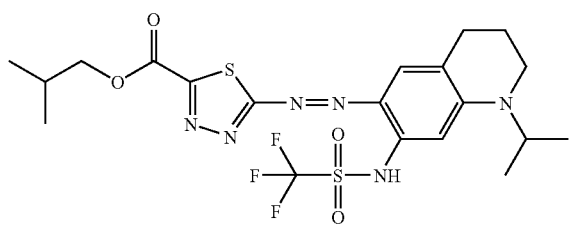
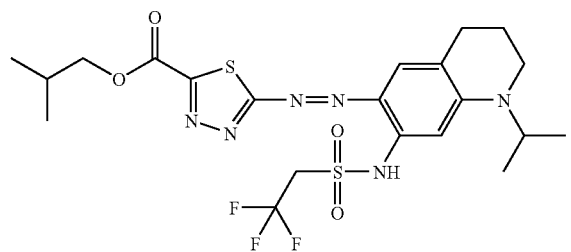
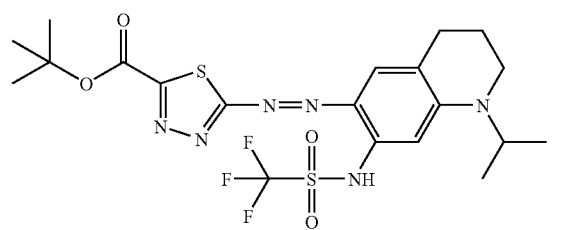
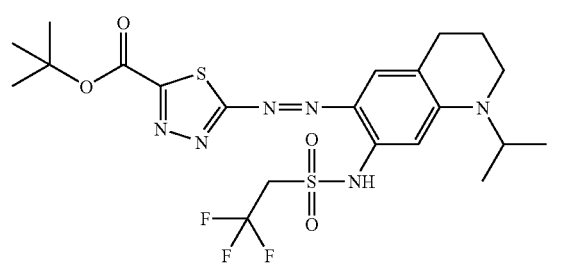
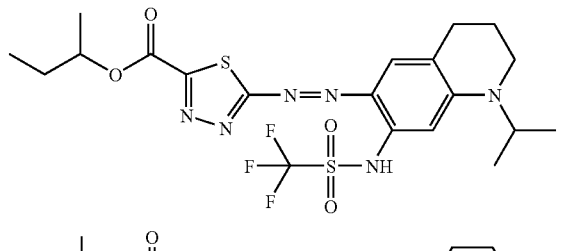
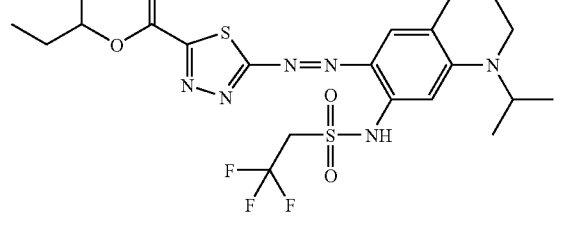
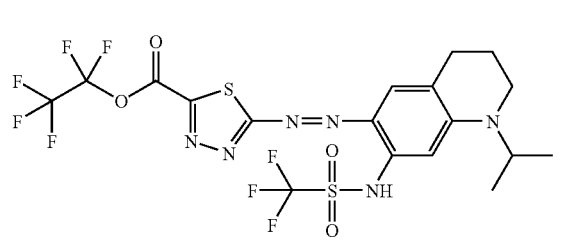
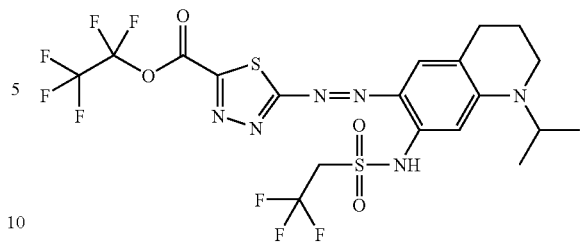
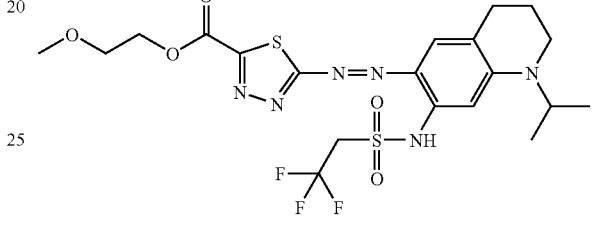
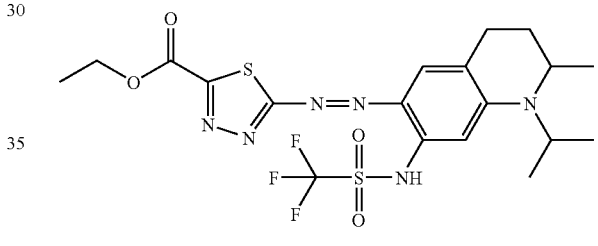
[formulae 16]
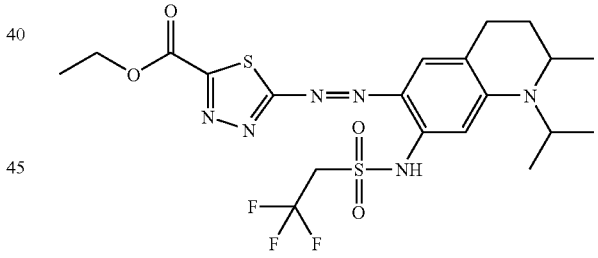
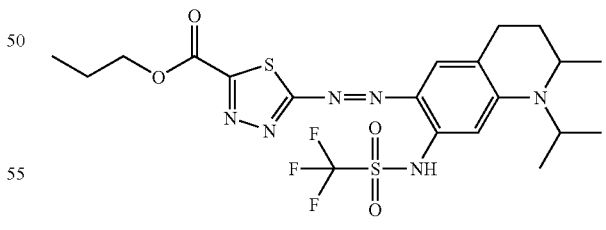
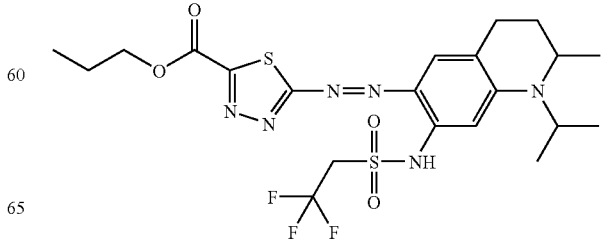

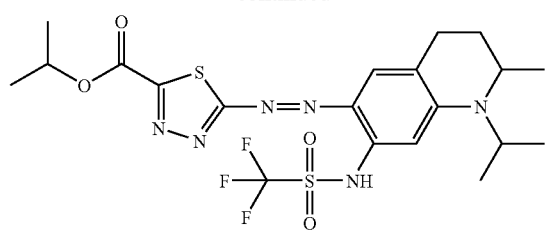
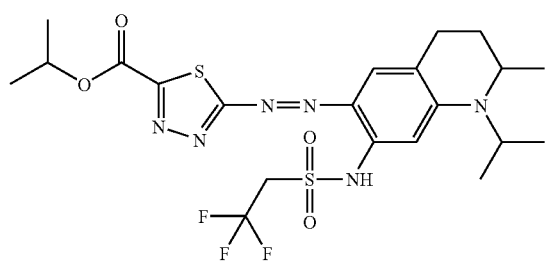
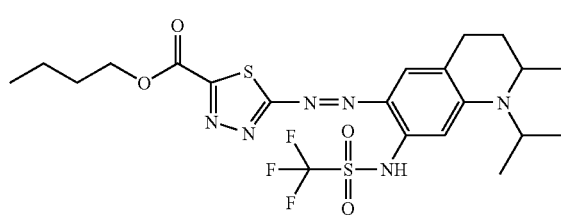
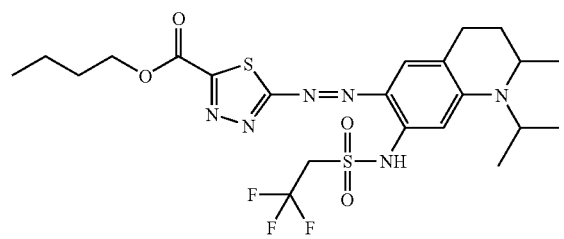
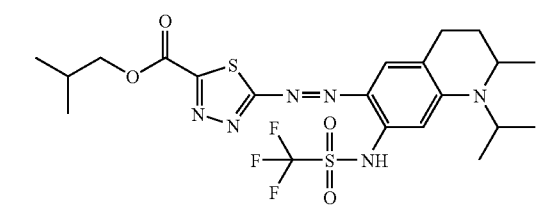
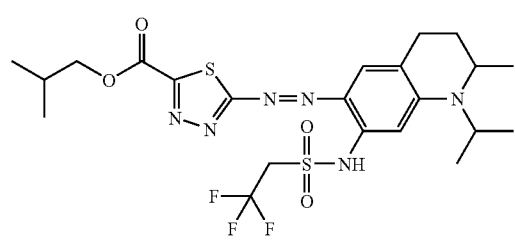
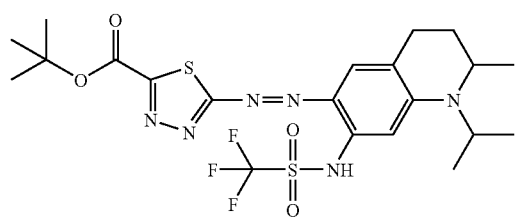
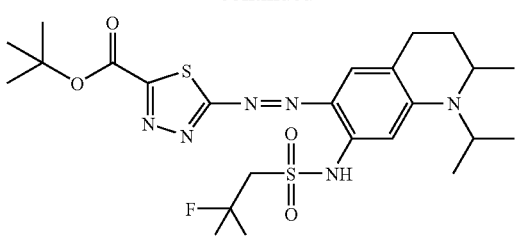
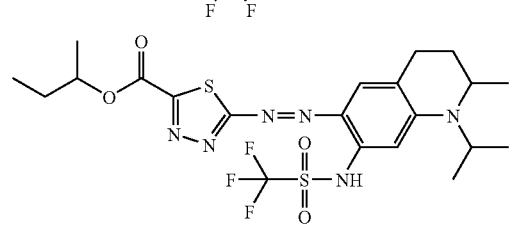
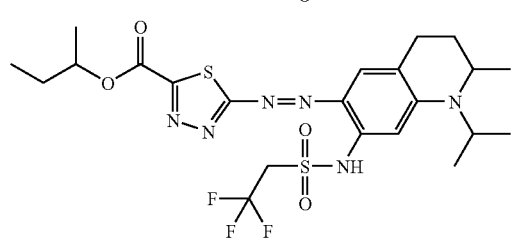
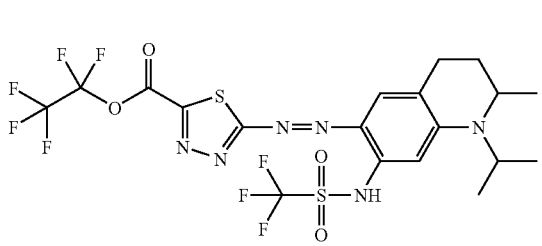
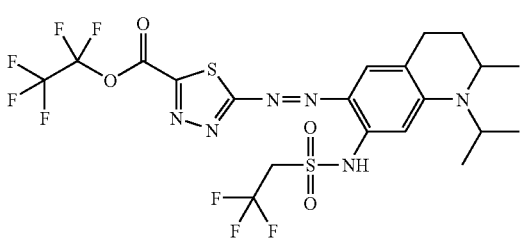
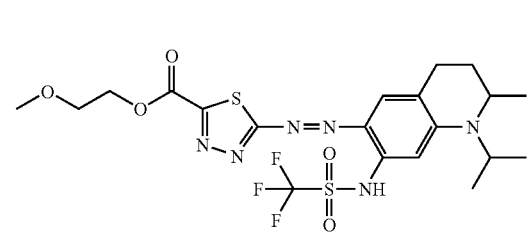
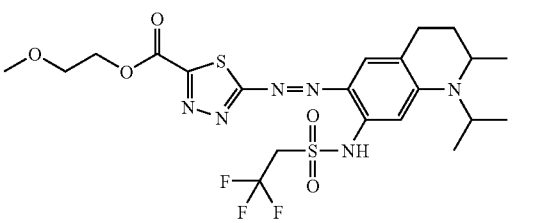

-continued
[formulae 17]
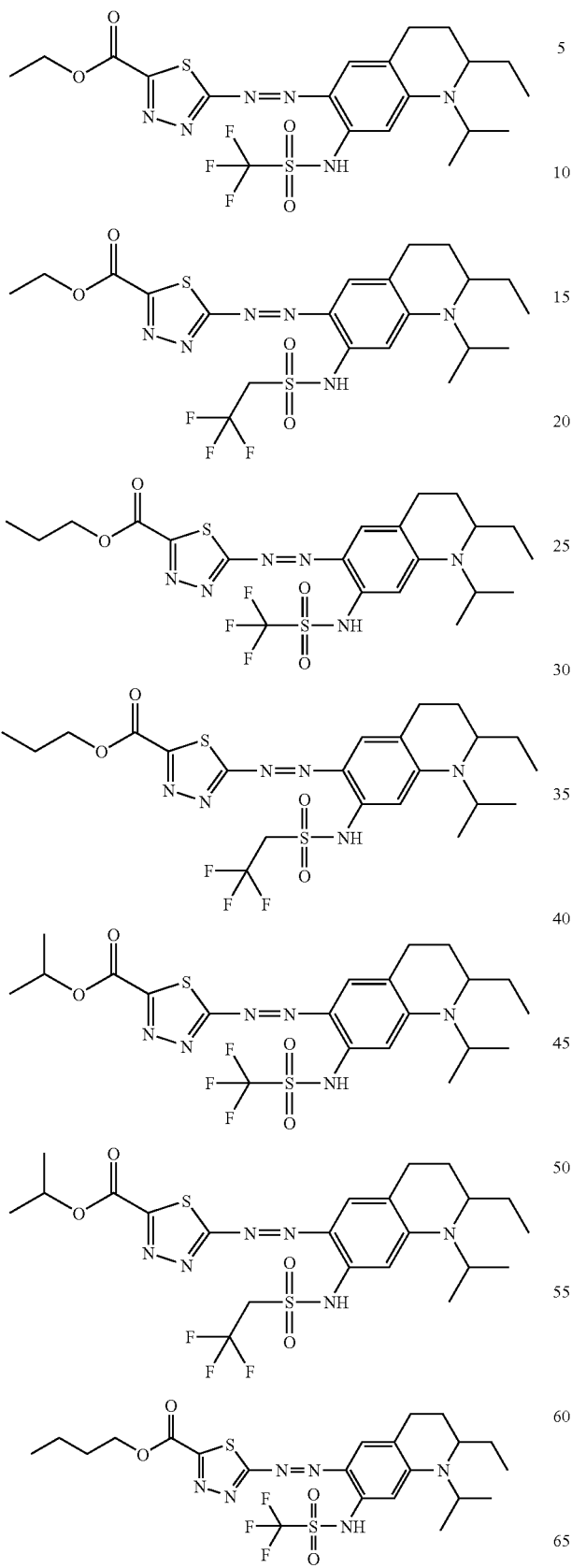
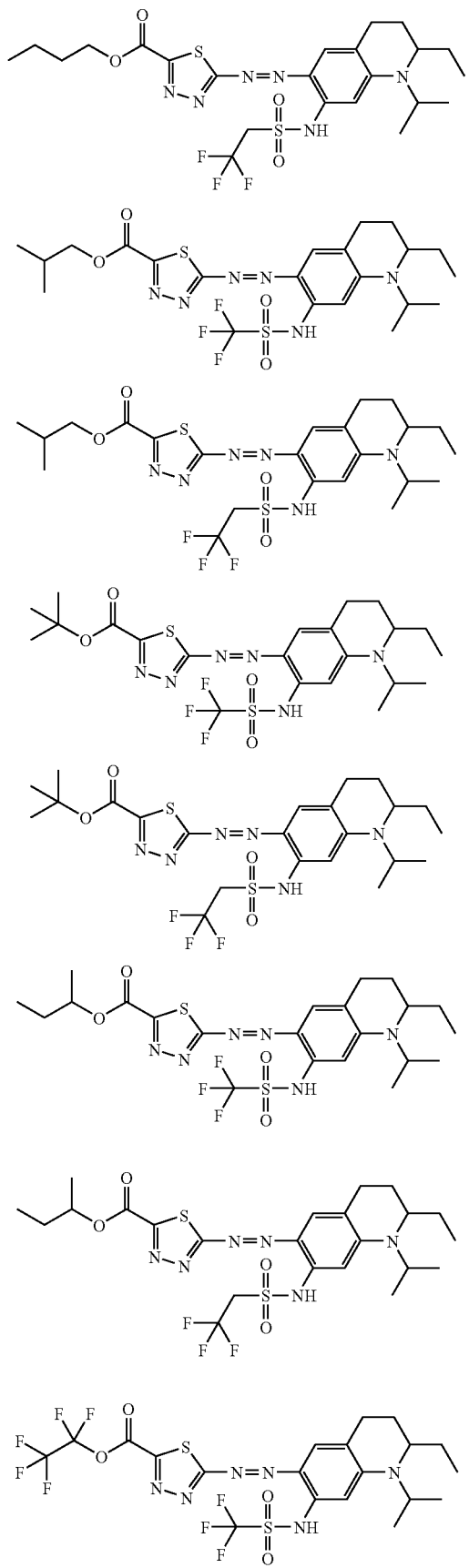

-continued
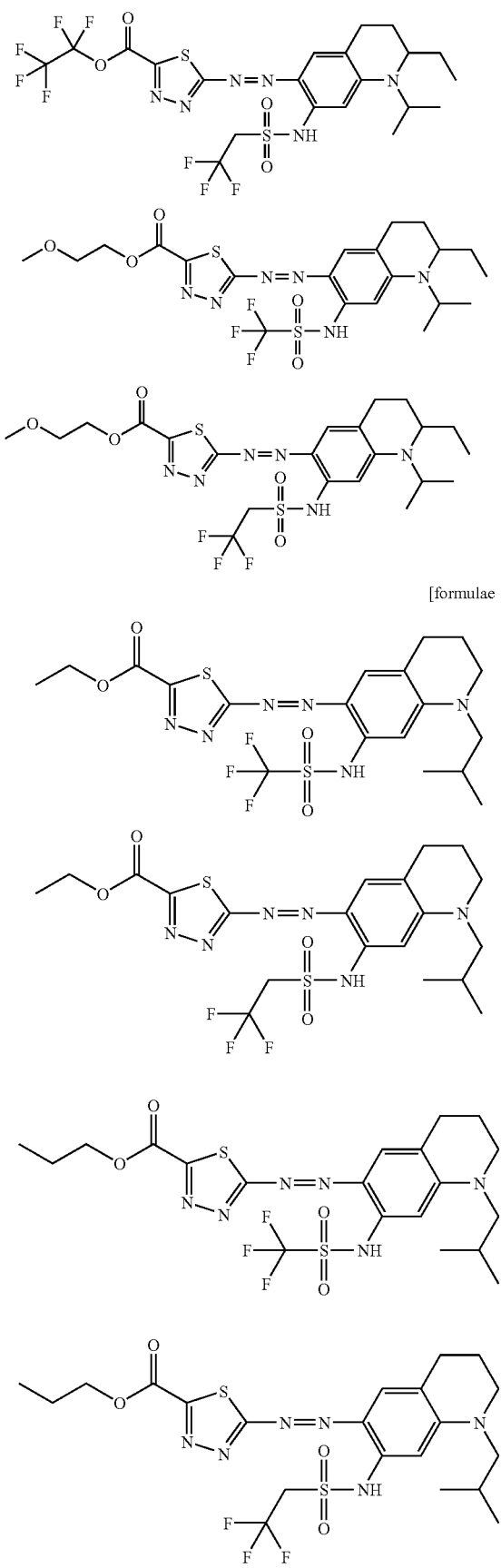
[formulae 18]
-continued
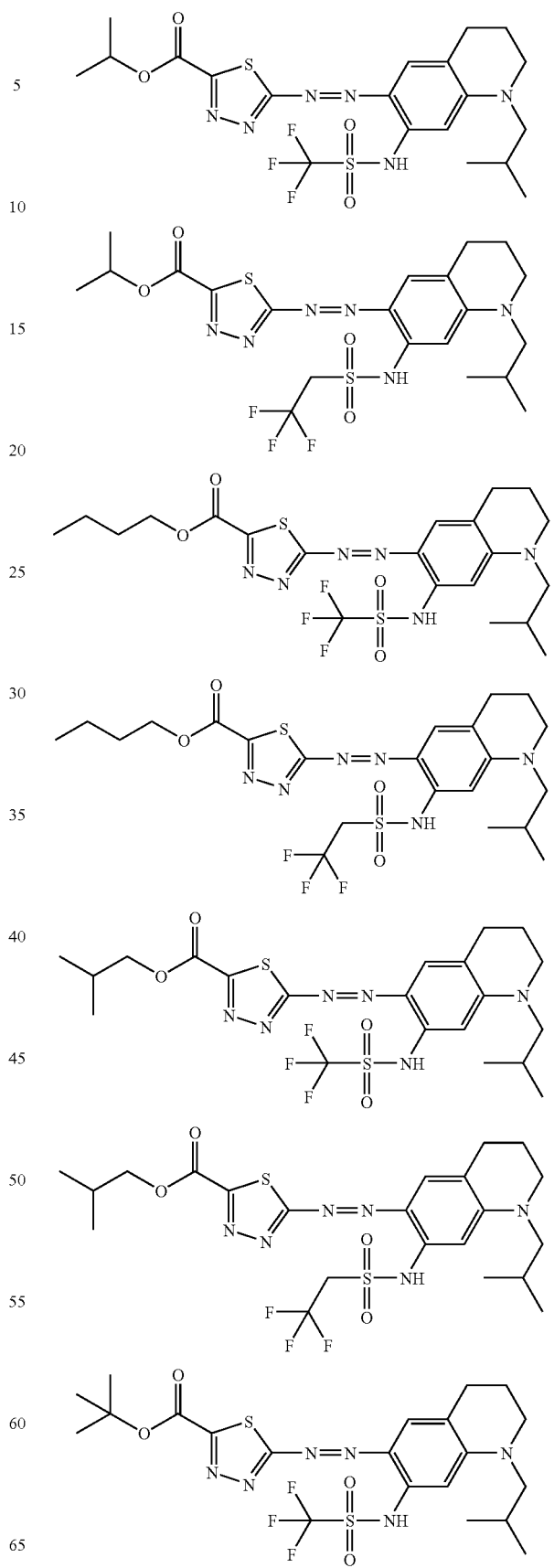

55
-continued
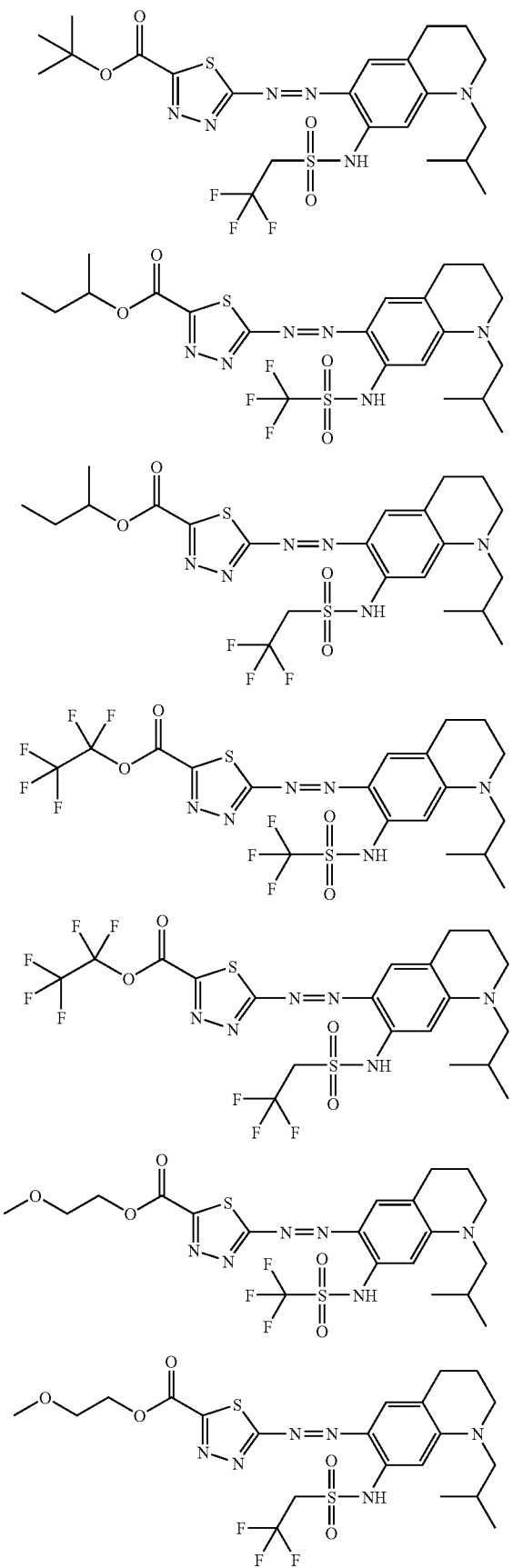
56
-continued
[formulae 19]
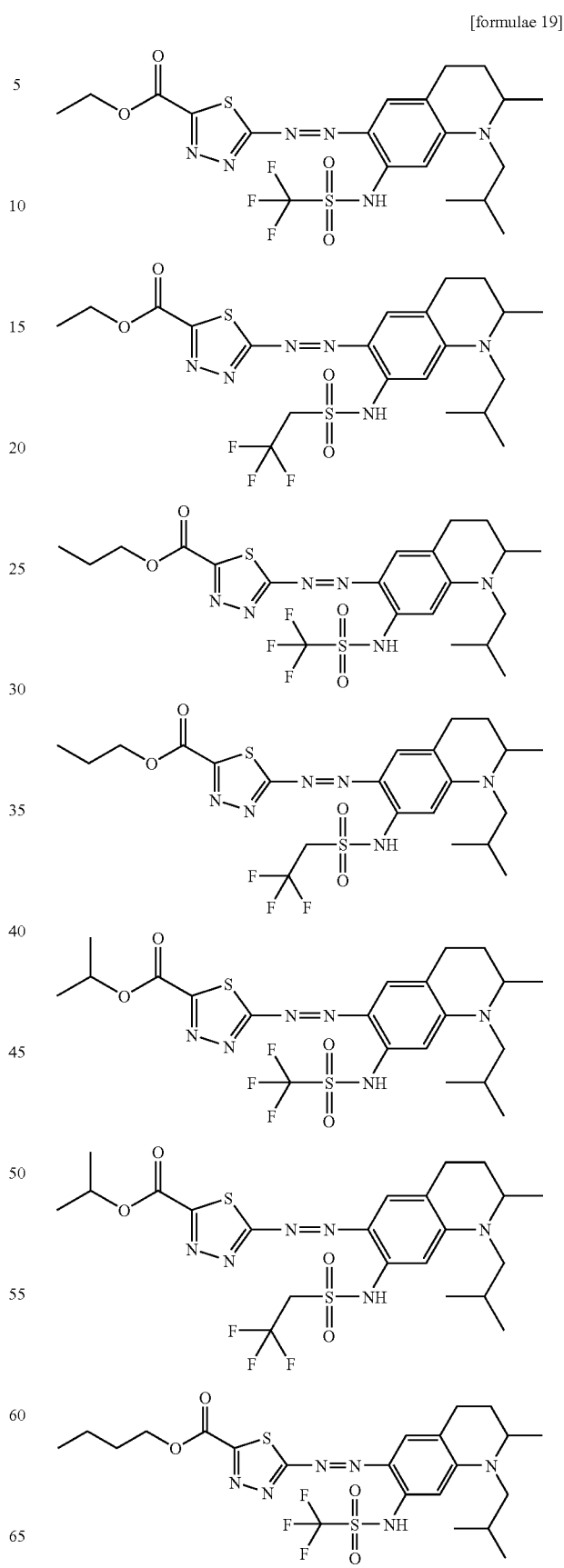

57
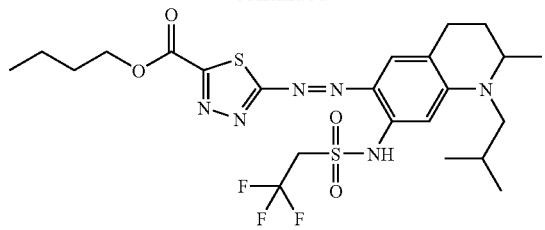
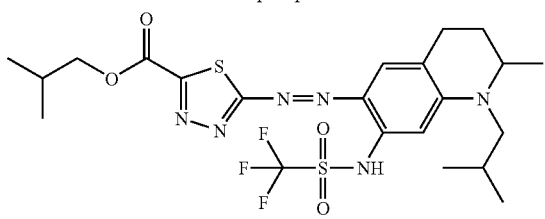
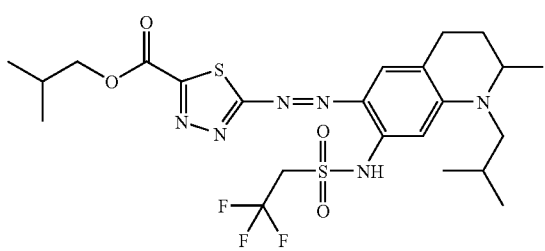
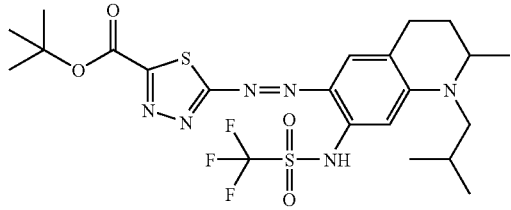
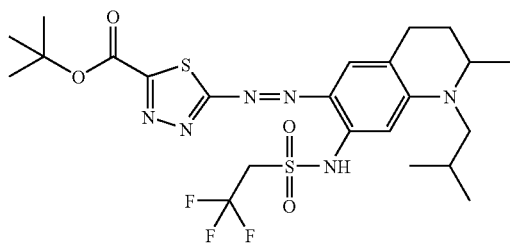
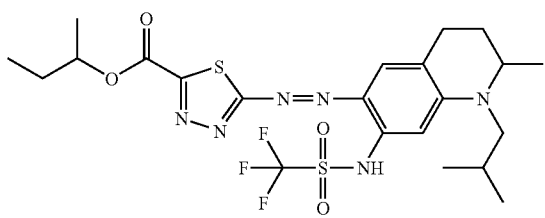
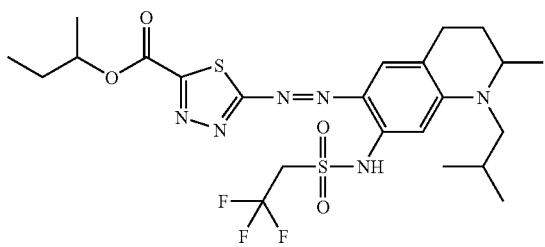
58
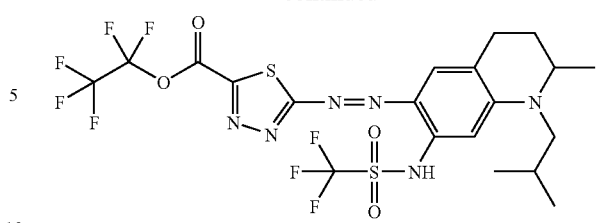
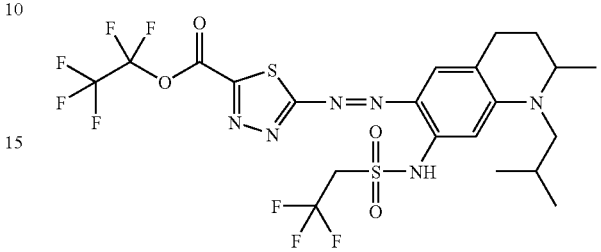
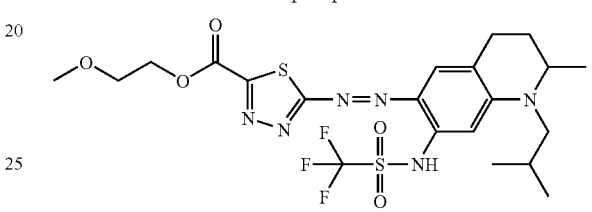
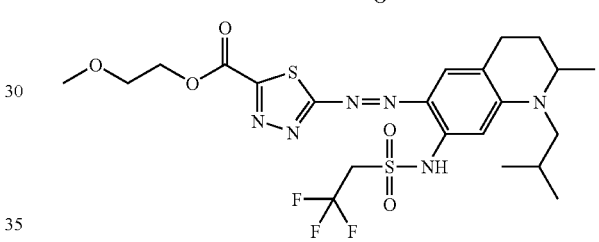
[formulae 20]
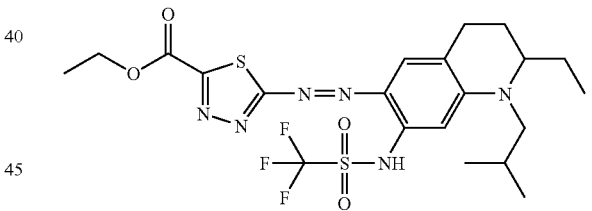
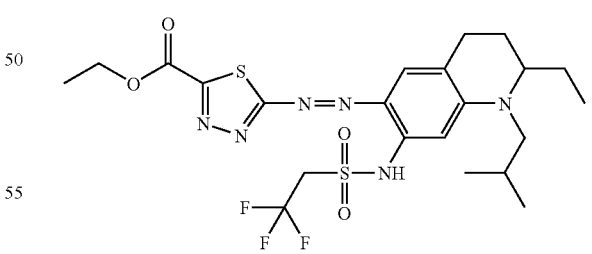
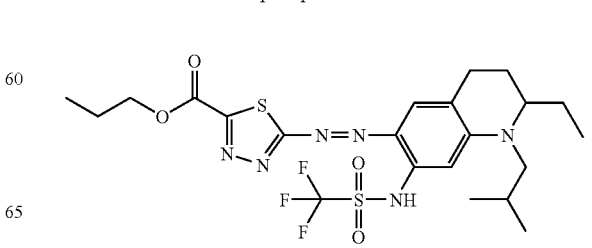

59
-continued
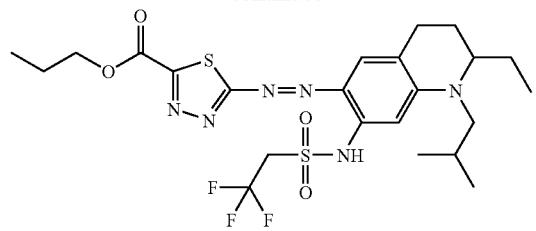
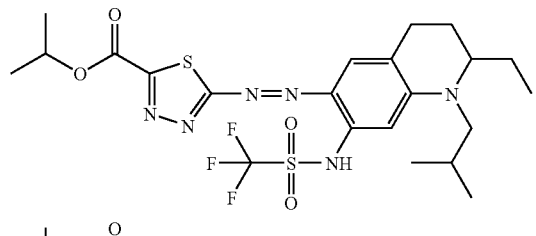
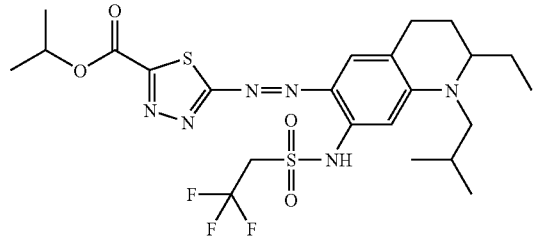
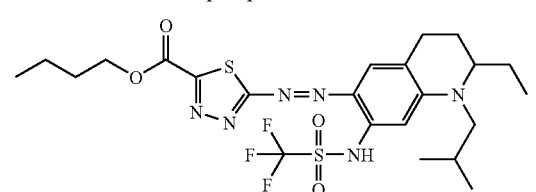
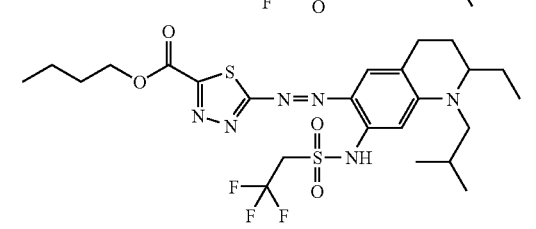
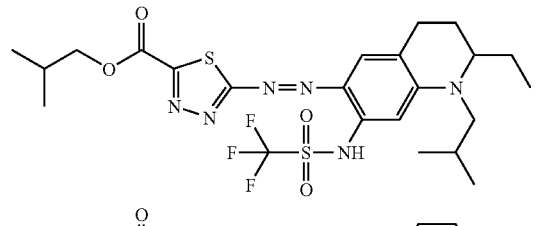
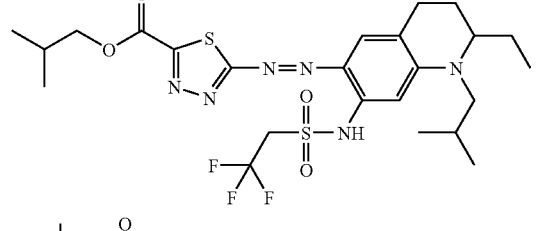
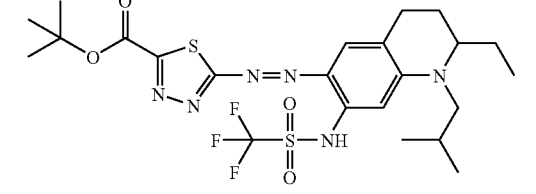
60
-continued
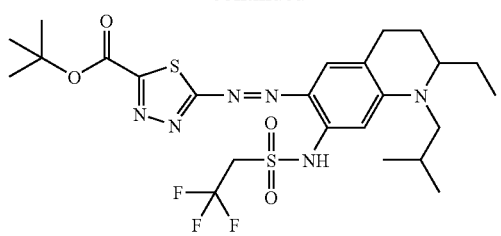
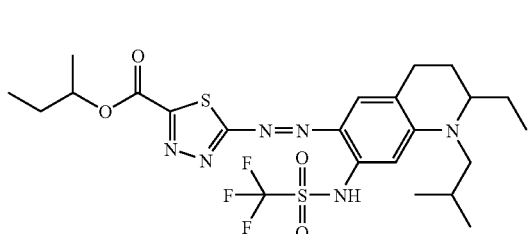
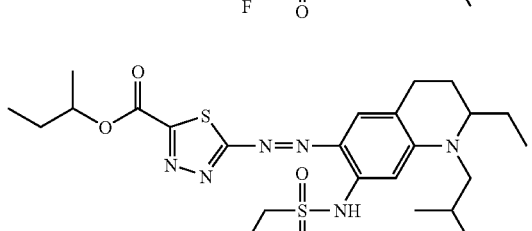
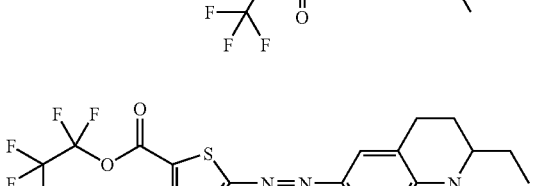
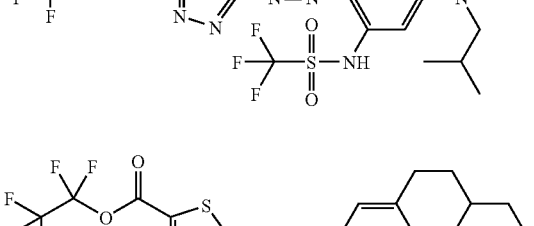
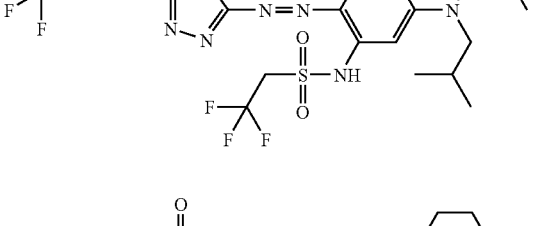
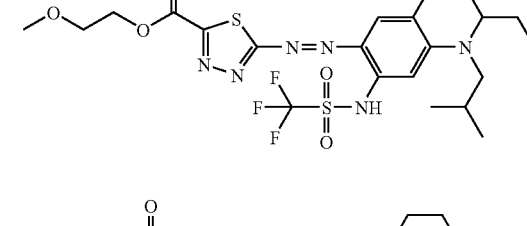
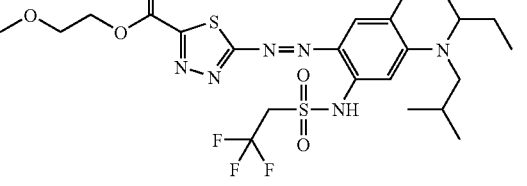

[formulae 21]
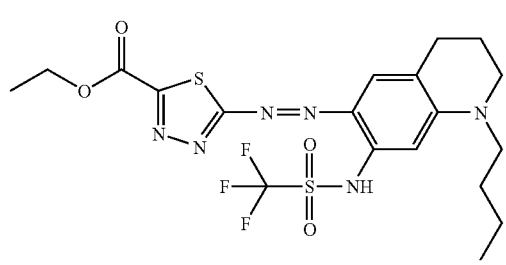
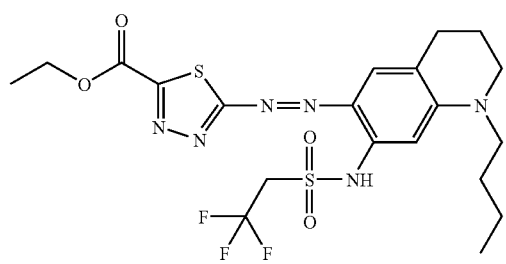
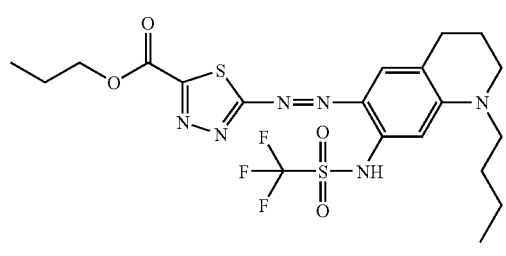
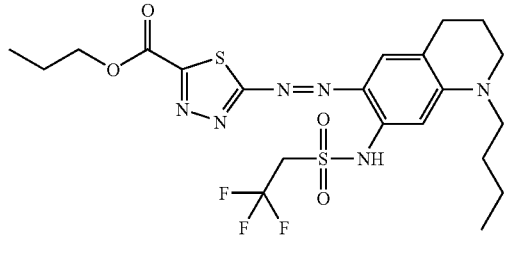
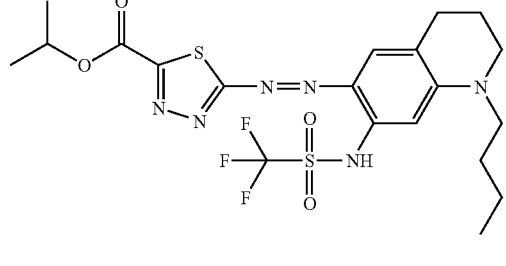
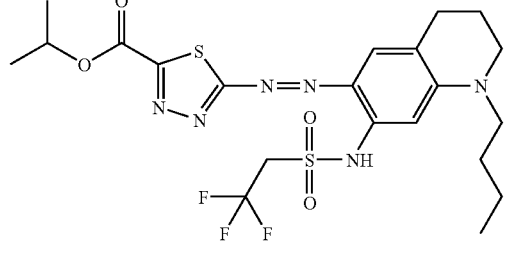
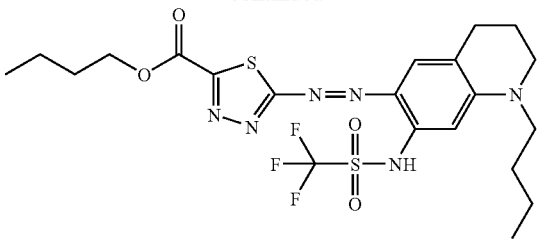
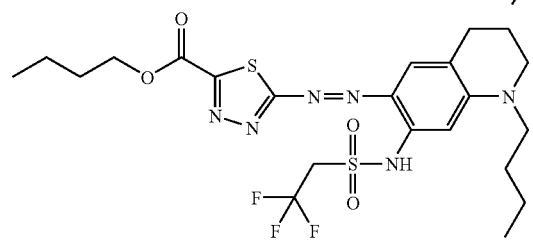
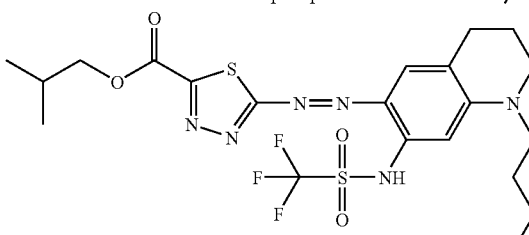
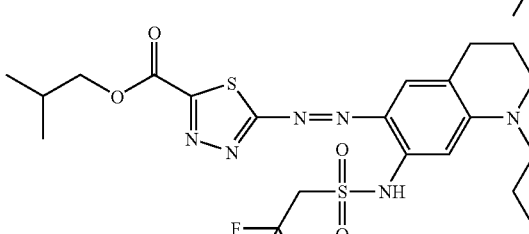
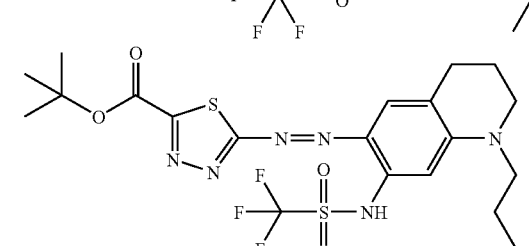
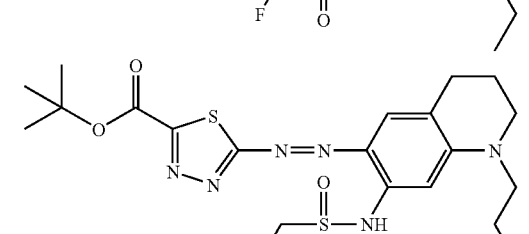
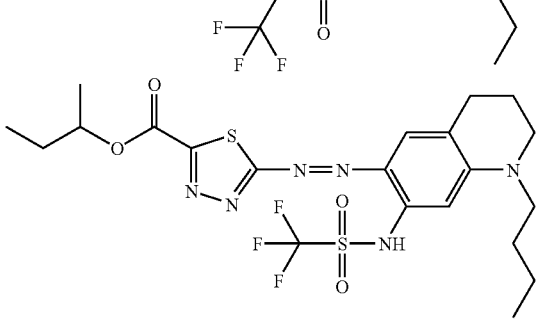

63
-continued
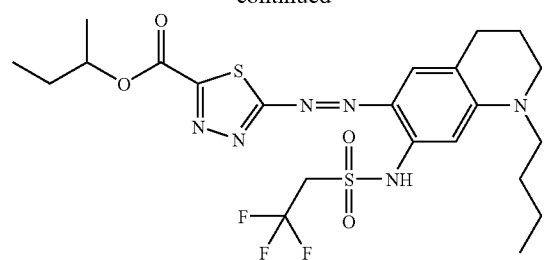
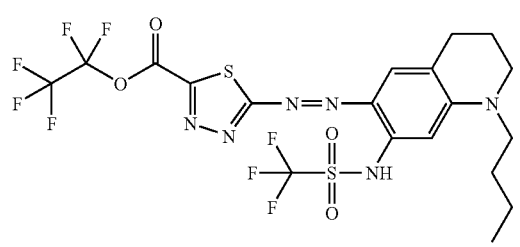
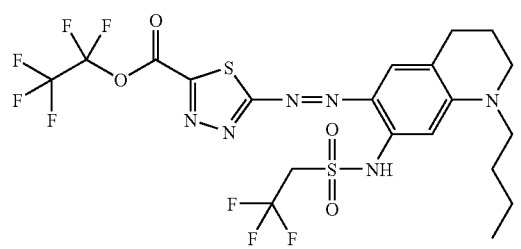
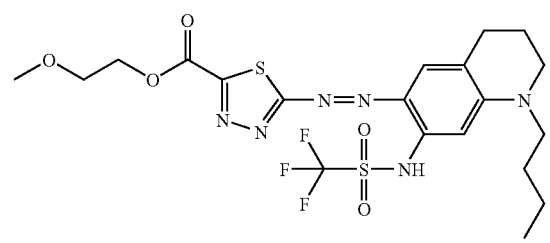
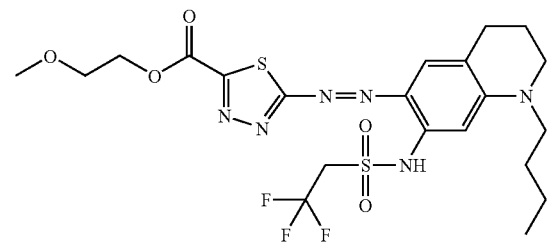
[formulae 22]
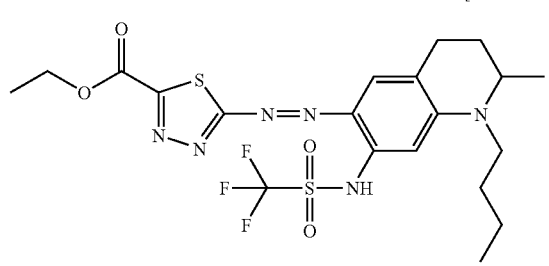
64
-continued
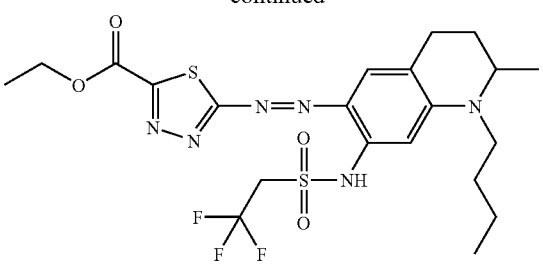
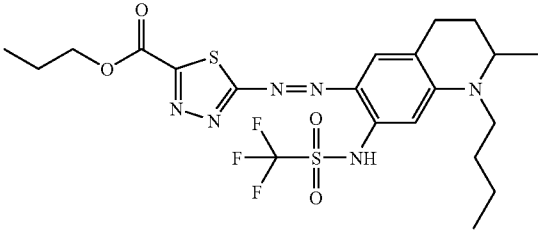
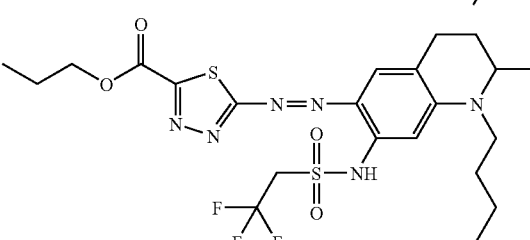
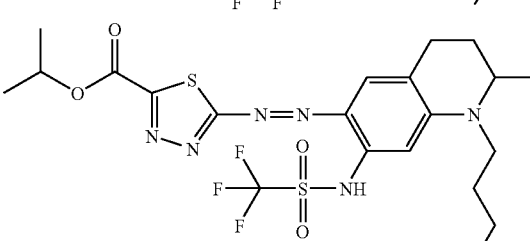
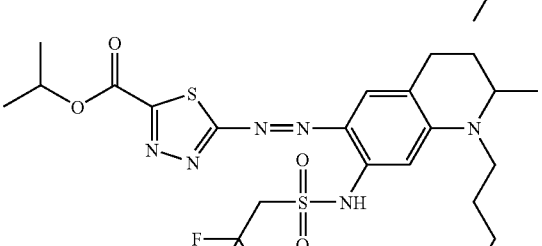
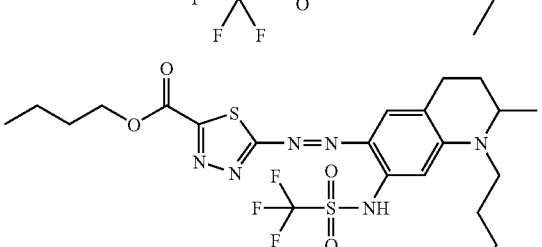
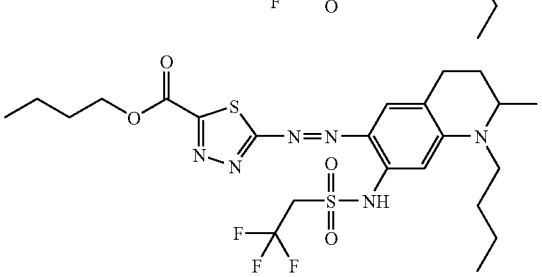

65
-continued
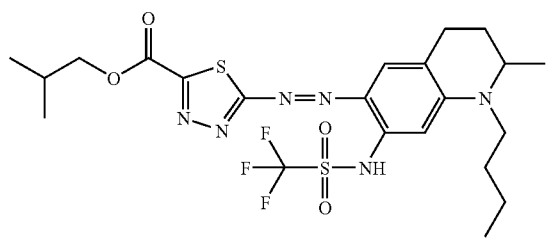
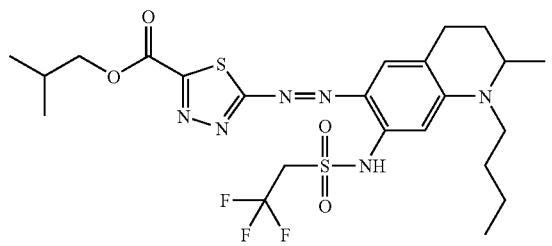
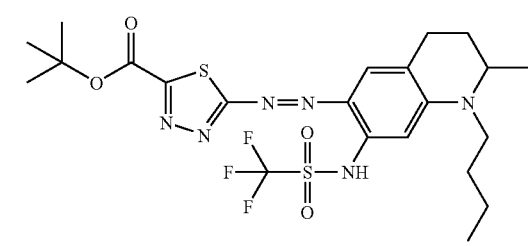
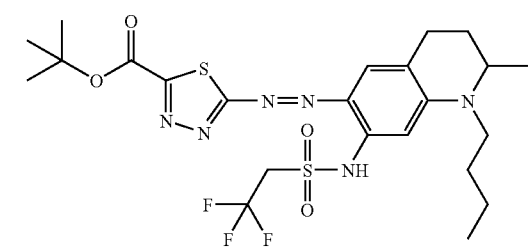
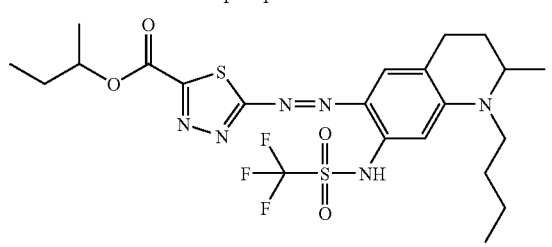
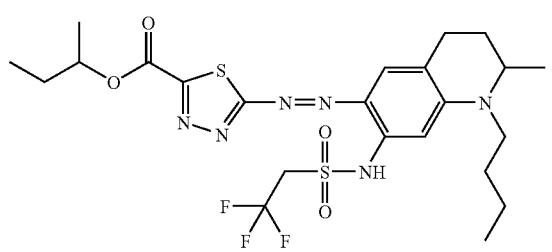
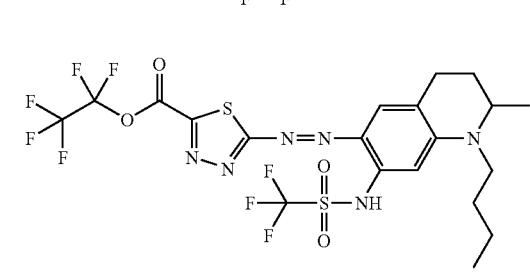
66
-continued
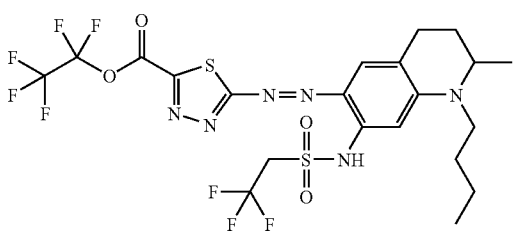
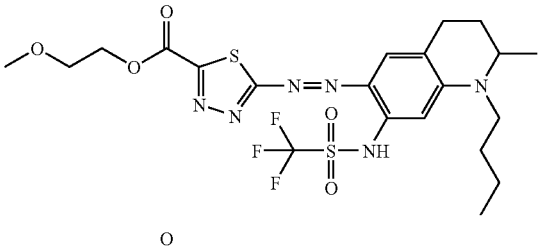
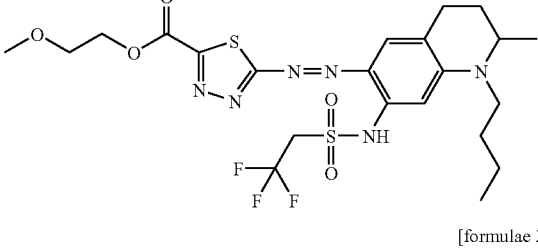
[formulae 23]
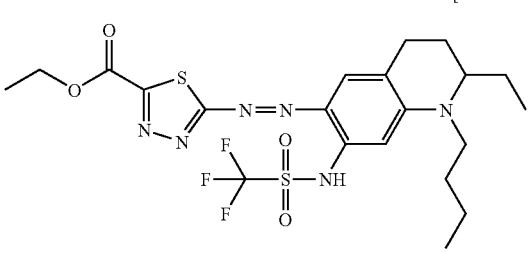
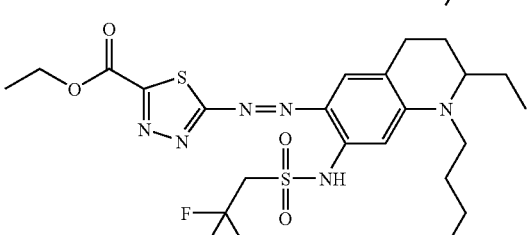
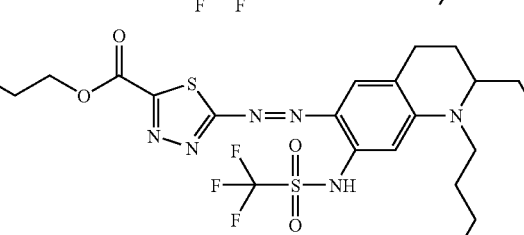
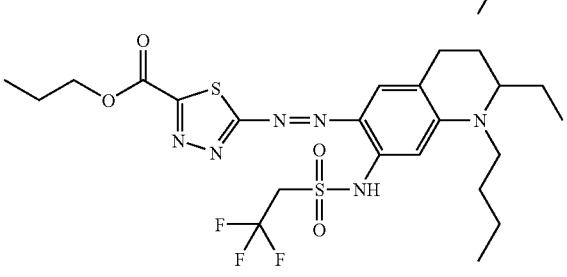

67
-continued
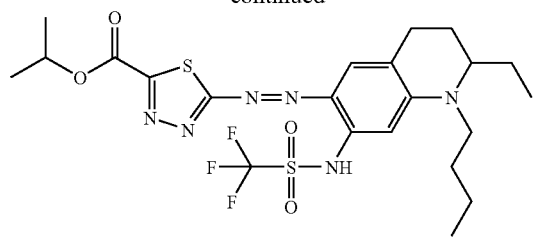
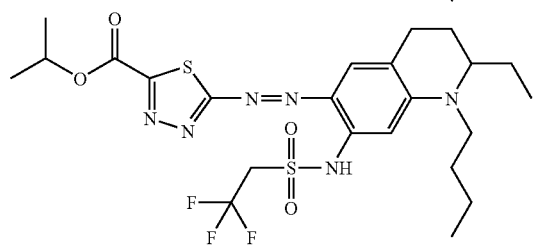
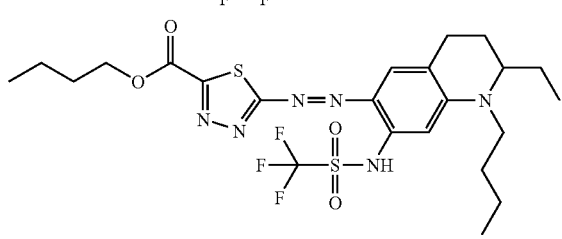
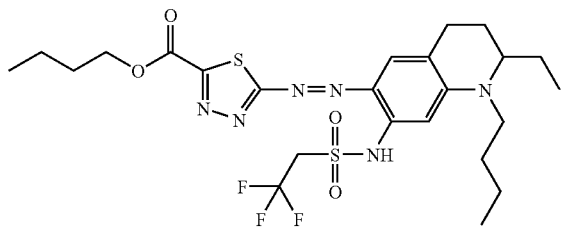
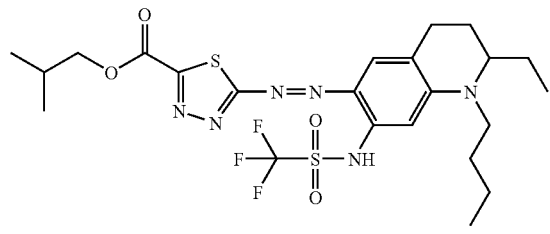
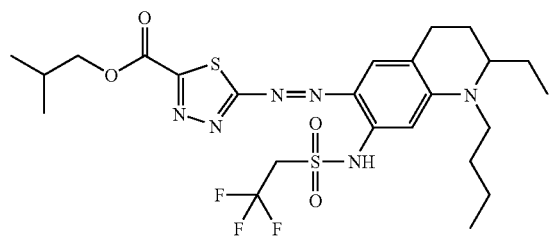
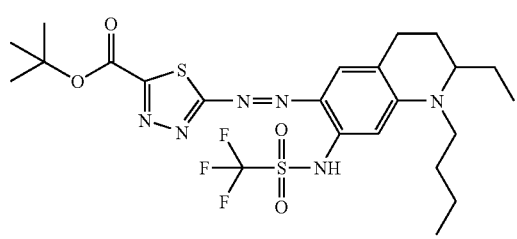
68
-continued
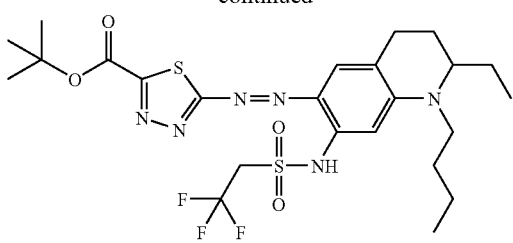
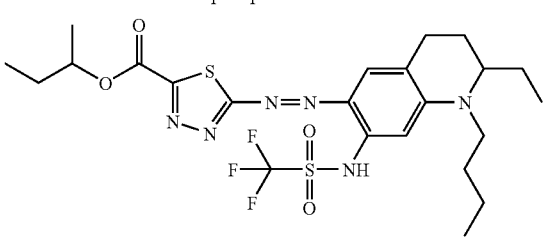
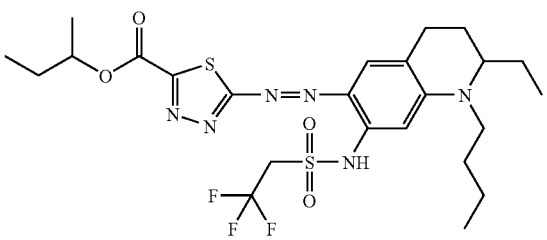
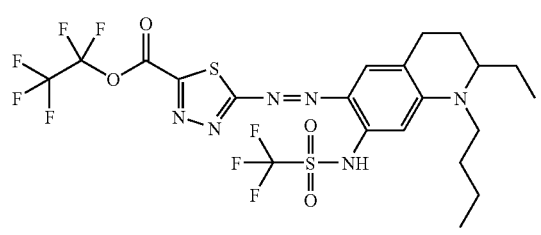
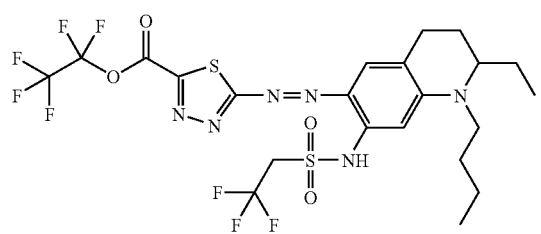
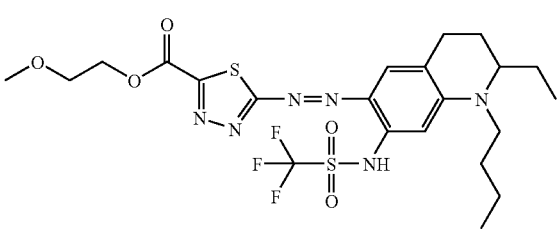
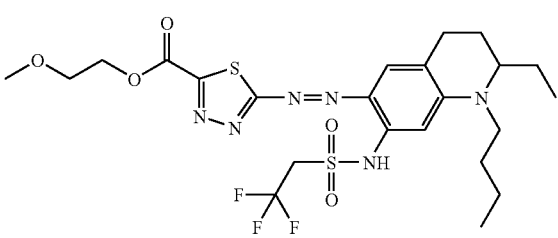

[formulae 24]
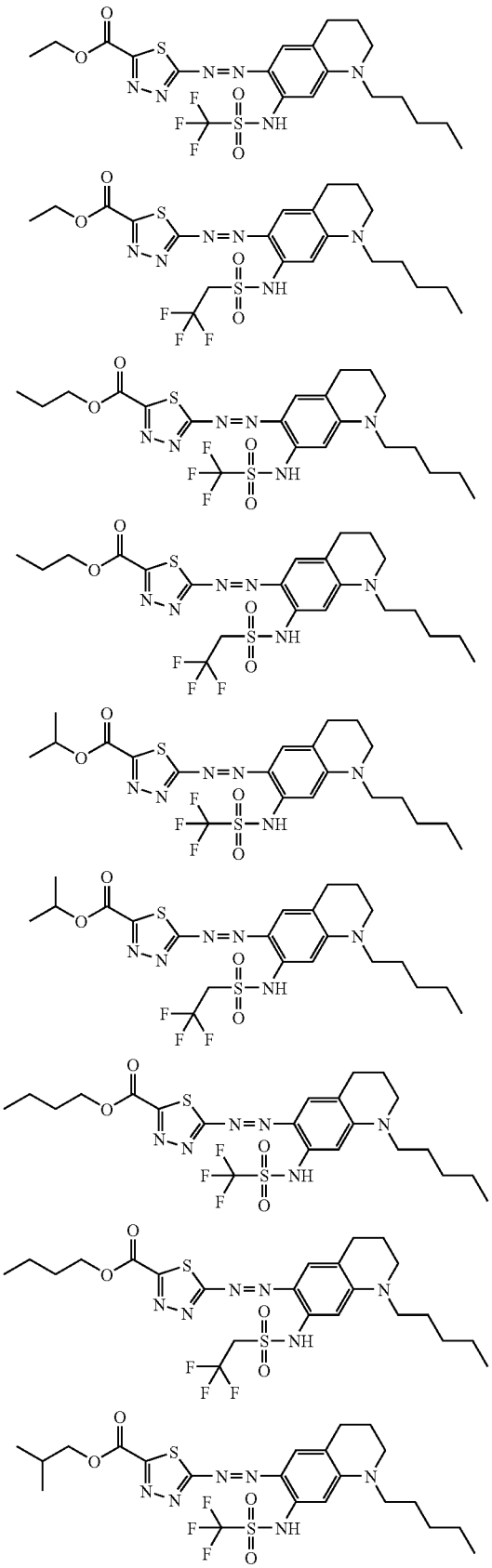
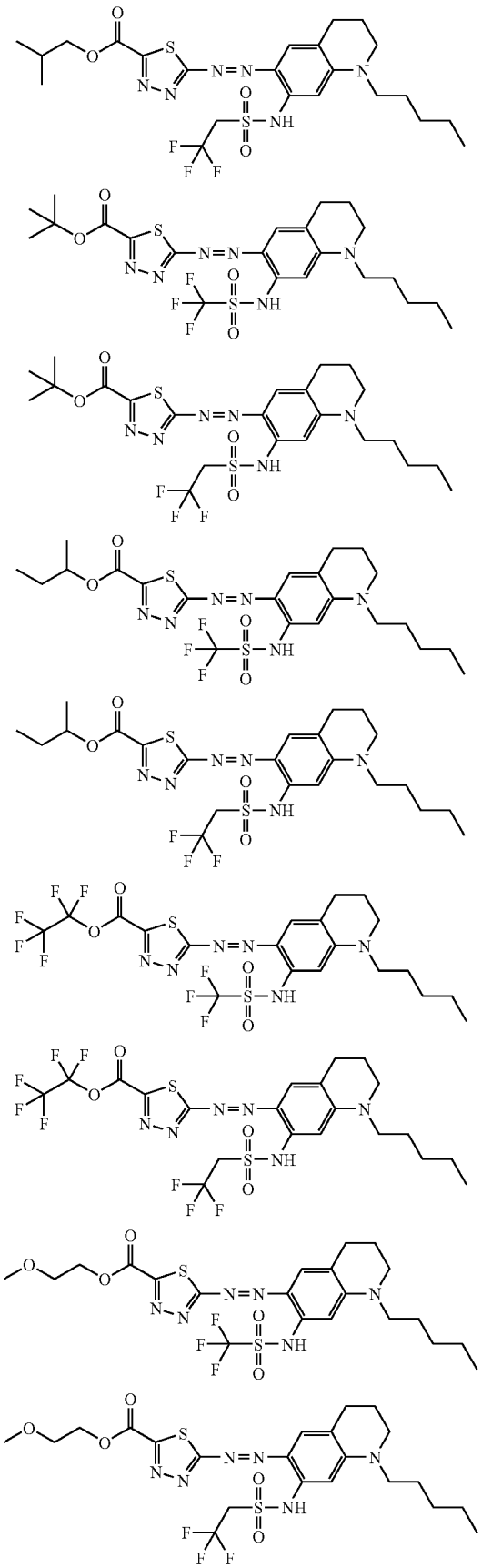

[formulae 25]
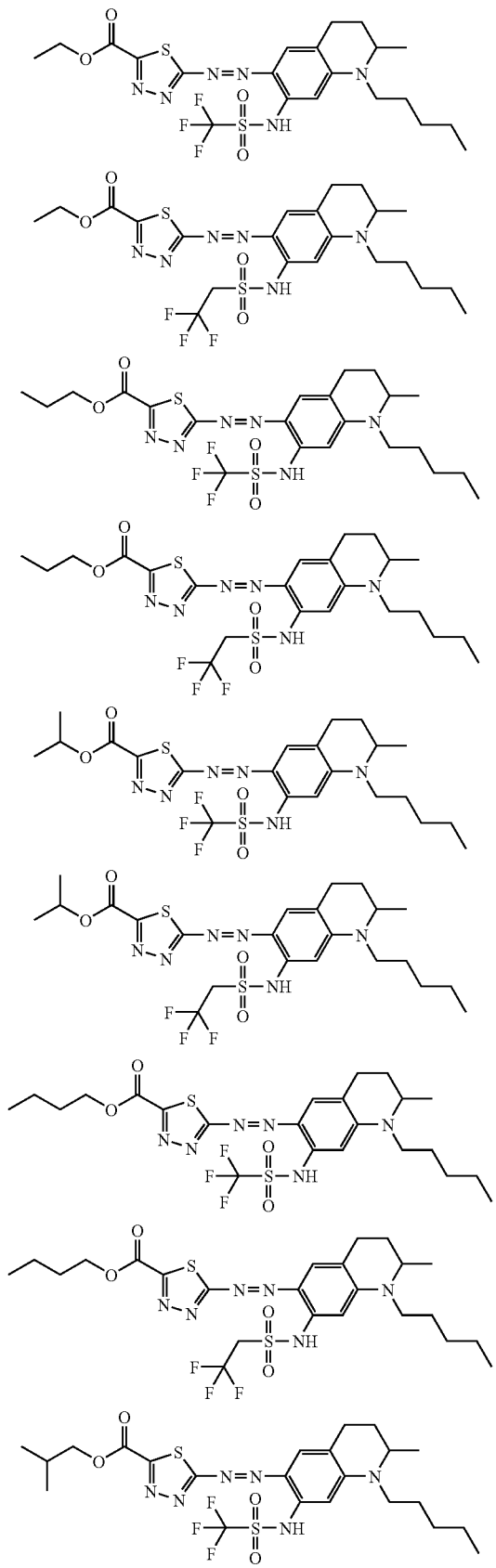
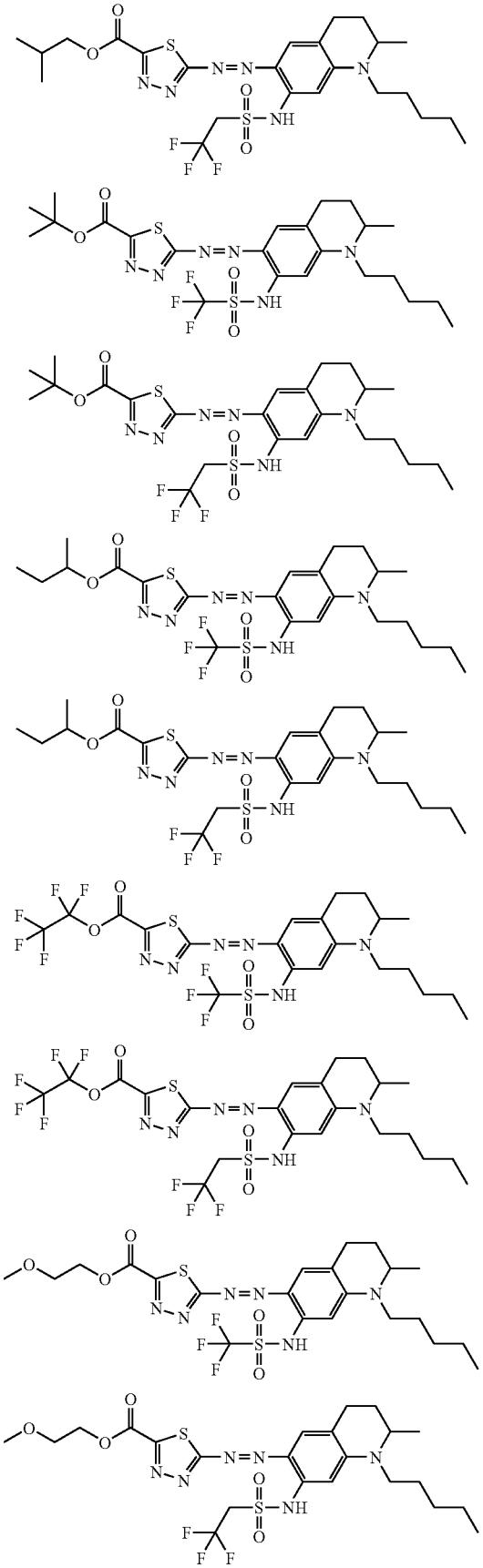

[formulae 26]
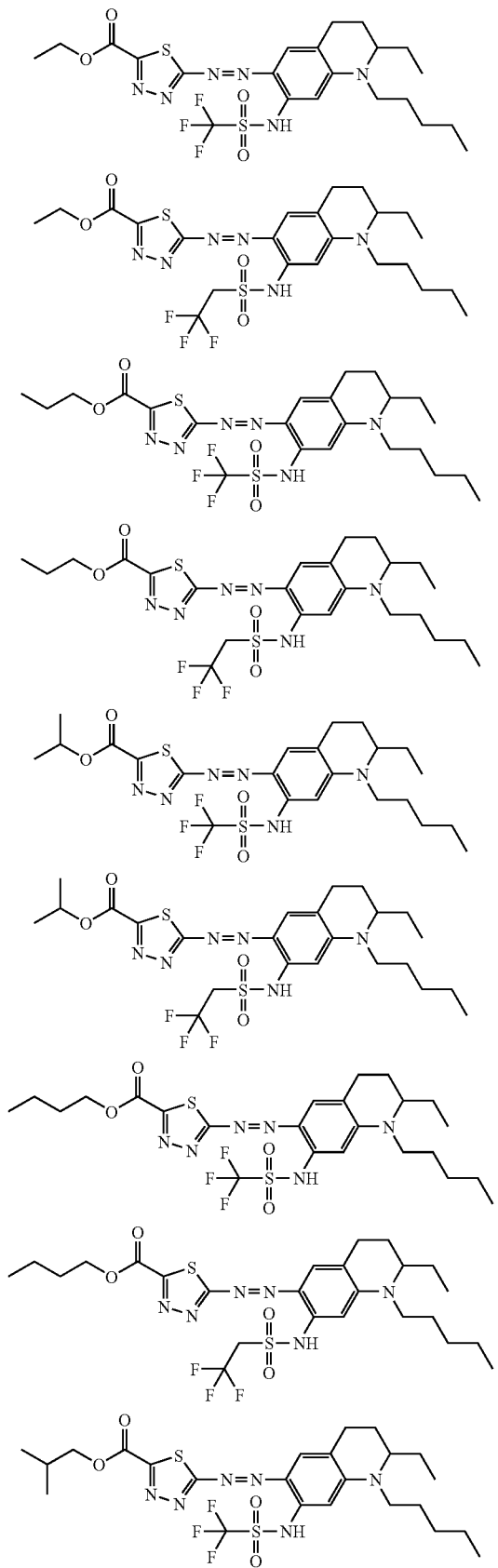
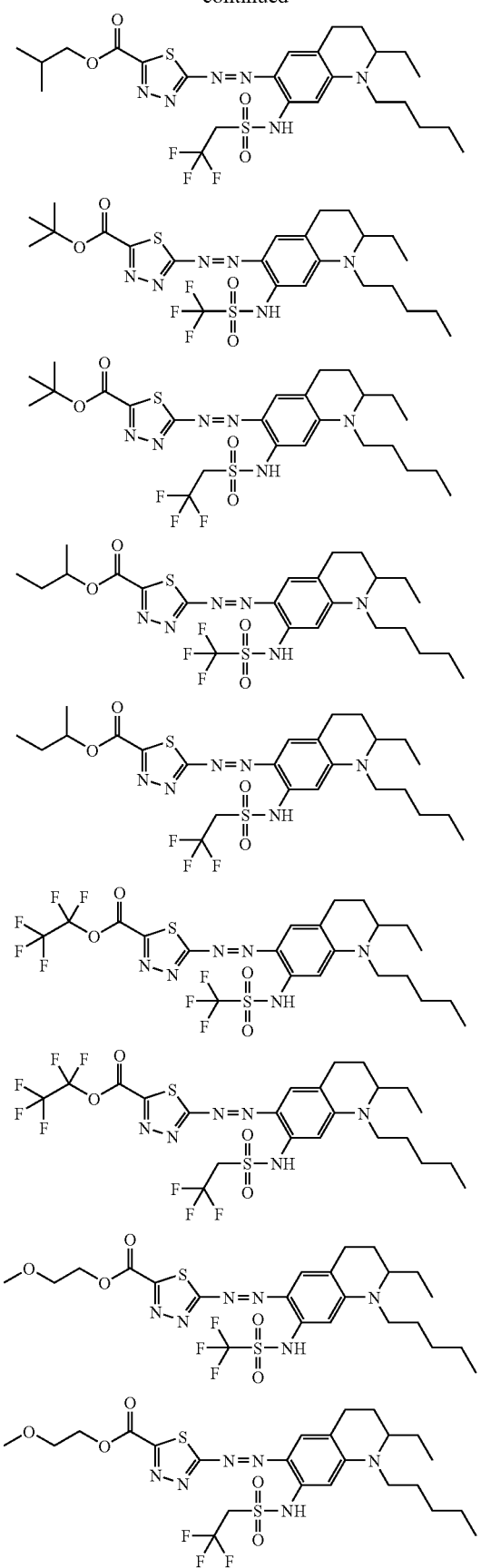

[formulae 27]
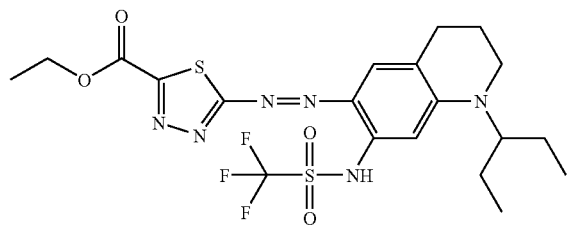
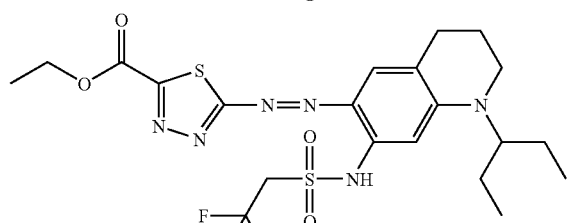
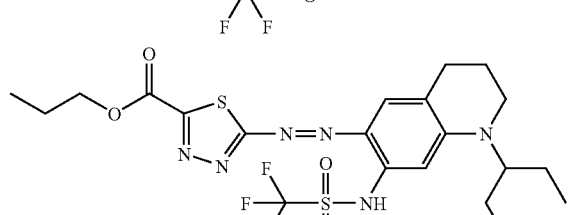
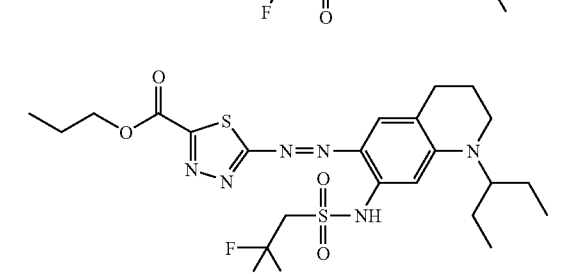
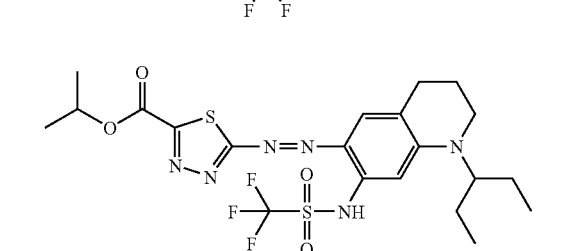
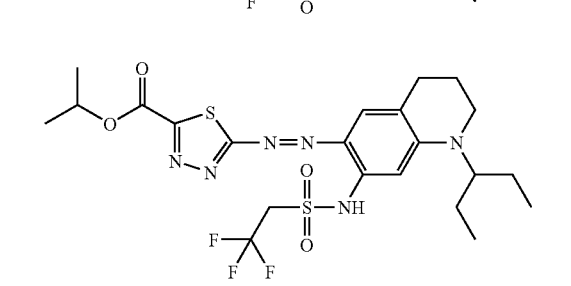
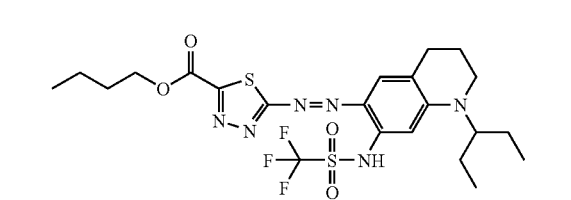
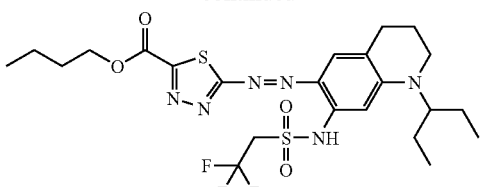
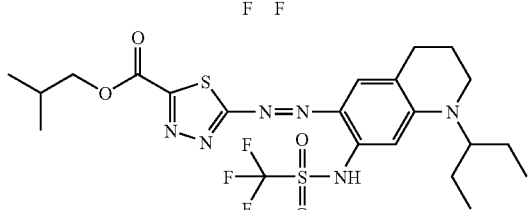
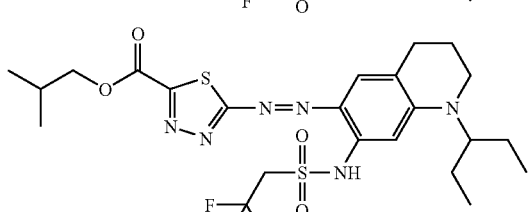
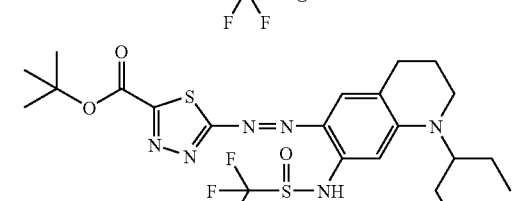
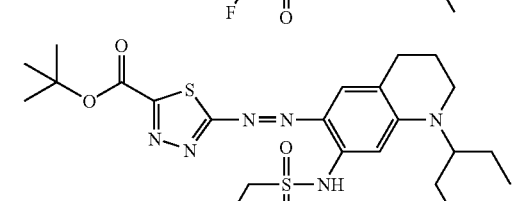
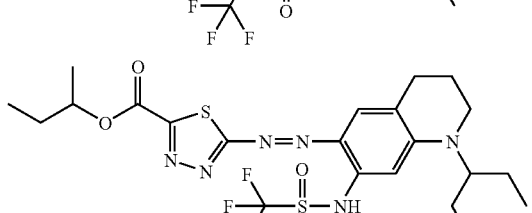
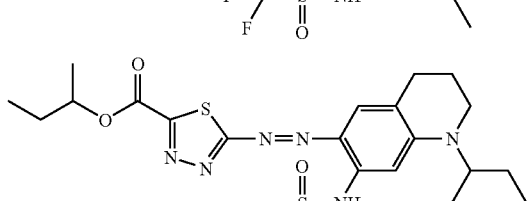
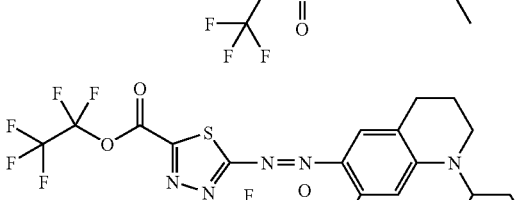

77
-continued
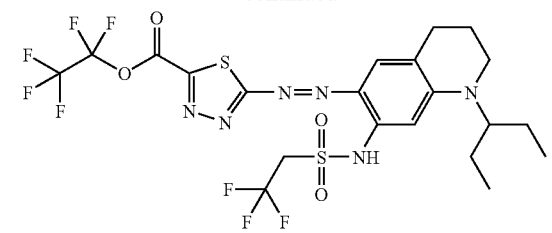
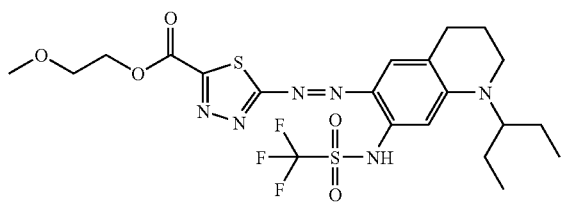
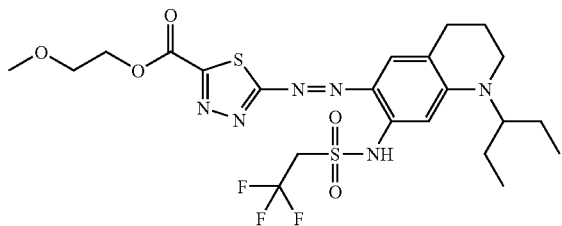
[formulae 28]
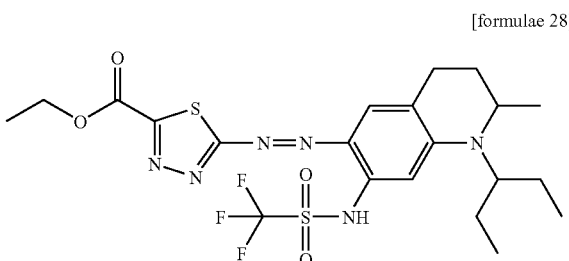
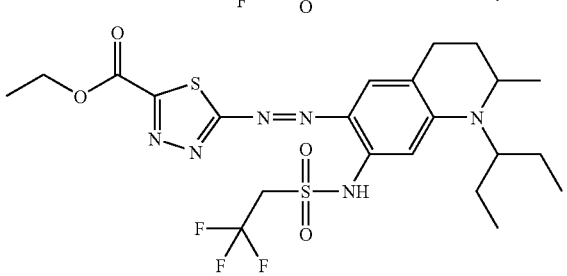
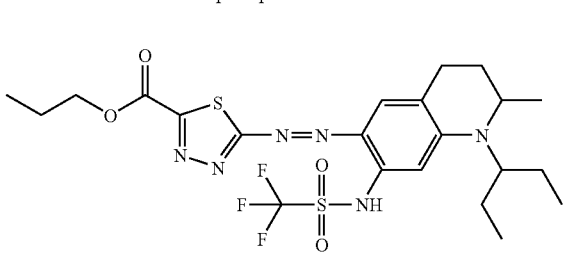
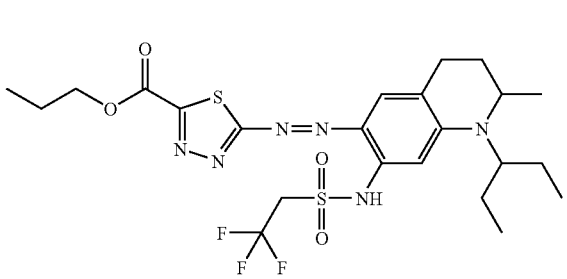
78
-continued
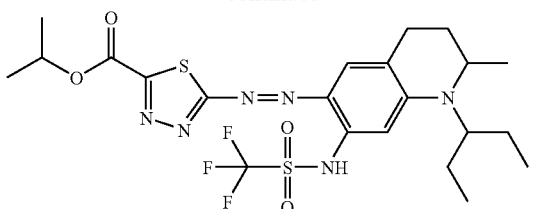
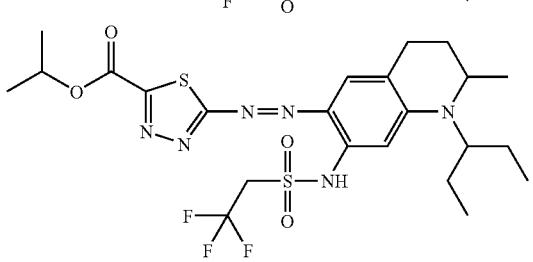
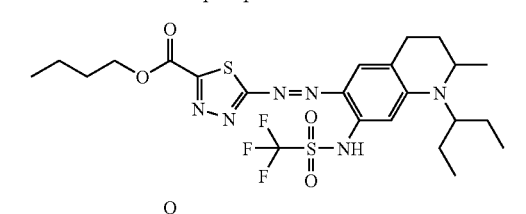
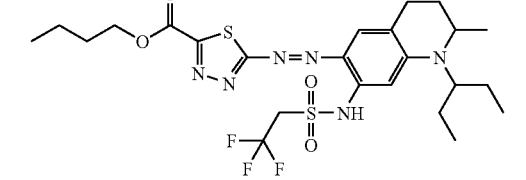
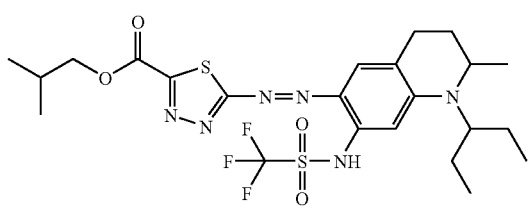
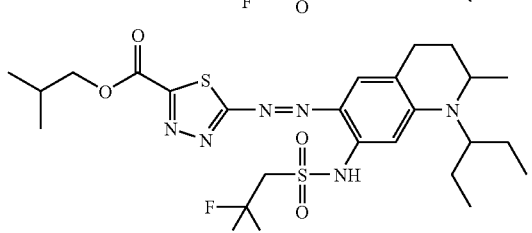
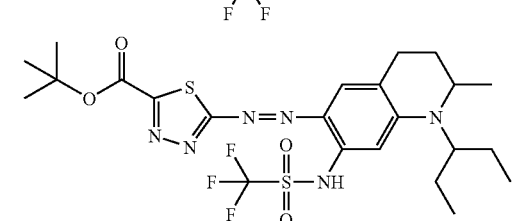
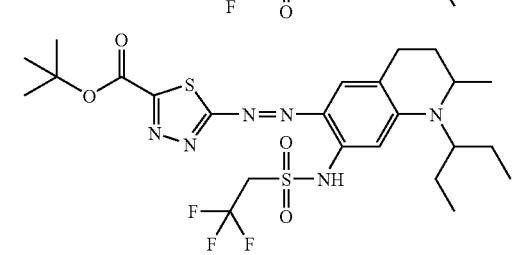

-continued
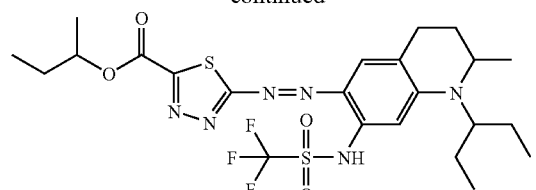
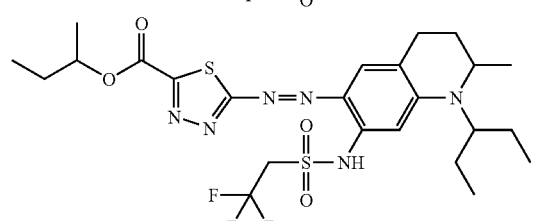
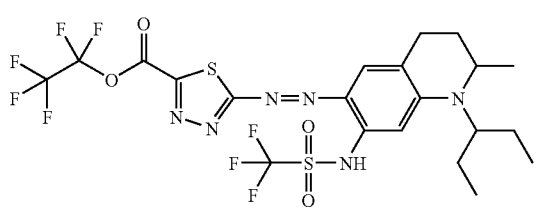
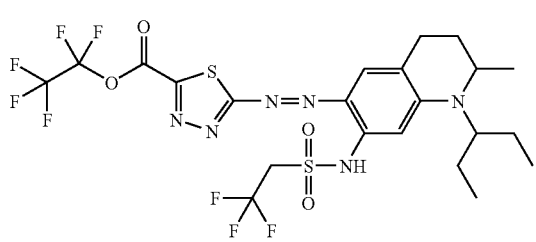
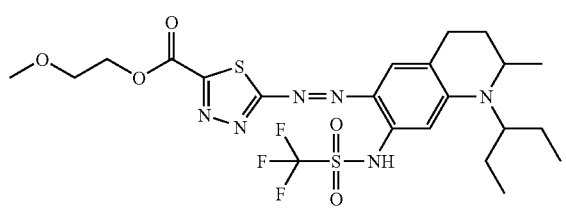
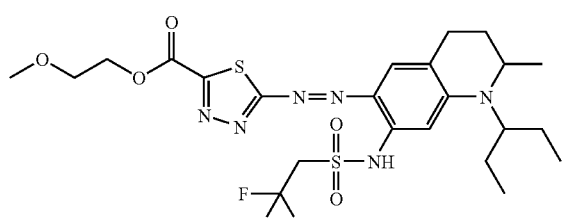
[formulae 29]
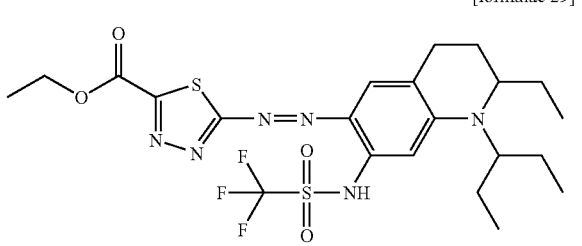
-continued
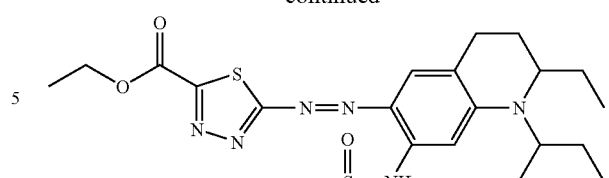
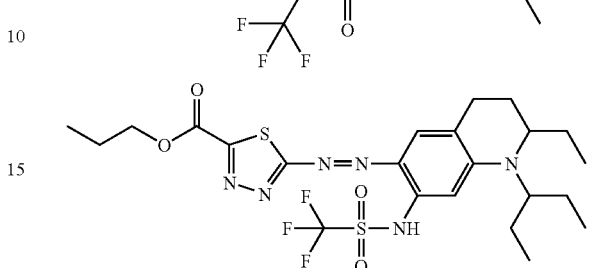
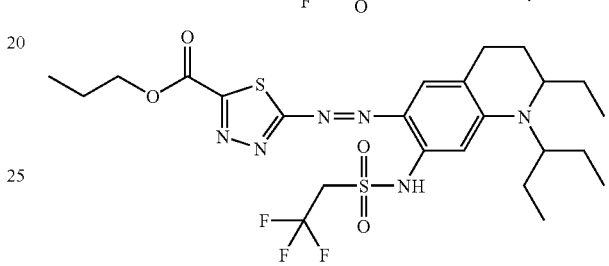
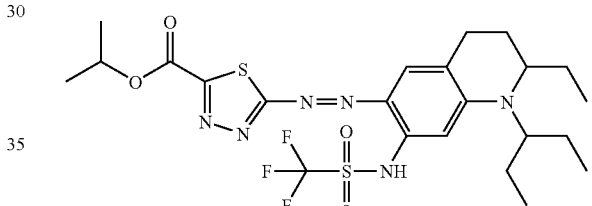
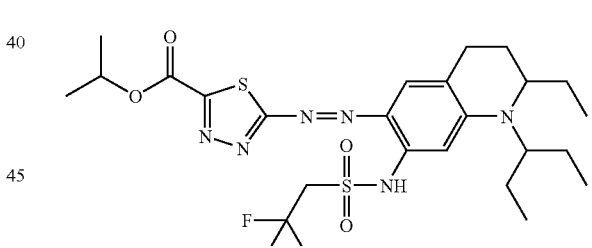
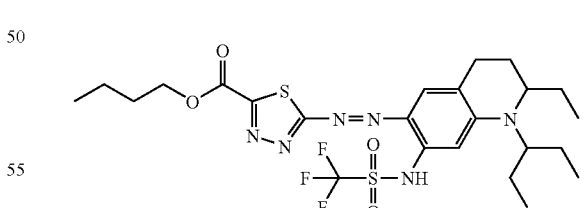

81
-continued
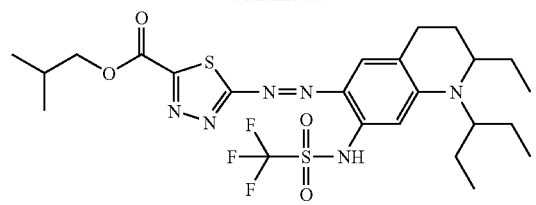
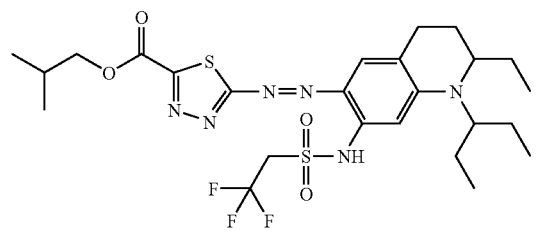
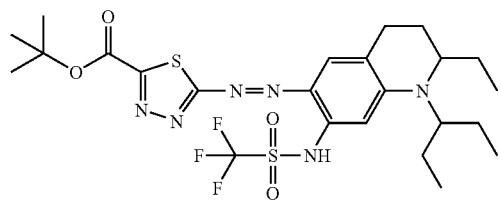
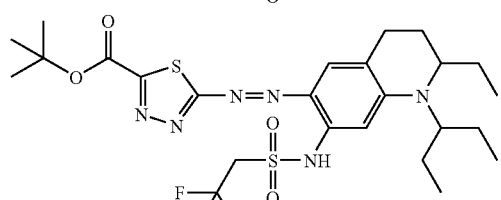
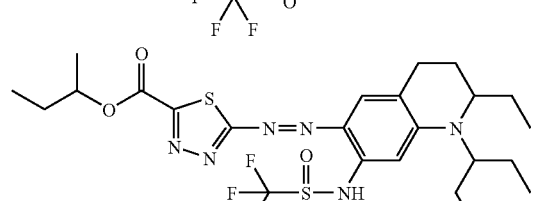
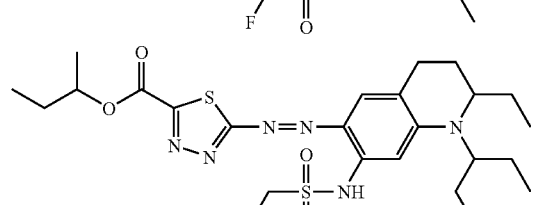
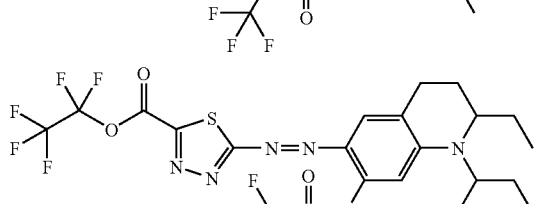
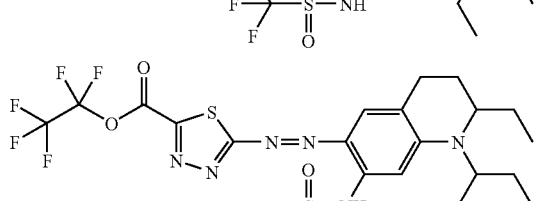
82
-continued
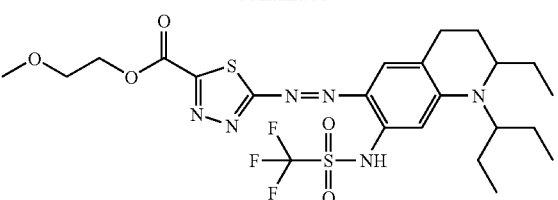
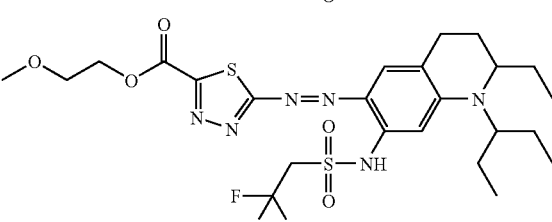
[formulae 30]
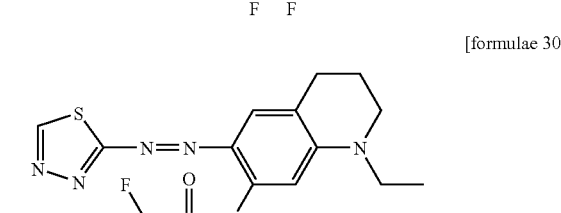
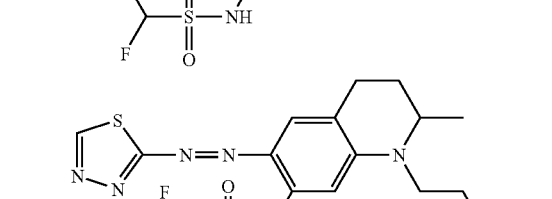
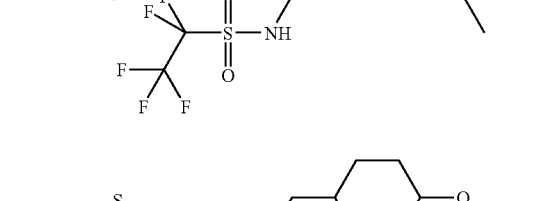
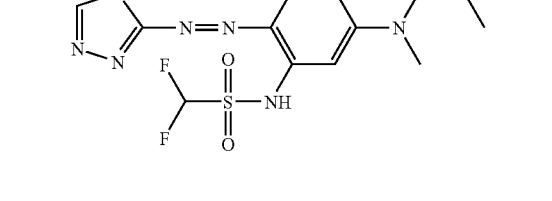
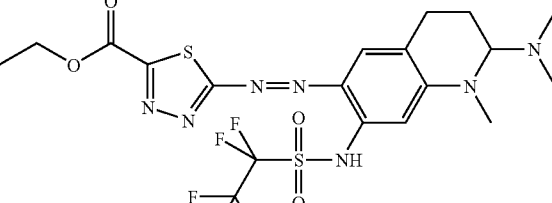
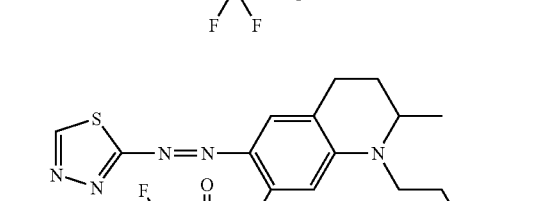

83
-continued
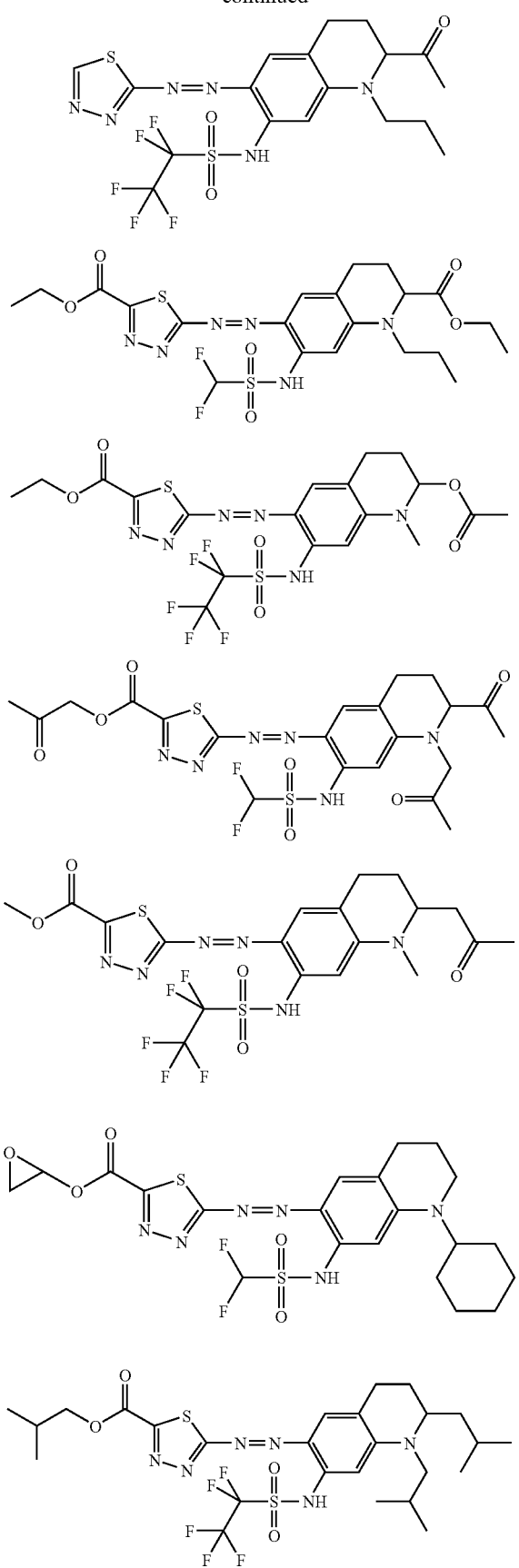
84
-continued
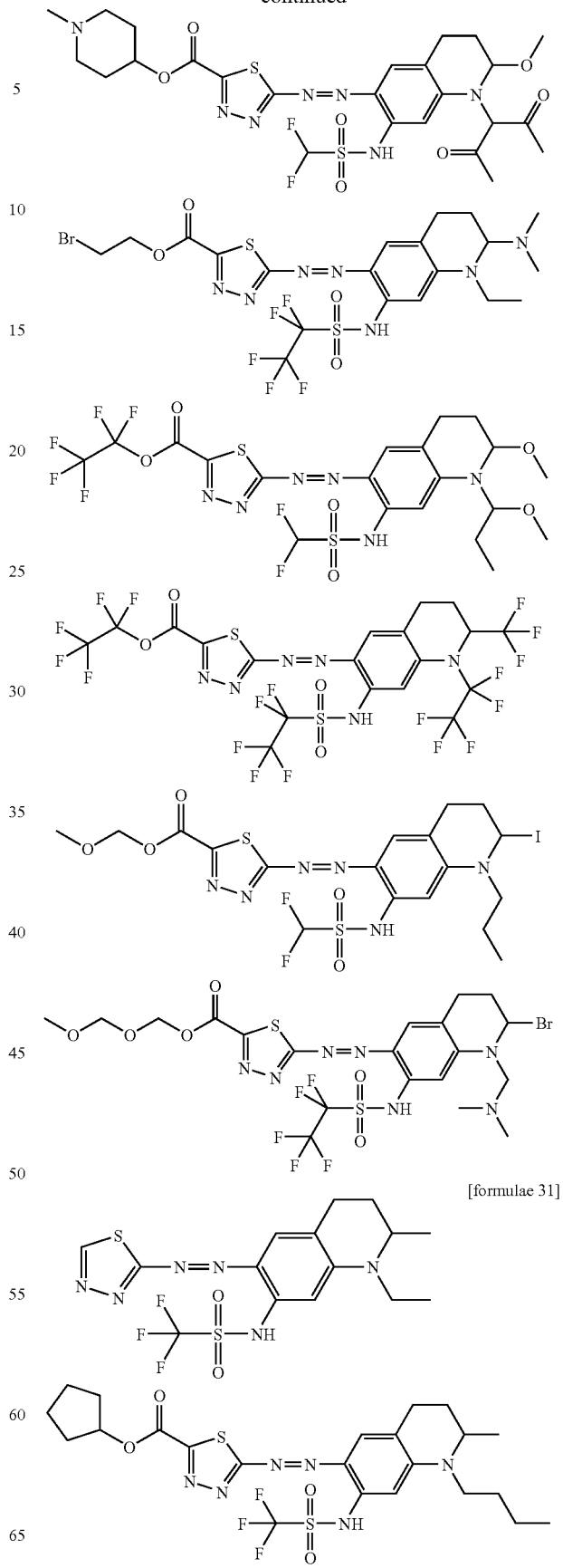
[formulae 31]

85
-continued
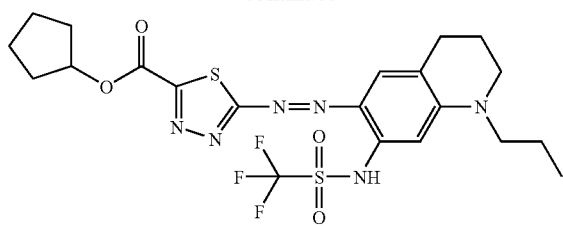
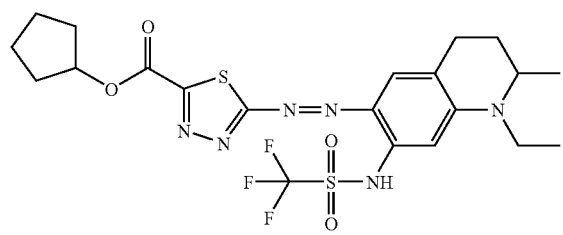
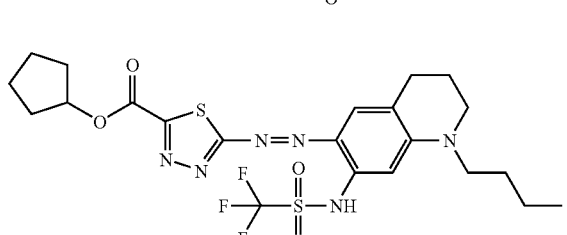
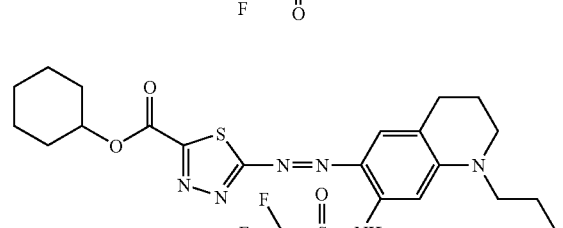
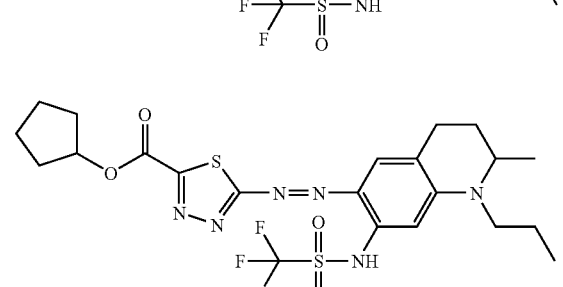
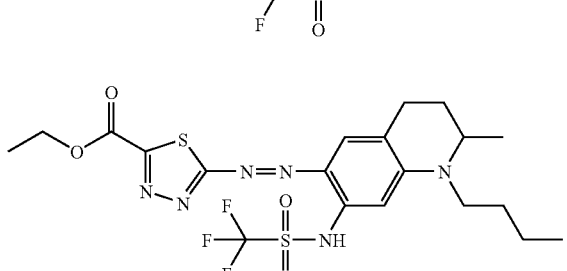
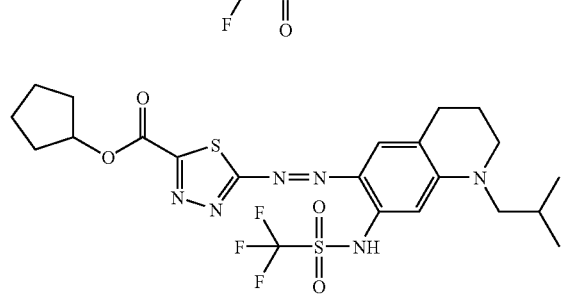
86
-continued
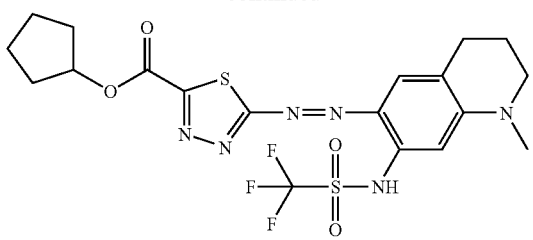
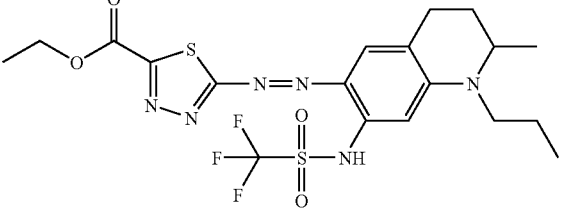
[formulae 32]
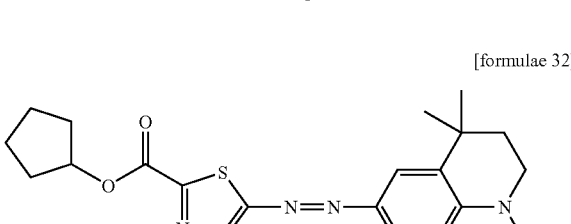
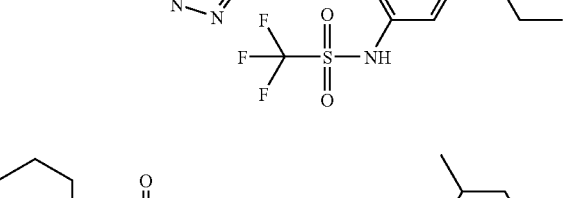
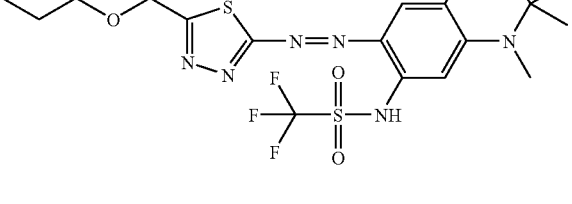
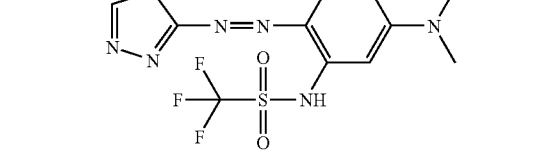

87
-continued
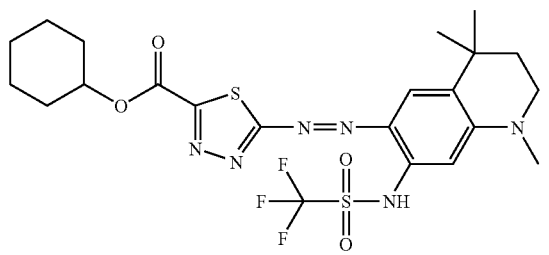
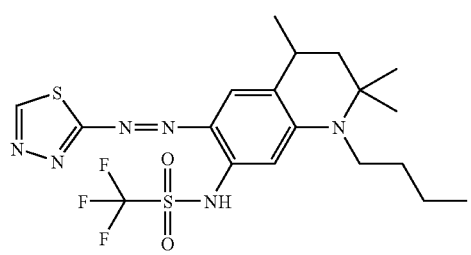
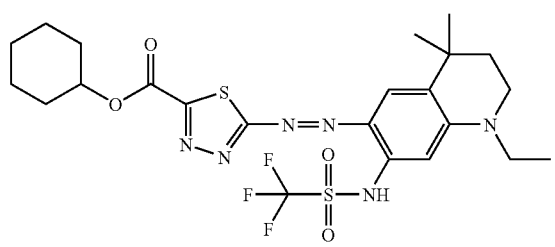
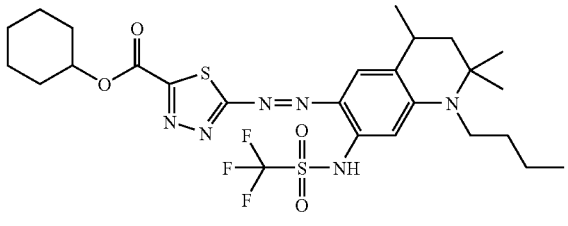
[formulae 33]
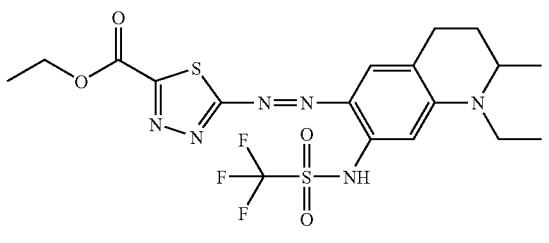
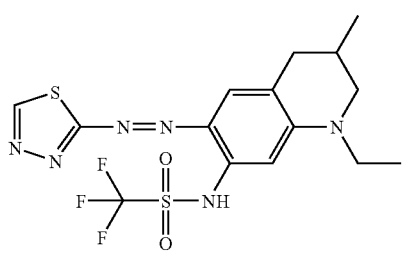
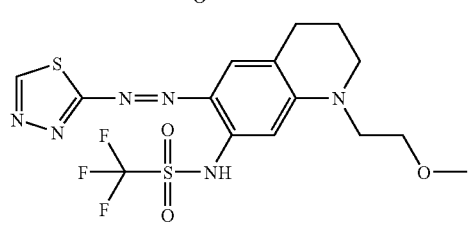
88
-continued
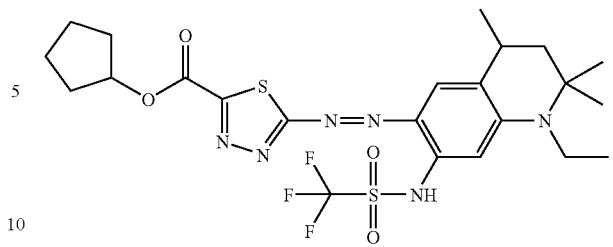
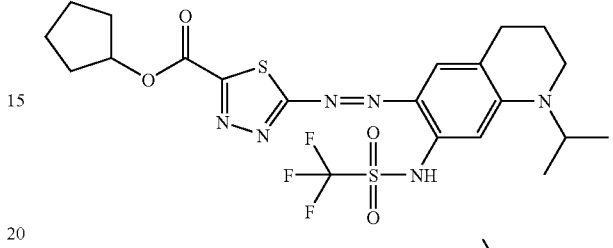
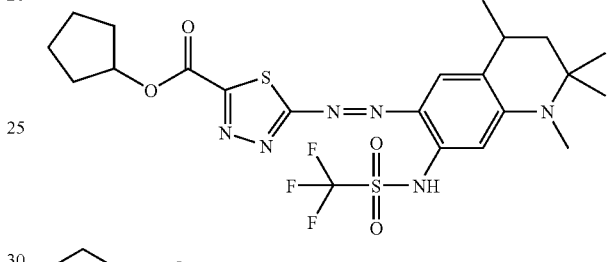
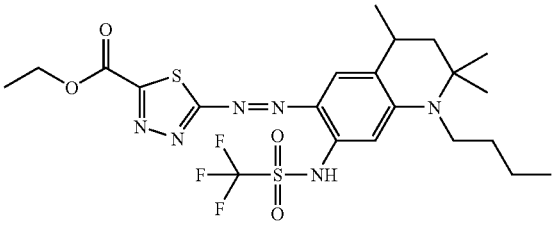
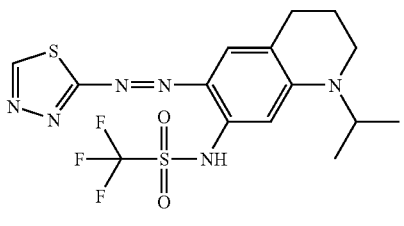
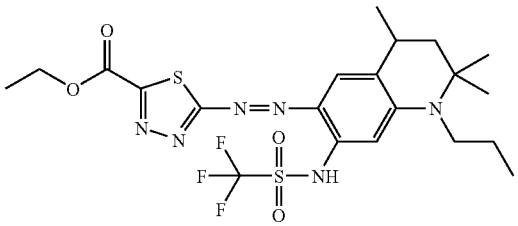

[formulae 34]

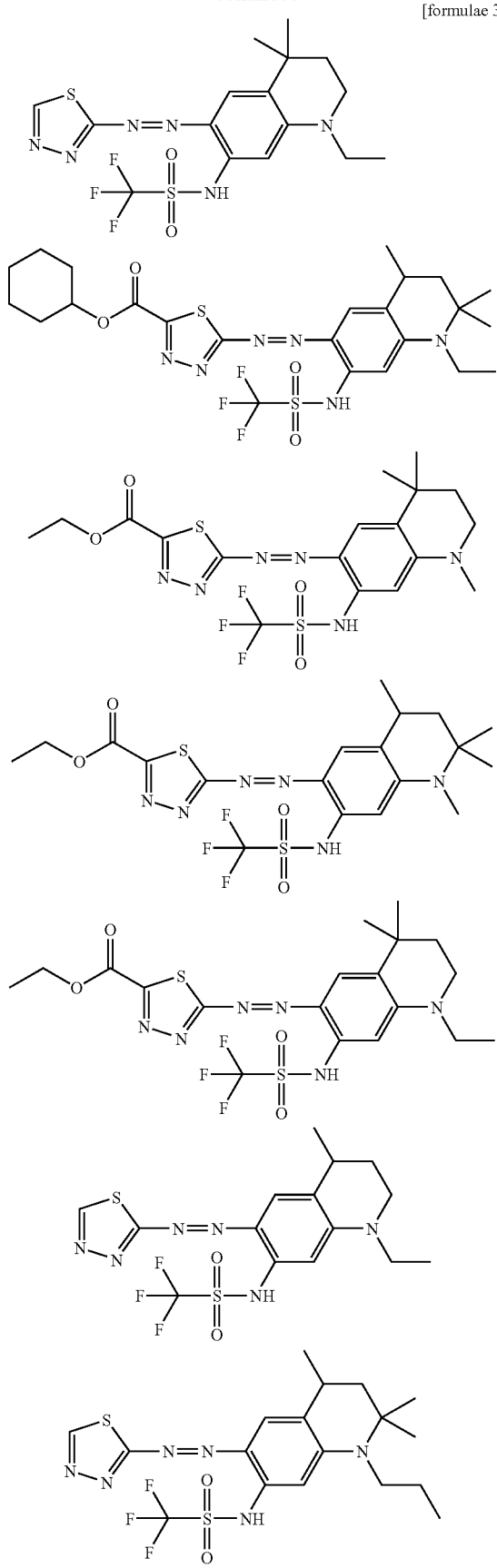
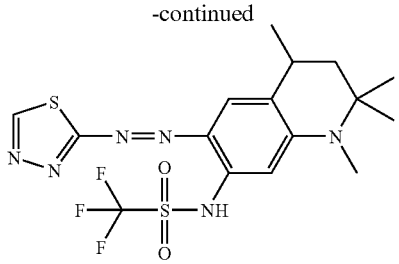

Except for structure, there are no limitations on azo-metal chelate dyes. However, in consideration of applying the azo-metal chelate dyes to optical recording media, which are capable of recording and reading by means of laser light with short wavelengths and are needed in ever-greater numbers in the future, dyes that exhibit the maximum absorption at a wavelength of 700 nm or less are preferable, and dyes that exhibit the maximum absorption at a wavelength ranging from 650 to 500 nm are further preferable, which are measured for a single layer dye film.

In azo-metal chelate dyes to which the present embodiment is applied, as metals that form a chelate with the azo dye compounds represented by the formula (1), various kinds of metals that can form a complex can be employed. For such metals, elements belonging to 9, 10 and 11 groups are preferable. Particularly preferably, at least one such metal is selected from the group consisting of Co, Ni, Cu and Pd. This is because use of the above-described metals makes the shape of absorption spectrum favorable and improves solubility in various solvents, light-resistance and durability.

Hereinafter, an optical recording medium having in a recording layer an azo-metal chelate dye to which the present embodiment is applied will be described.

The optical recording medium to which the present embodiment is applied has a substrate, and a recording layer including an azo-metal chelate dye that has the OD2/OD1 value of which is greater than 1.25. Preferably, the optical recording medium of the present embodiment has a substrate, and a recording layer including an azo-metal chelate dye consisting of the azo dye compound represented by the formula (1) and a metal. The optical recording medium may be a layered-structure in which an under coat layer, a metal reflecting layer, a protection layer and the like are provided on a substrate as appropriate. For the preferable example of the layered-structure, for example, an optical recording medium having high reflectivity can be cited in which a recording layer, a metal reflecting layer and a protection layer are provided on a substrate.

Hereinafter, by taking an optical recording medium having such a layered-structure as an example, a description will be given of an optical recording medium to which the present embodiment is applied.

Basically, the material for the substrate of the optical recording medium to which the present embodiment is applied may be one that is transparent to the recording light and reading light. For example, polymer material such as polycarbonate resin, vinyl chloride resin, acrylic resin such as methyl polymethacrylate, polystyrene resin, epoxy resin, vinyl acetate resin, polyester resin, polyethylene resin, polypropylene resin, polyimide resin and amorphous polyolefin, inorganic material such as glass can be used. Polycarbonate resin is preferably used in light of high throughput, cost, resistance to hygroscopicity and the like.

Using injection molding and the like, these materials for a substrate are molded into a disc shape to serve as a substrate.

It is to be noted that guide grooves and pits may be formed on the surface of the substrate when needed. It is preferable that these guide grooves and pits be provided at a time when the substrate is molded. However, it is also possible to provide guide grooves and pits on the substrate by use of an ultraviolet curing resin layer. When the guide grooves have spiral shapes, it is preferable that the groove pitch be in a range of around 0.4 to 1.2 µm inclusive, particularly preferably in a range of around 0.6 to 0.9 µm inclusive.

In terms of the atomic force microscope (AFM) measurement value, it is preferable that the groove depth is generally in a range of 100 to 200 nm inclusive. In particular, the groove depth is preferably in a range of around 150 to 180 nm inclusive in order to achieve from 1× recording, meaning low-speed, to 8× recording meaning high-speed. When the groove depth is greater than the lower limit, large modulated amplitude can be obtained even in a low-speed recording, when the groove depth is less than the upper limit, sufficient reflectivity can be easily obtained. The groove width is generally in a range of 0.20 to 0.40 µm inclusive in terms of the atomic force microscope (AFM) measurement value. For high-speed recording application, it is further preferable that the groove width be in a range of 0.28 to 0.33 µm inclusive. When the groove width is greater than the lower limit, sufficient push-pull signal amplitude can be easily obtained. Moreover, deformation of the substrate has a significant influence on the amplitude of the recording signal. For this reason, when recording at speeds higher than 8×, setting the groove width to be greater than the above lower limit will suppresses the influence of thermal interference, facilitating to obtain small jitter. Furthermore, wide recording power margin is provided to give excellent recording characteristics and recording conditions, for example, tolerance to variations in laser power is increased. In the case where the groove width is less than the upper limit, when performing low-speed recording such as 1×, it is possible to suppress thermal interference in recording marks and to obtain excellent jitter value.

The optical recording medium to which the present embodiment is applied can record information, such as address information, information about type of media, condition of recording pulse and optimal recording power. Formats such as LPP and ADIP, which are described in DVD-R and DVD+R standards, may be used to record the information.

In the optical recording medium to which the present embodiment is applied, a recording layer including an azo-metal chelate dye having the above-described specific properties and structure is formed on a substrate, or on an under coat layer and the like which have been provided as required. The recording layer including such an azo-metal chelate dye has high sensitivity, high reflectivity and relatively high decomposition temperature (or the temperature at which the amount begins to decrease in terms of TG-DTA measurement). The recording layer including the above-described azo-metal chelate dye can achieve high-speed recording with single composition.

As the conventional recording layers which have been regarded to have high sensitivity, there are known a recording layer which uses a dye having higher absorption coefficient at the recording light wavelength and a recording layer using a low-temperature decomposition dye which decomposes at temperatures lower than 240° C. However, in the former case, it is difficult to obtain a reflectivity of 40% or more using this dye as a single component. In addition, in the latter case, there have been the following problems: that is, deterioration owing to reading light power; crosstalk that occurs because of the tendency of recording marks to spread; and jitter tends to be large because of thermal interference.

On the other hand, according to the recording layer including the azo-metal chelate dye having the above-described specific properties and structure, it is possible to solve these problems and to achieve high-speed recording. Higher reflectivity is obtained in spite of the fact that the dye used in this recording layer has the absorption peak at longer wavelengths, that is, the dye has a high absorption coefficient at recording and reading wavelengths. It is conceivable that reason for this is due to a high refraction index in the recording layer.

Generally, it is believed that it is preferable for the recording layer of an optical recording medium to have a refraction index ranging from 2 to 3 and an extinction coefficient ranging from 0.03 to 0.1 within (recording and reading light wavelength) ±3 nm. In order to perform high-speed recording, it is preferable that the refraction index in this range be as high as possible (for example, 2.5 or more). This is preferable because a higher refraction index makes recording modulation amplitude larger, since it is possible to ensure large optical pith difference at the same film thickness. The higher the refraction index is, the higher the reflectivity of a disc is, thereby leading to high recording modulation amplitude with thinner film thickness. Use of this recording layer having a high refraction index allows for reduction in the film thickness, which is required for high-speed recording at 8× or more, and realizes excellent high-speed recording because thermal interference and crosstalk are suppressed.

As methods of forming the recording layer of the optical recording medium to which the present embodiment is applied, thin-film forming methods that are generally performed, such as vacuum deposition method, sputtering method, doctor blade method, casting method, spin coating method and dipping method can be cited. From the viewpoint of mass productivity and cost, spin coating method is particularly preferable.

When spin coating method is used for forming a film, the rotation speed is preferably in a range of 500 to 10000 rpm. In some cases, treatments like annealing or application of vapor of solvent may be performed after spin coating. Application solvents, which are used when application methods such as doctor blade method, casting method, spin coating method and dipping method are employed to form a recording layer, are not particularly limited unless the substrate is damaged. For the application solvent, for example, a ketone alcohol solvent such as diacetone alcohol, 3-hydroxy-3-methyl-2-butanone; a cellosolve solvent such as methylcellosolve and ethylcellosolve; a chain hydrocarbon solvent such as n-hexane and n-octane; a cyclic hydrocarbon solvent such as cyclohexane, methylcyclohexane, ethylcyclohexane, dimethyl cyclohexane, n-butylcyclohexane, t-butylcyclohexane and cyclooctane; a perfluoroalkylalcohol solvent such as tetrafluoropropanol, octafluoropentanol and hexafluorobutanol; a hydroxycarboxylate solvents such as methyl lactate, ethyl lactate and methyl isobutylate; and the like can be cited.

When forming a recording layer, additives such as quencher, ultraviolet absorber, adhesive and the like may be mixed with the above-described dye as appropriate. Alternatively, substituents having various effects such as quenching effect and ultraviolet absorbing effect can be introduced into the above-described dye. As a singlet oxygen quencher to be added to increase light-resistance and durability of the recording layer, metal complexes such as acethylacetonate complex, bisdithiol complex, such as bisdithio-α-diketone complex and bisphenyldithiol complex, thiocatehol complex, salicylaldehydeoxime complex, and thiobisphenolate complex are preferable. In addition, amine compounds are also preferable.

Moreover, in order to improve recording characteristics and the like, other dyes may be used together. In addition, an azo-metal chelate dye to which the present embodiment is applied can be used in combination with a dye used for low-speed recording in order to implement both of high-speed recording and low-speed recording. However, the mixing ratio thereof should be less than 60% with respect to the weight of the azo-metal chelate dye, preferably 50% or less, and further preferably 40% or less. Meanwhile, when the above-described dye for low-speed recording is used together, the mixing ratio is generally set to 0.01% or more. If the mixing ratio of the dye for low-speed recording is excessively high, it is likely that the recording sensitivity required for high-speed recording at 8× or more cannot be obtained As dyes which can be used together, azo dye compounds which belong to the same family as those represented by the formula (1) can be cited. Moreover, as dyes that can be used together, azo dyes or azo-metal chelate dyes that belong to the same family as the azo-metal chelate dyes having the above-described specific properties or structures, cyanine dyes, squarylium dyes, naphthoquinone dyes, anthraquinone dyes, porphyrin dyes, tetrapyraporphyrazine dyes, indophenol dyes, pyrylium dyes, thiopyrylium dyes, azulenium dyes, triphenylmethane dyes, xanthene dyes, indanthrene dyes, indigo dyes, thioindigo dyes, merocyanine dyes, bis-pyromethene dyes, thiazin dyes, acridine dyes, oxazine dyes, indoaniline dyes and the like can be cited, and dyes belonging to other families may also be used. As agents that accelerate thermal decomposition of dyes, metallic compounds such as metal anti-knocking agents, metallocene compounds and acetylacetonate metal complex can be cited.

Moreover, binders, leveling agents and antifoaming agents can be used together as needed. As preferable binders, polyvinylalcohol, polyvinylpyrrolidone, nitrocellulose, cellulose acetate, ketone resin, acryl resin, polystylene resin, urethane resin, polyvinylbutyral, polycarbonate and polyolefin can be cited.

The film thickness of the recording layer (dye layer) is not particularly limited. However, it is preferable that the thickness be in a range of 50 to 300 nm inclusive. When the film thickness of the dye layer is greater than the above-described lower limit, the influence of thermo diffusion can be suppressed, and therefore it is facilitated to perform favorable recording. In addition, occurrence of distortion in recording signals is reduced, and therefore it is easy to make the signal amplitude large. When the film thickness of the dye layer is less than the above-described upper limit, it is easy to make the reflectivity higher and to provide excellent reading signal characteristics.

Moreover, the groove-portion film thickness of the recording layer is generally in a range of 90 to 180 nm inclusive, preferably in a range of 50 to 90 nm inclusive. The portion-between-grooves film thickness is generally in a range of 50 to 100 nm inclusive, preferably in a range of 30 to 70 nm inclusive. When the groove-portion film thickness or the portion-between-grooves film thickness is greater than the above-described lower limit, it is possible to secure large amplitude of the address information (LPP and ADIP), thereby making it easy to reduce the occurrence of errors. When the groove-portion film thickness or the portion-between-grooves film thickness is less than the above-described upper limit, it is possible to suppress the influence of heat accumulation in recording marks and to prevent increase in crosstalk, thereby making it easy to provide small jitter.

The optical recording medium to which the present embodiment is applied can exhibit a reflectivity of 40% or more by combining the recording layer including the azo-metal chelate dye having the above-described specific properties or structure and the form of the groove provided on a substrate. Thus, for example, DVD-Rs (in terms of standards, there are two types: DVD-R and DVD+Rs, which are collectively referred to as DVD-R hereinafter) can be realized that have reading compatibility with DVD-ROMs. Note that, reflectivity means the value measured by using a disc reader (such as a DVD player, DVD-ROM test system and DVD drive) in which laser having wavelength ranging from 650+10 nm to 650−5 nm is mounted on a pickup when grooves on an optical disc are tracked.

Next, a reflecting layer is preferably formed on the recording layer to have a thickness from 50 to 300 nm. For materials used for the reflecting layer, material exhibiting sufficient reflectivity at the reading light-wavelength can be used. For example, metal such as Au, Al, Ag, Cu, Ti, Cr, Ni, Pt, Ta and Pd can be separately used. Alternatively, alloy of these metals can also be used. Among these, Au, Al and Ag have high reflectivity and therefore are suited for the material for the reflecting layer. In particular, Ag and Ag alloy have excellent reflectivity and thermal conductivity and are therefore preferable. In addition to these metals, the following elements may be contained therein. For example, metals and semimetals such as Mg, Se, Hf, V, Nb, Ru, W, Mn, Re, Fe, Co, Rh, Ir, Cu, Zn, Cd, Ga, In, Si, Ge, Te, Pb, Po, Sn and Bi can be cited. Among these, material which contains Ag as a principal component is particularly preferable, because it is not expensive to manufacture, has tendency to exhibit increased reflectivity when it is combined with azo-metal chelate dye, and provides white beautiful ground color when a print-receiving layer is provided, which will be described later. Here, the principal component means element accounting for 50% or more of the material. It is also possible that thin films having low refraction index are alternately laminated with thin films having high refraction index to form a multi-layered film by using material composed of other than metals, and this multi-layered film is used as the reflecting layer.

As methods for forming the reflecting layer, sputtering method, ion-plating method, chemical vapor deposition and vacuum deposition can be cited. In addition, publicly known organic or inorganic intermediate layer and adhesion layer can be provided on a substrate or under a reflecting layer in order to enhance reflectivity, improve recording characteristics and enhance adherence.

The materials used for a protection layer formed on a reflecting layer are not particularly limited, as long as the reflecting layer is protected from external forces. For example, thermoplastic resin, thermosetting resin, electron beam curing resin, UV curing resin and the like can be cited as organic substance. Moreover, $SiO_2$, $SiN_4$, $MgF_2$, $SnO_2$ and the like can be cited as inorganic substance. Thermoplastic resin, thermosetting resin or the like may be dissolved into an appropriate solvent to obtain an application solution. The application solution may then be applied to a substrate, followed by drying. In this way, thermoplastic resin, thermosetting resin or the like are formed. UV curing resin may be applied to a substrate as it is and cured by UV light. Alternatively, UV curing resin may be dissolved into an appropriate solvent to prepare an application solution. The application solution may then be applied to the substrate, followed by irradiation with UV light for curing. In this way, UV curing resin is formed. For UV curing resin, acrylate resin such as urethane acrylate, epoxy acrylate and polyester acrylate can be used. Separate use or mixed use of these materials may be possible. Additionally, these materials may be used in a form of a single layer film as well as in a form of a multi-layered film.

As in the case of forming a recording layer, as methods for forming the protection layer, coating methods such as spin coating method and casting method, sputtering method, chemical vapor deposition and the like may be used. Among these methods, spin coating method is preferable. The film thickness of the protection layer generally ranges from 0.1 to 100 µm inclusive. In the present embodiment, the film thickness of the protection film preferably equals to 3 µm or more, more preferably equals to 5 µm or more, whereas preferably 30 µm or less, more preferably 20 µm or less.

Note that, the present embodiment is not limited to the foregoing aspects, and various modifications thereof are possible. For example, an optical recording medium may include two or more recording layers. In addition, methods including the following may be used: a method of bonding a substrate having no grooves, which is called a dummy substrate, to the reflecting layer surface; and a method of bonding two optical recording media together in a state where the reflecting layer surfaces are allowed to come in contact with each other. UV curing resin, inorganic thin film or the like may be formed onto the substrate mirror-finished surface in order to protect the surface and to prevent adherence of dusts and the like. Furthermore, a print-receiving layer can also be formed on the protection layer provided on the reflecting layer, or on the substrate bonded to the reflecting layer surface.

Recording to the thus obtained optical recording medium is generally performed by applying laser light to the recording layer(s) provided on one surface or on both surfaces of the substrate. Generally, the portions of the recording layer to which laser light is applied thermally deform, that is, decomposition, heat generation, melting and the like are caused by absorption of laser light energy. The recorded information is generally read by reading the reflectivity difference between the portion where thermal deformation owing to laser light has occurred and the portion where thermal deformation has not occurred.

Lasers used for recording and reading are not particularly limited. However, a dye laser that can be tuned to various wavelengths over the visible range, a helium-neon laser with a wavelength of 633 nm, a high-power semiconductor laser with a wavelength of near 680, 660 or 635 nm, which has been developed recently, a blue laser with a wavelength of near 400 nm and a second harmonic YAG laser with a wavelength of 532 nm, and the like can be used. Among these lasers, the semiconductor laser is suitable because it is compact and lightweight, excellent in handleability and advantageous costwise. In an optical recording medium to which the present embodiment is applied, high density recording and reading can be achieved by using one or a plurality of wavelengths selected among these.

EXAMPLES

Hereinafter, a specific description will be given of the present embodiment on the basis of examples. However, the present examples are not intended to limit the present embodiment as long as it does not depart from the scope thereof.

Example 1

(a) Example of Preparing Compounds (Diazo Coupling)
Here, 1.15 g of 2-amino-1,3,4-thiadiazole (structural formula 1a) was dissolved into a mixture containing 13.7 g of acetic acid, 11.8 g of phosphoric acid and 4.7 g of sulfuric acid. After cooling the resultant solution to 5° C. or less, 3.4 g of 43% nitrosylsulfuric acid was added dropwise to this solution. In this way, a diazo solution of 2-amino-1,3,4-thiadiazole was prepared. Next, the thus obtained diazo solution was added dropwise to 44 ml of methanol solution containing 2.2 g of the compound represented by the following structural formula 1b at 5° C. or less. Thereafter, the resultant solution was stirred for 2 hours. Subsequently, 28% ammonia water was added thereto for neutralization, followed by filtration and purification of the deposited crystal. In this way, 1.3 g of an azo-compound represented by the following structural formula 1c was obtained.

[formulae 35]

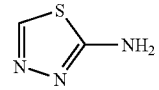

1a

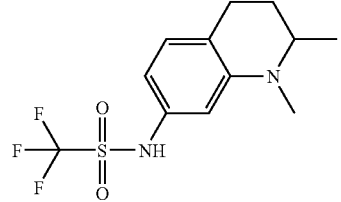

1b

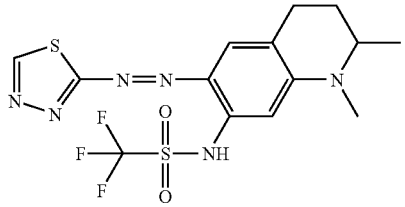

1c (Chelation)
Here, 1.3 g of the azo-compound represented by the structural formula 1c was dissolved into 52 ml of tetrahydrofuran. Then, undissolved components were separated by filtration. Next, 0.47 g of nickel acetate tetrahydrate was dissolved into 7 ml of methanol. The resultant solution was added dropwise to THF solution containing the azo-compound represented by the structural formula 1c at room temperature. Furthermore, 72 ml of water was added to this solution, followed by filtration, purification and drying of the deposited crystal. In this way, 0.8 g of an azo-nickel chelate dye was obtained. This azo-nickel chelate dye showed the maximum absorption wavelength at 588 nm (in chloroform) and 141 L/gcm absorption coefficient per gram. The coating film thereof showed the maximum absorption wavelength at 607 nm.

(b) Recording Example

An octafluoropentanol (hereinafter referred to as OFP) solution containing 1.7 wt % of the thus prepared azo-nickel chelate dye was applied by spin coating on a transparent polycarbonate substrate with guide grooves having 0.74 µm track pitch, 160 nm groove depth and 0.31 µm groove width. Then the substrate was annealed at 100° C. for 20 minutes. This recording layer has the portion-between-grooves film thickness of 55 nm and the groove-portion film thickness of 85 nm. Silver is sputtered on this recording layer to have a thickness of 120 nm, and UV curing resin is applied by spin-coating thereon to have a thickness of 3 μm. Furthermore, after an adhesive was applied by spin coating, a dummy substrate having no grooves (a transparent substrate) was bonded to the substrate. Using a 660 nm semiconductor laser tester (NA=0.65), 8×-speed (28 m/s linear velocity) recording was performed on this disc in accordance with recording pulse condition that is compliant with DVD-R standards ver2.01. Thereafter, the disc was read at 1×-speed (3.5 m/s linear velocity). An excellent result was obtained. Specifically, 8×-speed recording sensitivity was 26.8 mW, and jitter (hereinafter, meaning jitter with respect to clock 1T=38.2 ns) was 8.2%. A 1×-speed recording was performed on this disc, an excellent result was obtained. Specifically, recording sensitivity was 6.2 mW, recording modulation amplitude was 55%, and jitter was 7.8%. The disc exhibited an excellent reflectivity of 47%, which was measured by a DVD-ROM test system (LMA220 manufactured by ShibaSoku Co., Ltd. The measuring was performed at a wavelength of 647 nm).

Incidentally, the upper limit of the power of a recording laser with a wavelength of near 660 nm has been rapidly raised these days. However, in consideration of mass productivity, beam shape (when beam is allowed to have preferable shape, power is reduced) and price, it is preferable that 8×-speed recording sensitivity be around 28 mW. In addition, jitter is less than 9%, preferably less than 8%.

Example 2

(a) Example of Preparing Compounds

Under the same conditions as those in the example 1, the compounds represented by the following structural formulae 2a and 2b were used as starting materials to prepare the azo-compound 2c represented by the following structural formula 2c, and nickel was combined to form an azo-nickel chelate dye. This azo-nickel chelate dye showed the maximum absorption wavelength at 589 nm (in chloroform) and 139 L/gcm absorption coefficient per gram. The coating film thereof showed the maximum absorption wavelength at 609 nm.

[formulae 36]

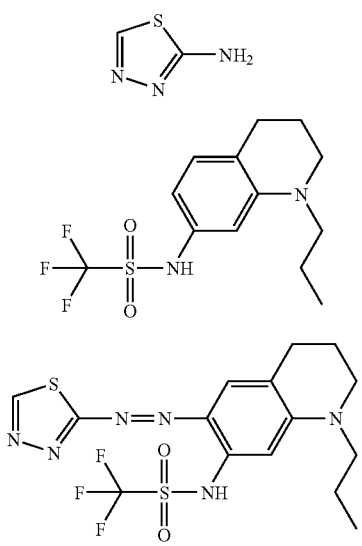

(b) Recording Example

A disc was fabricated under the same conditions as those in the example 1 with the exception that a dye having the structural formula shown above was used and that the film thickness was reduced to 75% of that in the example 1 (the portion-between-grooves film thickness was approximately 41 nm, the groove-portion film thickness was approximately 64 nm). Then, recording and reading of this disc was performed as in the case of the example 1. Excellent results were obtained. Specifically, 8×-speed recording sensitivity was 22 mW, and jitter was 7.7%. The reflectivity was 46%.

Example 3

(a) Example of Preparing Compounds

Under the same conditions as those in the example 1, the compounds represented by the following structural formulae 3a and 3b were used as starting materials to prepare the azo-compound represented by the following structural formula 3c, and an azo-nickel chelate dye composed of nickel and the azo-compound 3c was obtained. This azo-nickel chelate dye showed the maximum absorption wavelength at 588 nm (in chloroform) and 143 L/gcm absorption coefficient per gram. The coating film thereof showed the maximum absorption wavelength at 607 nm.

[formulae 37]

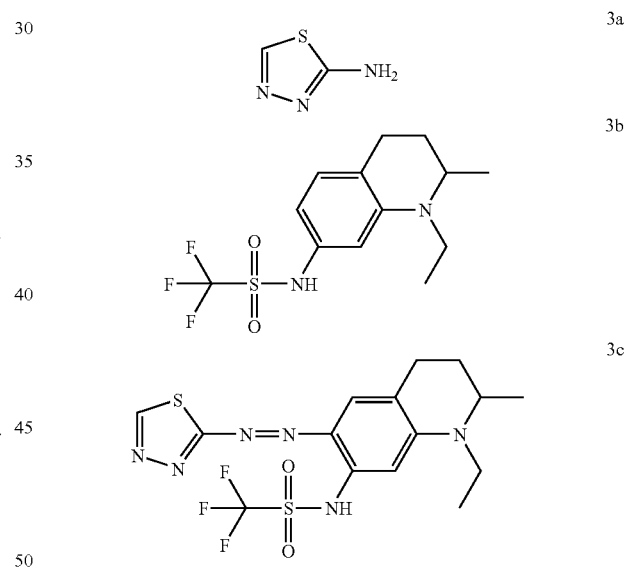

(b) Recording Example

A disc was fabricated under the same conditions as those in the example 2 with the exception that a dye having the structural formula shown above was used. Then, recording and reading of this disc was performed as in the case of the example 2. Excellent results were obtained. Specifically, 8×-speed recording sensitivity was 24.8 mW, jitter was 7.3%, and reflectivity was 47%.

Example 4

(a) Example of Preparing Compounds

Under the same conditions as those in the example 1, the compounds represented by the following structural formulae 4a and 4b were used as starting materials to prepare the azo-compound represented by the following structural formula 4c, and an azo-nickel chelate dye composed of nickel and the azo-compound 4c was obtained. This azo-nickel chelate dye showed the maximum absorption wavelength at 587 nm (in chloroform) and 139 L/gcm absorption coefficient per gram. The coating film thereof showed the maximum absorption wavelength at 610 nm.

(formulae 38)

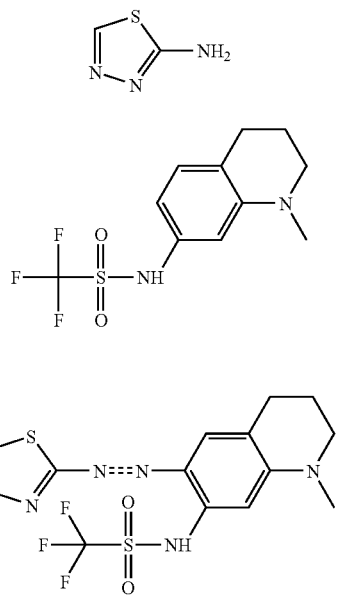

4a

4b

4c (b) Recording Example

A disc was fabricated under the same conditions as those in the example 2 with the exception that a dye having the structural formula shown above was used. Then, recording and reading of this disc was performed as in the case of the example 2. Excellent results were obtained. Specifically, 8x-speed recording sensitivity was 23.6 mW, jitter was 7.2%, and reflectivity was 46%.

Example 5

(a) Example of Preparing Compounds

Under the same conditions as those in the example 1, the compounds represented by the following structural formulae 5a and 5b were used as starting materials to prepare the azo-compound represented by the following structural formula 5c, and an azo-nickel chelate dye composed of nickel and the azo-compound 5c was obtained. This azo-nickel chelate dye showed the maximum absorption wavelength at 587 nm (in chloroform) and 139 L/gcm absorption coefficient per gram. The coating film thereof showed the maximum absorption wavelength at 608 nm.

(formulae 39)

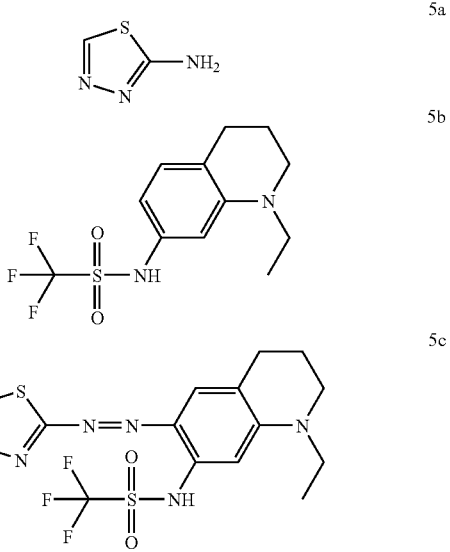

5a

5b

5c (b) Recording Example

A disc was fabricated under the same conditions as those in the example 2 with the exception that a dye having the structural formula shown above was used. Then, recording and reading of this disc was performed as in the case of the example 2. Excellent results were obtained. Specifically, 8x-speed recording sensitivity was 23.6 mW, jitter was 7.4%, and reflectivity was 48%.

Example 6

(a) Example of Preparing Compounds

Under the same conditions as those in the example 1, the compounds represented by the following structural formulae 6a and 6b were used as starting materials to prepare the azo-compound represented by the following structural formula 6c, and an azo-nickel chelate dye composed of nickel and the azo-compound 6c was obtained. This azo-nickel chelate dye showed the maximum absorption wavelength at 590 nm (in chloroform) and 140 L/gcm absorption coefficient per gram. The coating film thereof showed the maximum absorption wavelength at 608 nm.

(formulae 40)

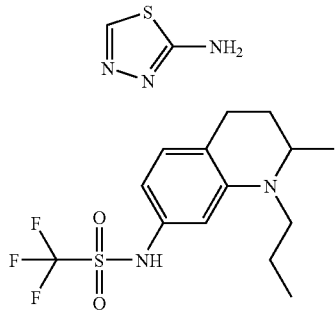

6a

6b

-continued

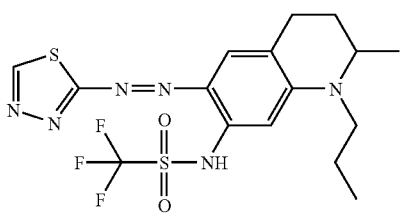

6c (b) Recording Example

A disc was fabricated under the same conditions as those in the example 2 with the exception that a dye having the structural formula shown above was used. Then, recording and reading of this disc was performed as in the case of the example 2. Excellent results were obtained. Specifically, 8×-speed recording sensitivity was 25 mW, jitter was 7.4%, and reflectivity was 47%.

Example 7

(a) Example of Preparing Compounds

Under the same conditions as those in the example 1, the compounds represented by the following structural formulae 7a and 7b were used as starting materials to prepare the azo-compound represented by the following structural formula 7c, and an azo-nickel chelate dye composed of nickel and the azo-compound 7c was obtained. This azo-nickel chelate dye showed the maximum absorption wavelength at 590 nm (in chloroform) and 137 L/gcm absorption coefficient per gram. The coating film thereof showed the maximum absorption wavelength at 609 nm.

(formulae 41)

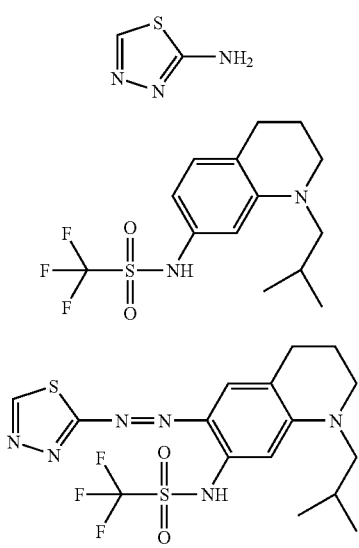

7a

7b

7c (b) Recording Example

A disc was fabricated under the same conditions as those in the example 2 with the exception that a dye having the structural formula shown above was used. Then, recording and reading of this disc was performed as in the case of the example 2. Excellent results were obtained. Specifically, 8×-speed recording sensitivity was 25.8 mW, jitter was 7.6%, and reflectivity was 47%.

Example 8

(a) Example of Preparing Compounds

Under the same conditions as those in the example 1, the compounds represented by the following structural formulae 8a and 8b were used as starting materials to prepare the azo-compound represented by the following structural formula 8c, and an azo-nickel chelate dye composed of nickel and the azo-compound 8c was obtained. This azo-nickel chelate dye showed the maximum absorption wavelength 595 nm (in chloroform) and 137 L/gcm absorption coefficient per gram. The coating film thereof showed the maximum absorption wavelength at 613 nm.

(formulae 42)

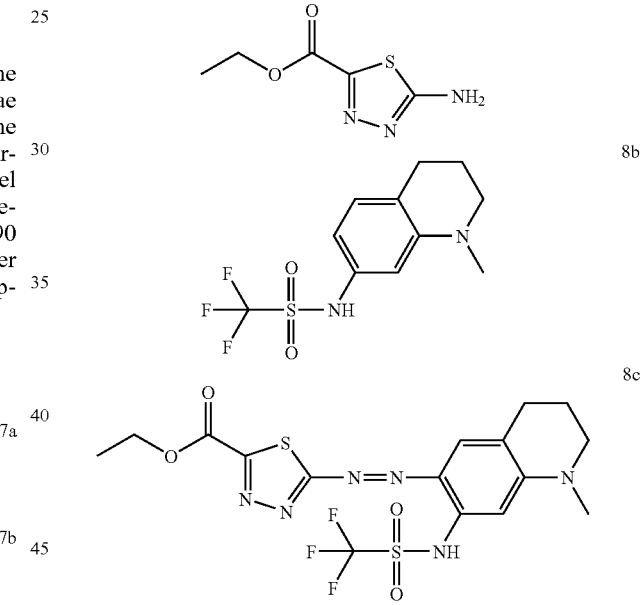

8a

8b

8c (b) Recording Example

A disc was fabricated under the same conditions as those in the example 2 with the except on that a dye having the structural formula shown above was used. Then, recording and reading of this disc was performed as in the case of the example 2. Excellent results were obtained. Specifically, 8×-speed recording sensitivity was 22.8 mW, jitter was 7.8%, and reflectivity was 48%. Note that, the recording modulation amplitude of the discs in the examples 2 to 8 in the case of 1× recording were all in a range of 40 to 50%.

Comparative Example 1

(a) Example of Preparing Compounds

Under the same conditions as those in the example 1, a nickel chelate dye including the azo-compound 101c was obtained. This azo-nickel chelate dye showed the maximum absorption wavelength at 580 nm (in chloroform) and 142 L/gcm absorption coefficient per gram. The coating film thereof showed the maximum absorption wavelength at 598 nm.

(formulae 43)

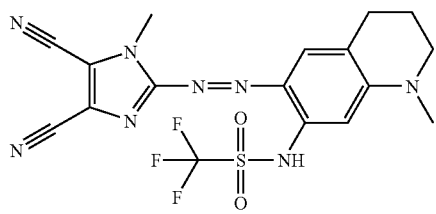

101c (b) Recording Example

A disc was fabricated under the same conditions as those in the example 2 with the exception that a dye having the structural formula shown above was used. Then, recording and reading of this disc was performed as in the case of the example 2. Although the laser light intensity was raised to as high as 28 mW, it was impossible to perform even 4×-speed recording because of poor recording sensitivity (jitter>14%). Note that the reflectivity of this disc was 58%, which was measured using a DVD-ROM test system.

Comparative Example 2

(a) Example of Preparing Compounds

Under the same conditions as those in the example 1, a nickel chelate dye including the azo-compound 102c was obtained. This azo-nickel chelate dye showed the maximum absorption wavelength at 585 nm (in chloroform) and 125 L/gcm absorption coefficient per gram. The coating film thereof showed the maximum absorption wavelength at 604 nm.

(formulae 44)

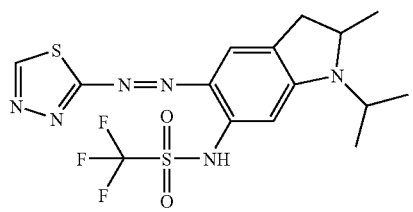

102c (b) Recording Example

A disc was fabricated under the same conditions as those in the comparative example 1 with the exception that a dye having the structural formula shown above was used. Then, recording and reading of this disc were performed as in the case of the example 2. As for the result, sufficient recording sensitivity was not obtained even at 4×-speed recording. The recording sensitivity was 48 mW and insufficient, and jitter was 13' which was poor. Note that the reflectivity of this disc was 48%, which was measured using a DVD-ROM test system.

Example 9

The azo-nickel chelate dye prepared in the example 4 was mixed with the nickel chelate dye prepared in the Comparative example 2 at a weight ratio of 60:40. Then, an OFP solution containing 1.9 wt % of the mixed dye was prepared. Next, this solution was applied by spin coating on a polycarbonate substrate with guide grooves having 0.74 μm track pitch, 163 nm groove depth and 0.32 μm groove width. Thereby, a recording layer having 60 nm portion-between grooves thickness and 90 nm groove portion thickness was formed. Except for this, a disc was fabricated as in the case of the example 2. Then, 8×-speed recording and 1×-speed reading were performed. Here, excellent results were obtained. Specifically, 8×-speed recording sensitivity was 25.4 mW, jitter was 7.3%, and reflectivity was 49%. Meanwhile, even at 1×-speed recording, excellent recording characteristics were obtained. 1×-speed recording sensitivity was 6.0 mW, jitter was 7.1, and recording modulation amplitude was 61%. In other words, recording characteristics were obtained which satisfy DVD-R standards even at 1×-speed recording or 8×-speed recording.

Example 10

A disc was fabricated under the same conditions and using the same methods as those in the example 9 with the exception that the dye prepared in the example 2 and the dye prepared in the comparative example 1 were used. Recording and reading were then performed as in the case of the example 9. As a result, excellent recording and reading characteristics were obtained. Specifically, 8×-speed recording sensitivity was 26 mW, jitter was 7.2%, and reflectivity was 49%. 1×-speed recording sensitivity was 6.2 mW, jitter was 7.1%, and recording modulation amplitude was 60%.

Example 11

A disc was fabricated under the same conditions and using the same methods as those in the example 9 with the exception that a mixed dye, which was obtained by mixing the dye prepared in the example 5 with the dye prepared in the comparative example 1, was used (weight ratio of 60:40). Recording and reading were then performed as in the case of the example 9. As a result, excellent recording and reading characteristics were obtained. Specifically, 8×-speed recording sensitivity was 26.2 mW, jitter was 7.3%, and reflectivity was 50%. 1×-speed recording sensitivity was 6.2 mW, jitter was 7.1%, and recording modulation amplitude was 61%.

Example 12

A disc was fabricated under the same conditions and using the same methods as those in the example 9 with the exception that a mixed dye, which was obtained by mixing the dye prepared in the example 1 with the dye prepared in the comparative example 1 with a weight ratio of 50:50, was used. Recording and reading were then performed as in the case of the example 9. At 28 mW, 8×-speed recording sensitivity was slightly unsatisfactory. However, jitter was 7.5% and reflectivity was 52%. Additionally, excellent 1×-speed recording sensitivity was obtained. Specifically, the recording sensitivity was 6.4 mW, and jitter was 7.1% and recording modulation amplitude was 61%.

Comparative Example 3

(a) Example of Preparing Compounds

Under the same conditions as those in the example 1, a nickel chelate dye including the azo-compound 105c was obtained. This azo-nickel chelate dye showed the maximum absorption wavelength at 589 nm (in chloroform) and 109 L/gcm absorption coefficient per gram. The coating film thereof showed the maximum absorption wavelength at 607 nm.

(formulae 45)

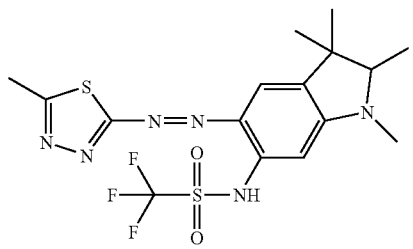

105c (b) Recording Example

A disc was fabricated under the same conditions as those in the example 2 with the exception that a dye having the structural formula shown above was used. Then, recording and reading were performed as in the case of the example 2. At 28 mW, the recording sensitivity was slightly unsatisfactory, showing poor jitter of 9.3%. When recording was performed under the same conditions as those in the example 9 where recording sensitivity can be enhanced, 8×-speed recording sensitivity was 25 mW. However, large thermal interference effect led to poor recording characteristics, i.e., 11% jitter. Note that the reflectivity of this disc was 46%, which was measured using a DVD-ROM test system.

Comparative Example 4

(a) Example of Preparing Compounds

Under the same conditions as those in the example 1, a nickel chelate dye including the azo-compound 106c was obtained. This azo-nickel chelate dye showed the maximum absorption wavelength at 585 nm (in chloroform) and 132 L/gcm absorption coefficient per gram. The coating film thereof showed the maximum absorption wavelength at 609 nm.

(formulae 46)

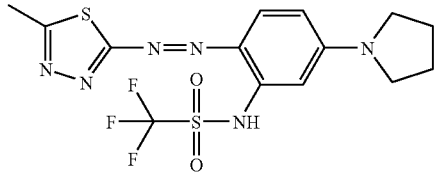

106c (b) Recording Example

A disc was fabricated under the same conditions as those in the example 2 with the exception that a dye having the structural formula shown above was used. Then, recording and reading were performed as in the case of the example 2. Excellent 8×-speed recording sensitivity was obtained, i.e., 22 mW. However, owing to large thermal interference effect, excellent recording characteristics were obtained only at the power smaller than the recording sensitivity by 1 mW. The reflectivity was reduced to 39%, which is not preferable for the reading operation of DVD-Rs.

Comparative Example 5

(a) Example of Preparing Compounds

Under the same conditions as those in the example 1, a nickel chelate dye including the azo-compound 107c was obtained. This azo-nickel chelate dye showed the maximum absorption wavelength at 589 nm (in chloroform) and 91 L/gcm absorption coefficient per gram. The coating film thereof showed the maximum absorption wavelength at 601 nm.

(formulae 47)

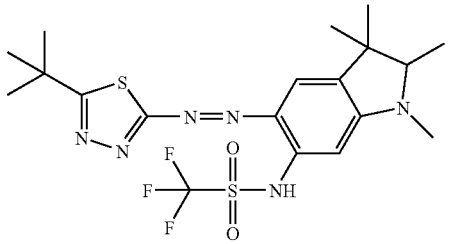

107c (b) Recording Example

A disc was fabricated under the same conditions as those in the example 2 with the exception that a dye having the structural formula shown above was used. Then, recording and reading were performed under the same recording conditions as those of the comparative example 1. However, sufficient recording sensitivity was not provided even at 28 mW and 4×-speed recording, resulting in poor recording performance. Note that the reflectivity of this disc was 46%, which was measured using a DVD-ROM test system.

Comparative Example 6

(a) Example of Preparing Compounds

Here, 13.99 g of 1,2,3,4-tetrahydroquinoline and 14.52 g of potassium carbonate were dissolved into 350 ml of methanol.

The resultant solution was maintained at temperatures between 45° C. and 50° C. with constant mixing. To this solution, 25.54 g of dimethyl sulfate was added dropwise. Subsequently, the solution was stirred for 3 hours at temperatures between 45° C. and 50° C. Thereafter, the solution was left overnight. For toluene extraction, 350 ml of toluene and 350 ml of water were added to this solution. The extracted toluene solution was dried using anhydrous sodium sulfate, followed by removal of toluene to obtain a brown solution. This solution was column-purified to obtain 12.9 g of a pale yellow solution represented by the following structural formula (e).

(formulae 48)

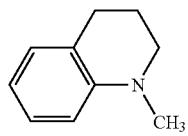

(e)

Here, 12.9 g of the compound represented by the above structural formula (e) was added dropwise to 230 g of concentrated sulfuric acid which had been cooled to between 0° C. and 5° C., while maintaining the temperature at 0° C. to 5° C. Subsequently, a mixture of 36 g of concentrated sulfuric acid and 9.0 g of concentrated nitric acid was added dropwise to the resultant solution while maintaining the temperature at 0° C. to 5° C. After the mixture solution was added, the solution was returned to room temperature, followed by stirring for 2 hours. The reacted solution was poured into 300 ml of ice water for cooling. Then, the solution was adjusted to pH 9 by the addition of 50% aqueous sodium hydroxide while cooling the solution. After stirring for 1 hour, the deposited crystal was separated by filtration and dried. Thus, 12.4 g of red crystal represented by the following structural formula (f) was obtained.

(formulae 49)

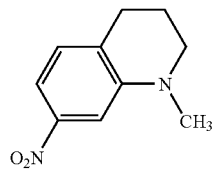

(f)

Here, 31.4 g of iron powder was suspended in 183 ml of DMF-water (2:1) solution, and the solution was heated to between 85° C. and 90° C. with constant mixing. To this solution, a mixture obtained by mixing 6.7 ml of hydrochloric acid with 91.5 ml of DMF-water (2:1) solution was added dropwise. Subsequently, while maintaining the temperature at 85° C. to 95° C., 183 ml of DMF solution containing 12.0 g of the compound represented by the above structural formula (f) was added dropwise to this solution by taking 15 minutes. The resultant solution was stirred for 20 minutes at the temperature between 80° C. to 90° C. Thereafter, while the solution was left for cooling, 6.39 g of sodium hydrogencarbonate was added thereto, followed by stirring for 10 minutes. The solution was then filtrated to remove iron powder, and the filtrate was poured into 500 ml of ice water for toluene extraction. After the resultant solution was dried using anhydrous sodium sulfate, toluene was removed to obtain 5.47 g of a brown liquid represented by the following structural formula (g).

(formula 50)

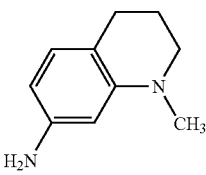

(g)

Under nitrogen flow, 9.31 g of trifluoromethanesulfonic anhydride was stirred, and was maintained a temperature of 20° C. or below. Here, 40 ml of toluene solution containing 5.47 g of the compound represented by the above structural formula (g) was added dropwise. The resultant solution was subsequently stirred for 4 hours at the temperature between 10° C. and 15° C. Thereafter, the solution was left overnight. To the reacted solution, 2 ml of water is added at the temperature between 10° C. to 25° C. and was stirred for 1 hour. Thereafter, the deposited solid substance was the separated by filtration. The substance thus harvested was then dissolved into ethyl acetate, and 150 ml of water was added thereto. Then, the resultant solution was extracted with ethyl acetate. After the resultant solution was dried using anhydrous sodium sulfate, ethyl acetate was removed to obtain 6.87 g of a dark brown liquid represented by the following structural formula (h).

(formula 51)

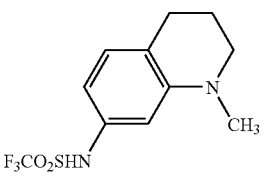

(h)

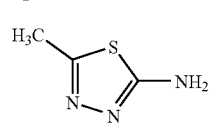

(i)

Here, 0.58 g of 2-amino-5'-methyl-1,3,4-thiadiazole represented by the above-described structural formula (i) was dissolved into a mixture of 5 ml of acetic and 3 ml of propionic acid. To this solution, 1 ml of sulfuric acid was added dropwise at the temperature between 0° C. and 5° C. Then, 1.78 g of 43% nitrosylsulfuric acid was added dropwise to the resultant solution at the temperature between 0° C. and 5° C. In this way, diazotization was performed. Then, 1.77 g of the compound represented by the structural formula (h), 0.2 g of urea and 2.0 g of sodium acetate were dissolved into 20 ml of methanol. To this solution, the resultant diazo solution was added dropwise at the temperature between 0° C. and 5° C. and was stirred for 3 hours. Thereafter, the resultant solution was left overnight. The deposited crystal was separated by filtration and then dried. Thus, 1.44 g of red crystal was obtained which is represented by the following structural formula (j).

(formula 52)

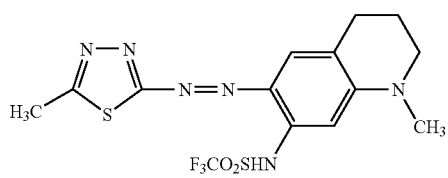

Here, 1.30 g of an azo-compound represented by the structural formula (j), which was obtained as described above, was dissolved into 50 ml of THF. At room temperature, 6 ml of methanol solution containing 0.46 g of nickel acetate tetrahydrate was then added to the resultant solution. Thereafter, this solution was stirred for 3 hours at room temperature, followed by addition of 50 ml of water. The deposited crystal was then separated by filtration, and the obtained crystal was washed with water and dried. In this way, 0.59 g of a nickel chelate compound was obtained. This compound showed λmax at 591 nm ($\epsilon=9.9\times10^4$) (in chloroform), 113 L/gcm absorption coefficient per gram, and the coating film thereof showed the maximum absorption wavelength at 613 nm.

(Measurement of the OD2/OD1 Value)

Here, 20 mg of dyes prepared in the examples 1 to 8 and comparative examples 1 to 6 were respectively added into 2 g of octafluoropentanol (OFP) solvents. Thereafter, supersonic dispersion was performed at temperatures between 50° C. and 55° C. for 60 minutes to obtain solutions A. The solutions A were then cooled to room temperature (25±5° C.). Thereafter, the solutions A were filtrated through 0.2 μm filters (manufactured by Millipore Corporation) to obtain solutions B. The solutions B were respectively applied by spin coating on 1.2 mm thickness polycarbonate substrates having 170 nm groove depth, 500 nm groove width and 1600 nm trackpitch at a rotating speed of 800 rpm. Then, the thus obtained films composed of only dyes were annealed in the constant temperature oven for 5 minutes, where 80° C. air is blowing. Thereafter, the substrates were left in a room, whereby the substrates were cooled to room temperature (fabrication of coated substrates A).

The absorption spectra of these coated substrates A were then measured, wherein the coated substrates A were cut out to have sector shapes and were used as samples to be measured. Air was used as a reference sample. Measurement was then made using U-3300 (manufactured by Hitachi, Ltd.). The following measurement conditions were adopted: wavelength scan speed of 300 nm/min; and optical density measuring (Absorbance) mode at a sampling cycle of 0.5 nm.

FIG. 1 shows the absorption spectrum of the coated substrate A where the dye prepared in the example 1 is used. In addition, Table 1 shows wavelengths and optical densities at OD1 and OD2 as well as the OD2/OD1 value for each coated substrate A.

TABLE 1

| Number | Film OD2 | | Film OD1 | | OD2/OD1 |
| | nm | Abs | nm | Abs | |
| --- | --- | --- | --- | --- | --- |
| Example 1 | 607 | 0.815 | 559 | 0.64 | 1.273438 |
| Example 2 | 609 | 0.805 | 560 | 0.62 | 1.298387 |
| Example 3 | 607 | 0.796 | 558 | 0.618 | 1.288026 |
| Example 4 | 610 | 0.744 | 559 | 0.583 | 1.276158 |
| Example 5 | 608 | 0.797 | 559 | 0.617 | 1.291734 |
| Example 6 | 608 | 0.782 | 559 | 0.604 | 1.294702 |

TABLE 1-continued

| Number | Film OD2 | | Film OD1 | | OD2/OD1 |
| | nm | Abs | nm | Abs | |
| --- | --- | --- | --- | --- | --- |
| Example 7 | 609 | 0.815 | 560 | 0.637 | 1.279435 |
| Example 8 | 613 | 0.754 | 556 | 0.589 | 1.280136 |
| Comparative example 1 | 598 | 0.684 | 547 | 0.589 | 1.16129 |
| Comparative example 2 | 604 | 0.66 | 555 | 0.533 | 1.238274 |
| Comparative example 3 | 607 | 0.643 | 557 | 0.54 | 1.190741 |
| Comparative example 4 | 609 | 0.696 | 557 | 0.597 | 1.165829 |
| Comparative example 5 | 601 | 0.555 | 553 | 0.502 | 1.105578 |
| Comparative example 6 | 613 | 0.625 | 562 | 0.533 | 1.172608 |

Figure 3:
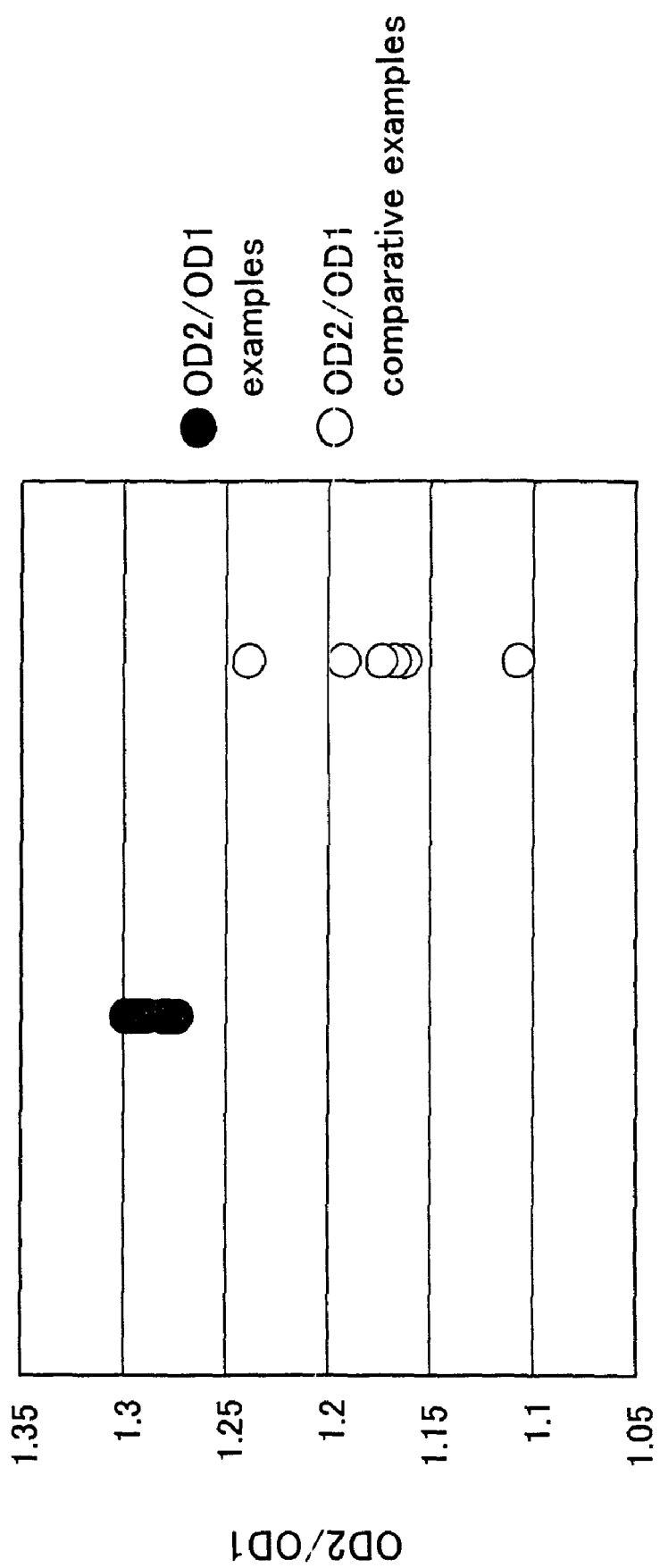
FIG. 3 shows the OD2/OD1 values measured in examples 1 to 8 and in comparative examples 1 to 6.
Figure 4:
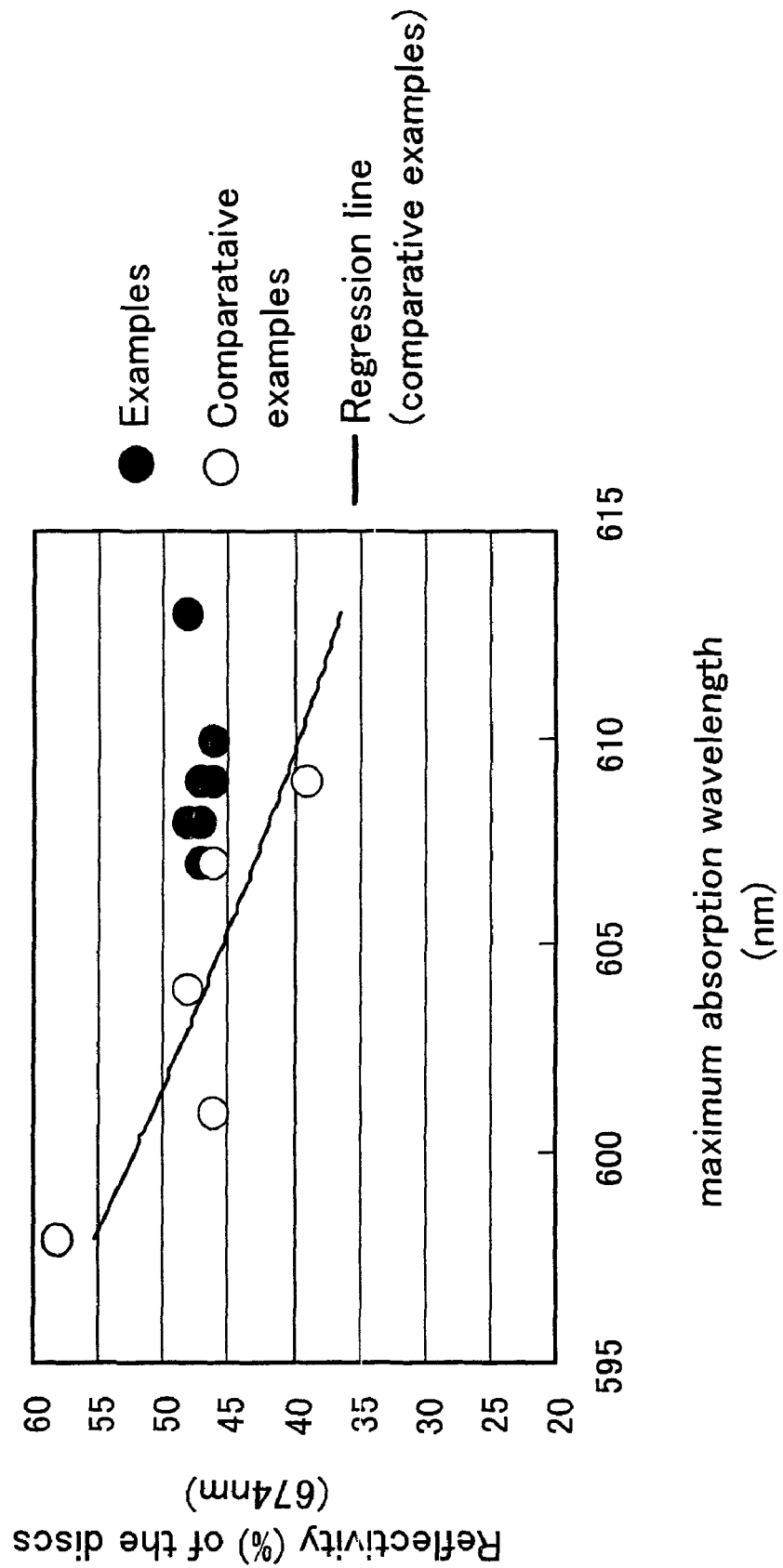
FIG. 4 shows the maximum absorption wavelengths (wavelengths at which the OD2 values are obtained) of the coated substrates A fabricated in the examples 1 to 8 and in the comparative examples 1 to 5, and shows the measurement results for the reflectivity of each of the discs at a 40 mm radius, measured by using a DVD-ROM test system (647 nm).

In addition, FIG. 3 shows the OD2/OD1 values measured in the examples 1 to 8 and in the comparative examples 1 to 6. As can be seen from the results shown in FIG. 3, there is a boundary between the values in the examples 1 to 8 and the values in the comparative examples 1 to 6 at 1.25. Moreover, FIG. 4 shows the maximum absorption wavelengths (wavelengths at which the values are obtained) of the coated substrates A fabricated in the examples 1 to 8 and in the comparative examples 1 to 5, and shows the measurement results for the reflectivity of each of the discs at a 40 mm radius, measured by using a DVD-ROM test system (647 nm). From the results shown in FIG. 4, it can be learned that the discs prepared in the comparative examples 1 to 5 tend to exhibit decreased reflectivity with increase in the maximum absorption wavelengths as indicated by the regression line in FIG. 4. As a trend in the dyes prepared in the comparative examples 1 to 5, it is difficult to obtain a reflectivity of 45% or more that is required in the DVD standards for reading by using dyes having the absorption maximum at wavelengths longer than 605 nm. On the other hand, it can be determined that the discs using the dyes prepared in the examples 1 to 8 allow to secure high reflectivity even when dyes having the absorption maximum at the vicinity of 610 nm are used.

(Measurement of Reference Data)

Here, 0.06 g of the azo-metal chelate dyes, respectively represented by the following structural formulae (S-1) to (S-6) were added to 5 g of OFP solvents, and were subject to supersonic dispersion at 50° C. for 60 minutes. Thereafter, the solutions were left in a room, whereby the solutions were cooled to room temperature. The solutions were then filtrated through 0.2 μm filters (manufactured by Millipore Corporation). The resultant solutions were applied by spin coating on mirror-finished surface replicas (polycarbonate substrates with no guide grooves) so that substantially half area of each disc surface was covered. After drying, a reflecting layer was sputtered on a part of a recording layer formed by the spin-coating. The step height between the uncoated portion covered with the reflecting layer and the recording layer covered with the reflecting layer was measured by using a three-dimensional surface roughness meter (ZYGO: Maxim 5800, manufactured by Canon Inc.), whereby the film thickness was determined. In addition, using the automatic wavelength-scanning ellipsometer (MEL-30S, manufactured by JASCO Corporation), light with wavelengths between 580 and 650 nm was applied to the recording layer to which the reflecting layer was not applied, thereby measuring the reflectivity and the phase difference in variable-angle measurement mode. Then, with reference to the above-described film thickness, the combination of refraction index n and extinction coefficient k, which gives favorable convergence, was determined for each wavelength. Among the refraction indices for the wavelengths thus obtained, the refraction index that gives the maximum value is defined as n.

Meanwhile, for each of the (S-1) to (S-6) dyes, a coated substrate A formed by use of the dye was fabricated and the absorption spectrum was measured as in the case of the above-described "method of measuring the OD2/OD1 value" Then the OD2/OD1 values were calculated.

Table 2 and FIG. 2 show the thus determined OD2/OD1 values and n values (maximum refraction indices). Starting from the left side (i.e., from the smallest OD2/OD1 value to the largest one), data points respectively represent the values for the (S-1) to (S-6) dyes.

TABLE 2

| Dye | OD2/OD1 | n(max) |
| --- | --- | --- |
| S-1 | 0.83 | 2.32 |
| S-2 | 0.85 | 2.5 |
| S-3 | 1 | 2.8 |
| S-4 | 1.03 | 2.9 |
| S-5 | 1.16 | 3 |
| S-6 | 1.21 | 3.2 |

(formulae 53)

S-1

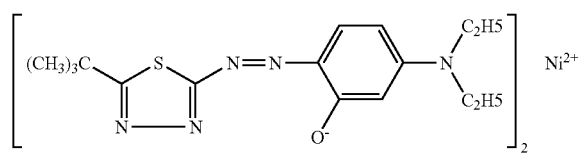

S-2

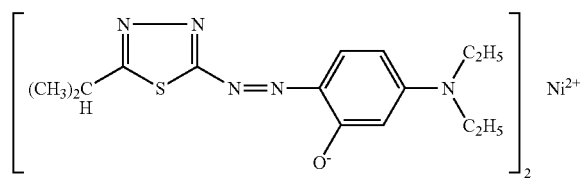

S-3

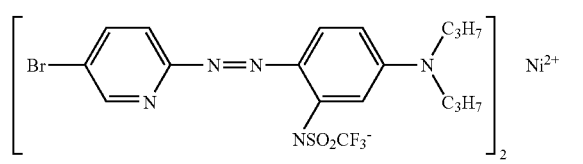

S-4

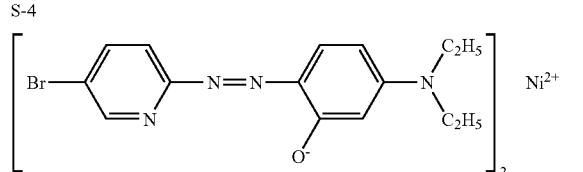

S-5

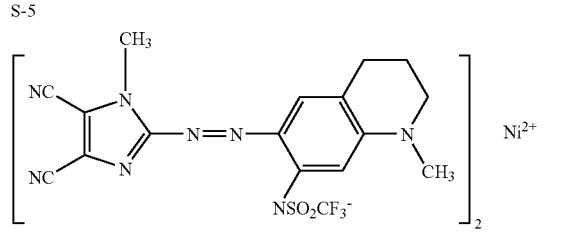

S-6

TABLE 2-continued

| Dye | OD2/OD1 | n(max) |
| --- | --- | --- |

Example 13

(a) Example of Preparing Compounds

Under the same conditions as those in the example 1, the compounds represented by the following structural formulae 13a and 13b were used as starting materials to prepare the azo-compound represented by the following structural formula 13c, and nickel was combined to form an azo-nickel chelate dye. This azo-nickel chelate dye showed the maximum absorption wavelength at 588 nm (in chloroform) and 130 L/gcm absorption coefficient per gram. The coating film thereof showed the maximum absorption wavelength at 604 nm.

(formulae 54)

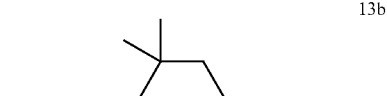

13a

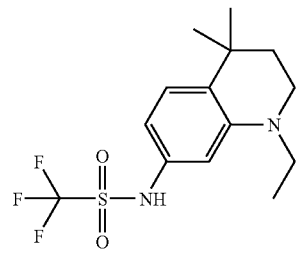

13b

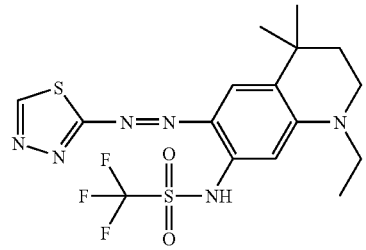

13c

Example 14

(a) Example of Preparing Compounds

Under the same conditions as those in the example 1, the compounds represented by the following structural formulae 14a and 14b were used as starting materials to prepare the azo-compound represented by the following structural formula 14c, and nickel was combined to form an azo-nickel chelate dye. This azo-nickel chelate dye showed the maximum absorption wavelength at 591 nm (in chloroform) and 133 L/gcm absorption coefficient per gram. The coating film thereof showed the maximum absorption wavelength at 607 nm.

(formulae 55)

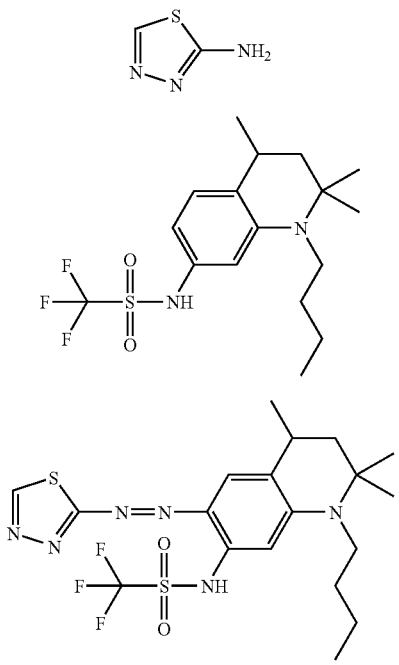

14a

14b

14c

Example 15

(a) Example of Preparing Compounds

Under the same conditions as those in the example 1, the compounds represented by the following structural formulae 15a and 15b were used as starting materials to prepare the azo-compound represented by the following structural formula 15c, and nickel was combined to form an azo-nickel chelate dye. This azo-nickel chelate dye showed the maximum absorption wavelength at 588 nm (in chloroform) and 138 L/gcm absorption coefficient per gram. The coating film thereof showed the maximum absorption wavelength at 608 nm.

(formulae 56)

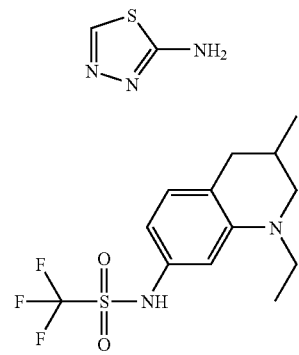

15a

15b

-continued

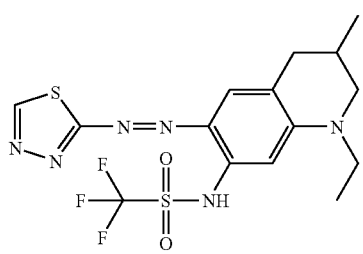

15c

Example 16

(a) Example of Preparing Compounds

Under the same conditions as those in the example 1, the compounds represented by the following structural formulae 16a and 16b were used as starting materials to prepare the azo-compound represented by the following structural formula 16c, and nickel was combined to form an azo-nickel chelate dye. This azo-nickel chelate dye showed the maximum absorption wavelength at 587 nm (in chloroform) and 140 L/gcm absorption coefficient per gram. The coating film thereof showed the maximum absorption wavelength at 607 nm.

(formulae 57)

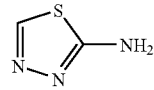

16a

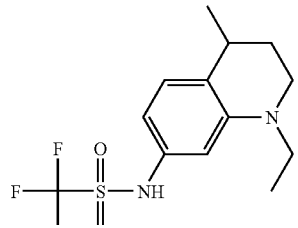

16b

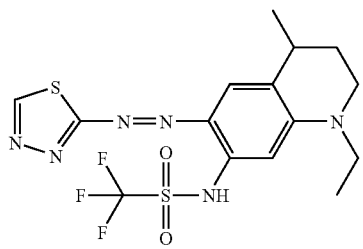

16c

Example 17

(a) Example of Preparing Compounds

Under the same conditions as those in the example 1, the compounds represented by the following structural formulae 17a and 17b were used as starting materials to prepare the azo-compound represented by the following structural formula 17c, and nickel was combined to form an azo-nickel chelate dye. This azo-nickel chelate dye showed the maximum absorption wavelength at 596 nm (in chloroform) and 150 L/gcm absorption coefficient per gram. The coating film thereof showed the maximum absorption wavelength at 613 nm.

(formulae 58)

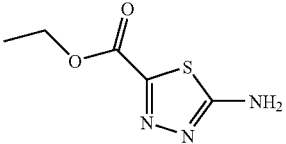
17a

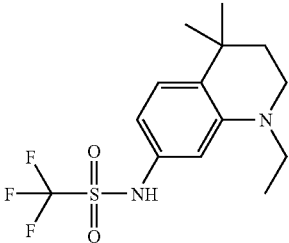
17b

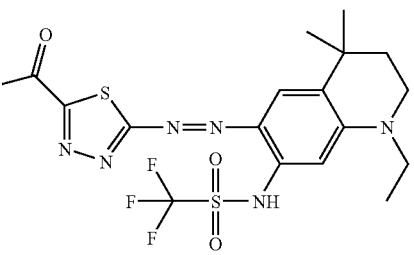
17c

Example 18

(a) Example of Preparing Compounds

Under the same conditions as those in the example 1, the compounds represented by the following structural formulae 18a and 18b were used as starting materials to prepare the azo-compound represented by the following structural formula 18c, and nickel was combined to form an azo-nickel chelate dye. This azo-nickel chelate dye showed 598 nm maximum absorption wavelength (in chloroform) and 139 L/gcm absorption coefficient per gram. The coating film thereof showed the maximum absorption wavelength at 613 nm.

(formulae 59)

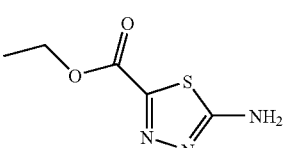
18a

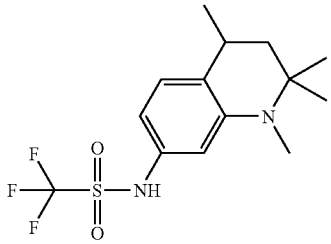
18b

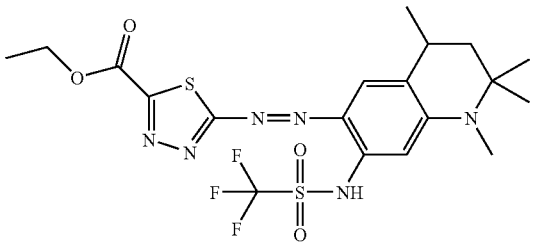
18c

For each of the dyes prepared in the above-described examples 13 to 18, a coated substrate A formed by use of the dye was fabricated and the absorption spectrum was measured as in case of the above-described "method of measuring the OD2/OD1 value." Then the OD2/OD1 values were calculated. Table 3 shows the thus calculated OD2/OD1 values.

As described in Table 3, an excellent result was obtained. Specifically, the OD2/OD1 values were greater than 1.25 in all the examples 13 to 18.

TABLE 3

| Number | Film OD2 | | Film OD1 | | OD2/OD1 |
|---|---|---|---|---|---|
| | nm | Abs | nm | Abs | |
| Example 13 | 604 | 0.8422 | 557 | 0.602 | 1.399 |
| Example 14 | 607 | 0.8146 | 559 | 0.634 | 1.28486 |
| Example 15 | 608 | 0.8113 | 559.5 | 0.628 | 1.29188 |
| Example 16 | 607 | 0.8178 | 558.5 | 0.616 | 1.3276 |
| Example 17 | 613 | 0.8813 | 564.5 | 0.647 | 1.36213 |
| Example 18 | 613 | 0.7508 | 566 | 0.564 | 1.33121 |

INDUSTRIAL APPLICABILITY

According to the present invention, it is possible to provide an azo-metal chelate dye allowing for high-speed recording and an optical recording medium using this azo-metal chelate dye, which is capable of high-speed recording.

Note that, the present application is based on Japanese Patent Application No. 2003-319766 filed on Sep. 11, 2003, and its entirety is incorporated by reference.

The invention claimed is:

1. An azo-metal chelate dye comprising an azo dye compound and a metal, wherein the azo-metal chelate dye has a $OD_2/OD_1$ value of greater than 1.25, which is measured by the following method:
    (1) after adding 20 mg of azo-metal chelate dye into 2 g of an octafluoropentanol (OFP) solvent, supersonic dispersion is performed at temperatures between 50° C. and 65° C. for 60 minutes to obtain a solution A, and the solution A is then cooled to room temperature (25±5° C.) to obtain a solution B;
    (2) the solution B is applied onto a polycarbonate substrate by spin coating at a rotating speed of 800 rpm, and the substrate onto which the elution B has been spin coated is then annealed at 80° C. for 5 minutes, the substrate thus obtained, onto which the solution B has been spin coated, being referred to as a coated substrate A;

(3) the absorption spectrum of the coated substrate A is measured in a range of 400 to 800 nm; and (4) concerning the absorption peaks seen in a range of 500 to 700 nm in the obtained absorption spectrum, the absorption peak at which the optical density is the greatest and the absorption peak at which the optical density is the second greatest are selected, the optical density at the peak on the long wavelength side is defined as $OD_2$ and the optical density at the peak on the short wavelength side is defined as $OD_1$, and the $OD_2/OD_1$ value is calculated, wherein the azo dye compound is represented by the following formula (1):

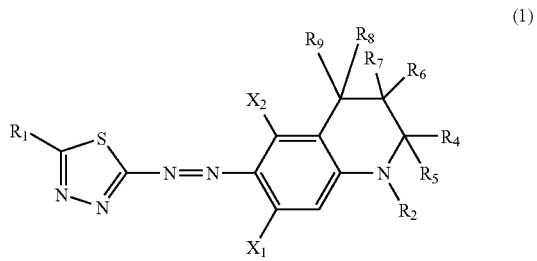

(where $R_1$ represents a hydrogen atom or an ester group represented as $CO_2R_3$, $R_3$ represents a straight or branched chain alkyl group which may be substituted or a cycloalkyl group which may be substituted, $R_2$ represents a straight or branched chain alkyl group which may be substituted, at least one of $X_1$ and $X_2$ represents an $NHSO_2Y$ group, Y represents a straight or branched chain alkyl group which is substituted with at least two fluorine atoms, $R_4$ and $R_5$ independently represents a hydrogen atom or a straight or branched chain alkyl group which may be substituted, and $R_6$, $R_7$, $R_8$ and $R_9$ independently represents a hydrogen atom or a alkyl group having 1 to 2 carbon atoms).

2. The azo-metal chelate dye according to claim 1, wherein the metal is at least one selected from the group consisting of Ni, Co, Cu and Pd.

3. The azo-metal chelate dye according to claim 1, having a maximum absorption at a wavelength of 700 nm or less.

4. The azo-metal chelate dye according to claim 1, having a maximum absorption at a wavelength of from 650 to 500 nm.

5. The azo-metal chelate dye according to claim 1, having a $OD_2/OD_1$ value of 1.29 or more.

6. An optical recording medium comprising a recording layer on a substrate, on which recording layer recording and/or reading of information is performed by use of applied light, wherein the recording layer contains the azo-metal chelate dye according to claim 1.

7. The optical recording medium according to claim 6, wherein the metal is at least one selected from the group consisting of Ni, Co, Cu and Pd.

8. The optical recording medium according to claim 6, wherein the azo-metal chelate dye exhibits the absorption maximum at wavelengths equal to or shorter than 650 nm with regard to the applied light.

9. The optical recording medium according to claim 6, wherein the recording of information thereon is capable at a speed approximately 28 m/s or more.

10. The optical recording medium according to claim 6, wherein the recording of information thereon is capable at 8×-speed.

11. The optical recording medium according to claim 6, having a maximum absorption at a wavelength of 700 nm or less.

12. The optical recording medium according to claim 6, having a maximum absorption at a wavelength of from 650 to 500 nm.

13. The optical recording medium according to claim 6, wherein the azo-metal chelate dye has a $OD_2/OD_1$ value of 1.29 or more.

14. The optical recording medium according to claim 6, wherein the metal is at least Ni.

* * * * *